US011098133B2

(12) United States Patent
Duraj-Thatte et al.

(10) Patent No.: US 11,098,133 B2
(45) Date of Patent: Aug. 24, 2021

(54) METHODS OF MAKING GELS AND FILMS USING CURLI NANOFIBERS

(71) Applicant: President and Fellows of Harvard College, Cambridge, MA (US)

(72) Inventors: Anna M. Duraj-Thatte, Boston, MA (US); Noémie-Manuelle Dorval Courchesne, Montréal (CA); Neel Satish Joshi, Somerville, MA (US)

( * ) Notice: Subject to any disclaimer, the term of this patent is extended or adjusted under 35 U.S.C. 154(b) by 0 days.

(21) Appl. No.: 16/302,687

(22) PCT Filed: May 19, 2017

(86) PCT No.: PCT/US2017/033579
§ 371 (c)(1),
(2) Date: Nov. 19, 2018

(87) PCT Pub. No.: WO2017/201428
PCT Pub. Date: Nov. 23, 2017

(65) Prior Publication Data
US 2019/0127490 A1    May 2, 2019

Related U.S. Application Data

(60) Provisional application No. 62/338,835, filed on May 19, 2016.

(51) Int. Cl.
| | | |
|---|---|---|
| C08J 3/075 | (2006.01) | |
| C07K 17/04 | (2006.01) | |
| A61K 49/00 | (2006.01) | |
| A61K 9/70 | (2006.01) | |
| C07K 14/245 | (2006.01) | |
| C07K 14/47 | (2006.01) | |
| C08J 5/18 | (2006.01) | |
| C12N 15/62 | (2006.01) | |
| B82Y 30/00 | (2011.01) | |
| C12N 5/00 | (2006.01) | |

(52) U.S. Cl.
CPC ............ *C07K 17/04* (2013.01); *A61K 9/7007* (2013.01); *A61K 49/0073* (2013.01); *C07K 14/245* (2013.01); *C07K 14/4711* (2013.01); *C08J 3/075* (2013.01); *C08J 5/18* (2013.01); *C12N 15/62* (2013.01); *B82Y 30/00* (2013.01); *C07K 2319/41* (2013.01); *C07K 2319/42* (2013.01); *C07K 2319/43* (2013.01); *C12N 5/0018* (2013.01)

(58) Field of Classification Search
None
See application file for complete search history.

(56) References Cited

U.S. PATENT DOCUMENTS

| | | |
|---|---|---|
| 5,762,620 A | 6/1998 | Cartmell et al. |
| 6,864,365 B1 | 3/2005 | White et al. |
| 8,741,417 B2 | 6/2014 | Lee et al. |
| 9,095,558 B2 | 8/2015 | Mayes et al. |
| 9,815,871 B2 * | 11/2017 | Joshi ................. C07K 14/245 |
| 10,550,160 B2 | 2/2020 | Joshi et al. |
| 2004/0220296 A1 | 11/2004 | Lowman et al. |
| 2010/0016549 A1 | 1/2010 | O'Mahony et al. |
| 2011/0033389 A1 | 2/2011 | Chen et al. |
| 2011/0108199 A1 | 5/2011 | Miller |
| 2012/0190566 A1 | 7/2012 | Lindquist et al. |
| 2013/0040889 A1 | 2/2013 | Bolt et al. |
| 2013/0136697 A1 | 5/2013 | Kannan et al. |
| 2014/0105861 A1 | 4/2014 | March et al. |
| 2014/0302043 A1 | 10/2014 | Whittle |
| 2014/0370013 A1 | 12/2014 | Desjarlais et al. |
| 2015/0342893 A1 | 12/2015 | Coulter et al. |
| 2018/0258435 A1 * | 9/2018 | Joshi ..................... A61K 35/74 |
| 2020/0248190 A1 | 8/2020 | Joshi et al. |
| 2020/0255480 A1 | 8/2020 | Joshi et al. |

FOREIGN PATENT DOCUMENTS

| | | |
|---|---|---|
| JP | 2006/503545 A | 2/2006 |
| JP | 2008/531059 A | 8/2008 |
| JP | 2009/73766 A | 4/2009 |
| JP | 2010/515445 A | 5/2010 |
| JP | 2014/156428 A | 8/2014 |
| JP | 2014/527405 A | 10/2014 |
| KR | 20120060442 A | 6/2012 |
| WO | WO-2003/068934 A2 | 8/2003 |
| WO | WO-2006/096515 A2 | 9/2006 |
| WO | WO-2008/084115 A2 | 7/2008 |
| WO | 2011/126174 A1 | 10/2011 |
| WO | 2012/138570 A2 | 10/2012 |
| WO | WO-2012/166906 A1 | 12/2012 |
| WO | WO-2013/009545 A1 | 1/2013 |
| WO | WO-2013/020074 A2 | 2/2013 |

(Continued)

OTHER PUBLICATIONS

Klein et al. 2018 (Structure-Function Analysis of the Curli Accessory Protein CsgE Defines Surfaces Essential for Coordinating Amyloid Fiber Formation; mBio 9:e01349-18. https://doi.org/10.1128/mBio.01349-18; (Year: 2018).*

Nash 2015 (Engineering a Functionalized Biofilm-Based Material for Modulating *Escherichia coli*'s Effects in the Mammalian Gastrointestinal Tract. Bachelor's thesis, Harvard College; http://nrs.harvard.edu/urn-3:HUL.InstRepos:17417585; (Year: 2015).*

Lieleg et al. 2011 (Biological hydrogels asselective diffusion barriers; Trends in Cell Biology 21(9): 543-551) (Year: 2011).*

International Search Report and Written Opinion for Application No. PCT/US2017/033579, dated Oct. 2, 2017, 22 pages.

(Continued)

*Primary Examiner* — Mary Maille Lyons
(74) *Attorney, Agent, or Firm* — Dana M. Gordon; Foley Hoag LLP

(57) ABSTRACT

Provided are compositions and methods of making hydrogels, aerogels, films and composites directly from a microbial culture or complex mixture using curli nanofibers.

13 Claims, 39 Drawing Sheets

Specification includes a Sequence Listing.

(56) References Cited

FOREIGN PATENT DOCUMENTS

| WO | WO-2013/188529 A1 | 12/2013 | |
|---|---|---|---|
| WO | WO-2014/078489 A1 | 5/2014 | |
| WO | WO-2014/139468 A1 | 9/2014 | |
| WO | 2014/176311 A1 | 10/2014 | |
| WO | WO-2015080671 A1 * | 6/2015 | ............ A61K 38/06 |
| WO | WO-2015/097289 A1 | 7/2015 | |
| WO | WO-2016/164422 A2 | 10/2016 | |

OTHER PUBLICATIONS

International Preliminary Report on Patentability for Application No. PCT/US2017/033579, dated Nov. 29, 2018, 20 pages.

Chen et al., "Fusion Protein Linkers: Property, Design, and Functionality," Adv Drug Deliv Rev, 65(10): 1357-1369 (32 pages)(2013).

Chen et al., "Synthesis and patterning of tunable multiscale materials with engineered cells," Nature Materials, 13 (5): 515-23 and Supplementary Information (20 pages)(2014).

Courchesne et al., "Scalable Production of Genetically Engineered Nanofibrous Macoscopic Material via Filtration," ACS Biomater. Sci. Eng., 3: 733-741 and supporting information (2017).

Hancock et al., "Probiotic *Escherichia coli* strain Nissle 1917 outcompetes intestinal pathogens during biofilm formation," Journal of Medical Microbiology, 59(4): 392-399 2010.

International Search Report and Written Opinion for International Application No. PCT/US2016/026161 dated Dec. 19, 2016.

International Search Report for Application No. PCT/US2014/035095, dated Sep. 30, 2014, 5 pages.

Men et al., "An auto-biotinylated bifunctional protein nanowire for ultra-sensitive molecular biosensin.," Biosens Bioelectron, 26(4): 1137-41 (2010).

Nguyen et al., "Programmable biofilm-based materials from engineered curli nanofibres," Nature Communications, 5(17): 4945 (10 pages) 2014.

Nussbaumer et al., "Bootstrapped Biocatalysis: Biofilm-Derived Materials as Reversibly Functionalizable Multienzyme Surfaces," ChemCatChem Communications, 9: 4328-4333 and supporting information 2017.

Tukel et al., "CsgA is a pathogen-associated molecular pattern of *Salmonella enterica* serotype Typhimurium that is recognized by Toll-like receptor 2," Mol Microbiol., 58(1): 289-304. (2005).

Van Gerven et al., "Secretion and functional display of fusion proteins through the curli biogenesis pathway," Mol Microbiol., 91 5 : 1022-35 (2014).

Veggiani et al., "Superglue from bacteria: unbreakable bridges for protein nanotechnology," Trends Biotechnol., 32 10 : 506-12 (2014).

Wang et al., "The molecular basis of functional bacterial amyloid polymerization and nucleation," J Biol Chem., 283(31): 21530-9 (2008).

Zakeri et al., "Peptide tag forming a rapid covalent bond to a protein, through engineering a bacterial adhesin," PNAS,109: E690-E697 (2012).

Zhang et al., "Panning and Identification of a Colon Tumor Binding Peptide from a Phage Display Peptide Library," Journal of Biomolecular Screening, 12(3): 429-435 (2007).

* cited by examiner

FIG. 1A
TFF2
(anti-inflammatory cytokine)
106 aa
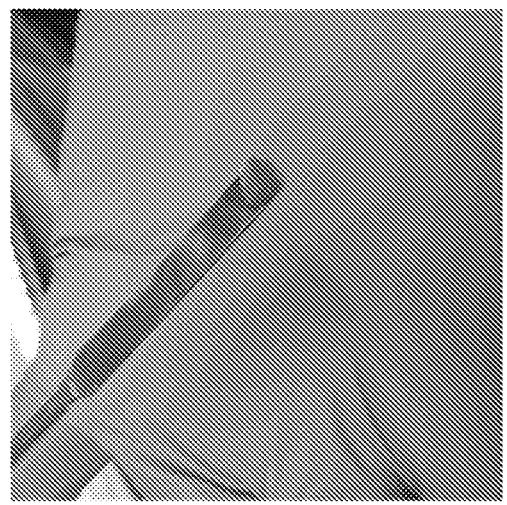
FIG. 1B
MAM
(microbial anti-inflammatory molecule)
135 aa
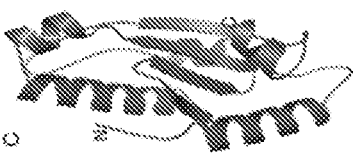
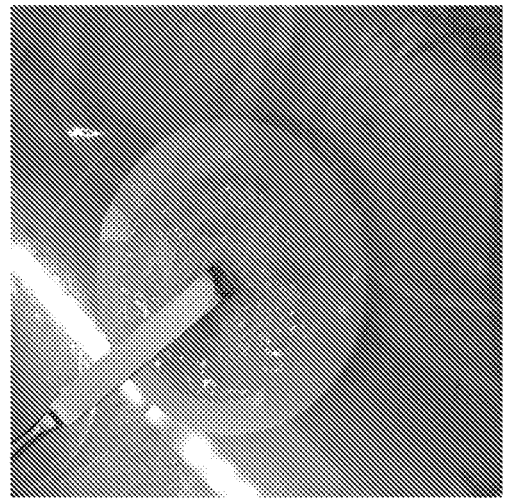

FIG. 2A
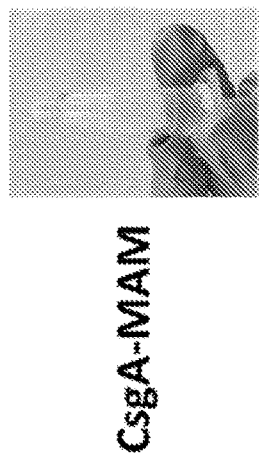
CsgA-TFF2
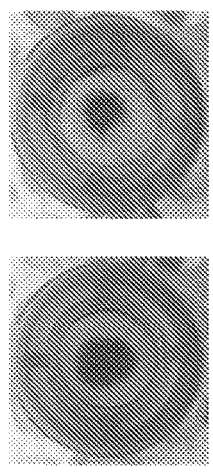
CsgA-MAM
FIG. 2B
Congo Red Staining
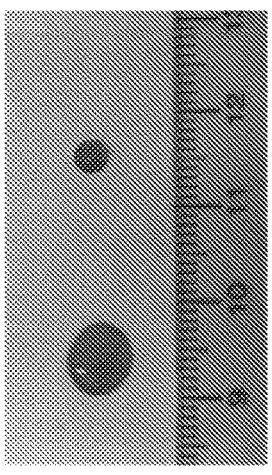
CsgA-TFF2
CsgA-MAM
FIG. 2C
Thioflavin T and DNA staining on filter
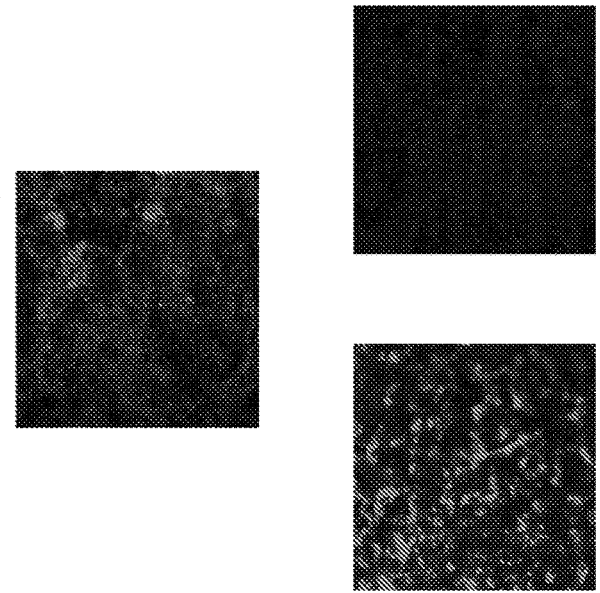

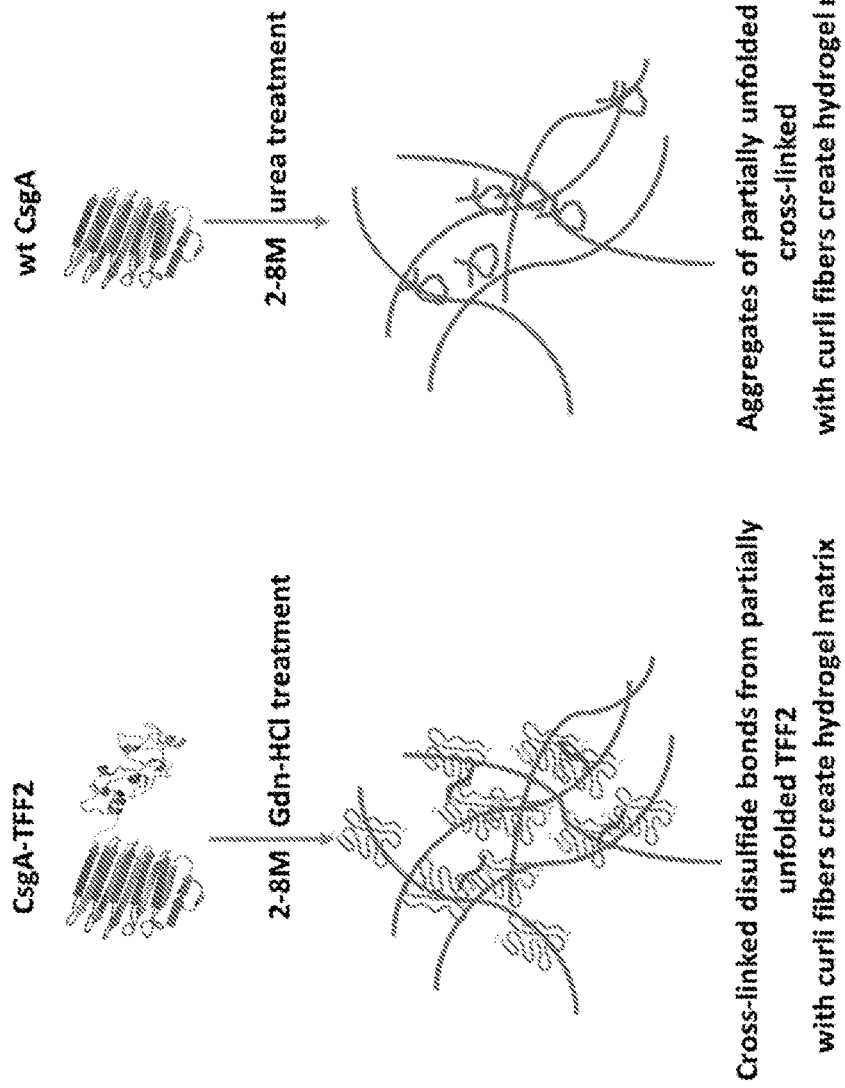
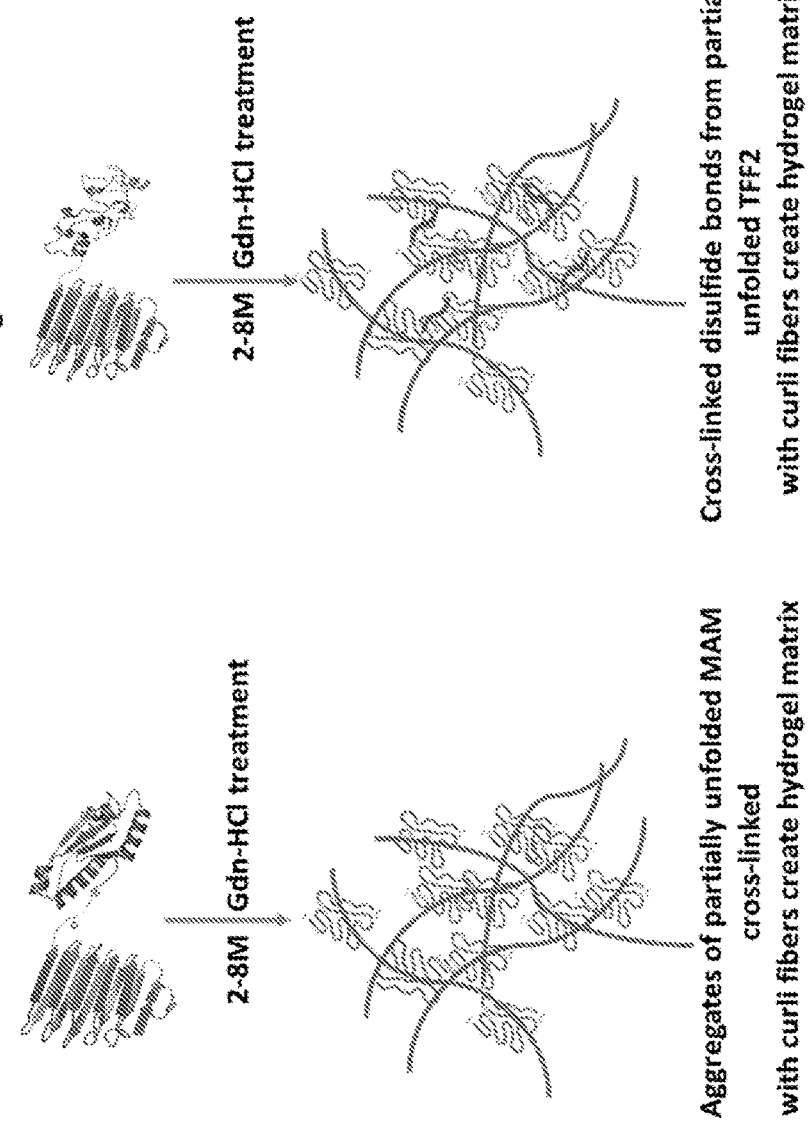

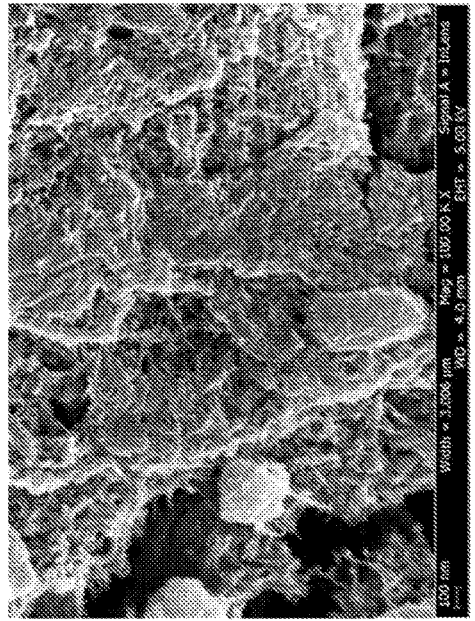
FIG. 7C  Sample of Hydrogel
FIG. 7D
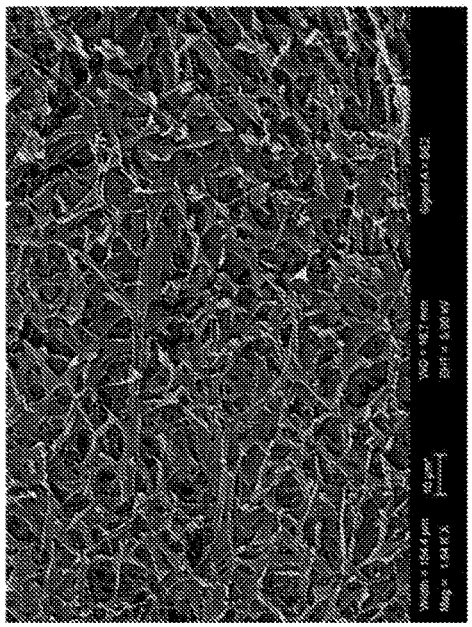
FIG. 7A  Hydrogel on filter
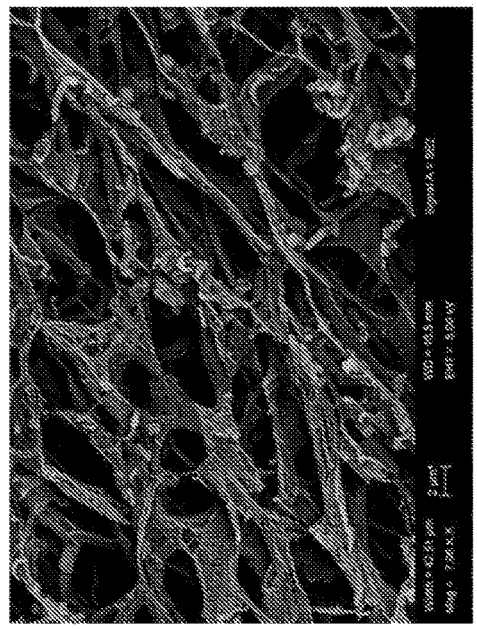
FIG. 7B

FIG. 8B
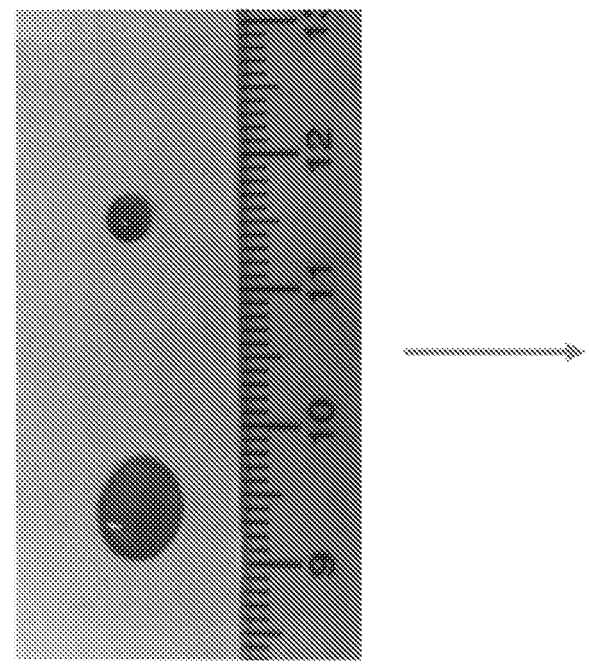
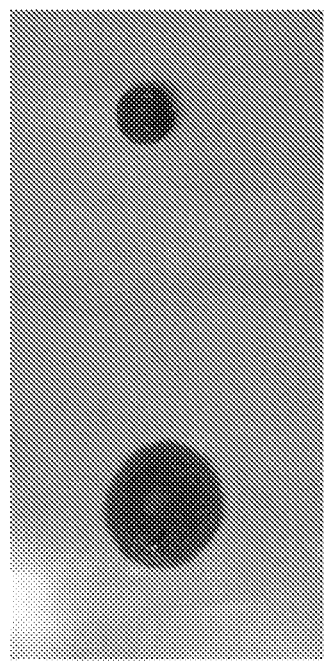
CsgA-TFF2
CsgA-MAM
FIG. 8A
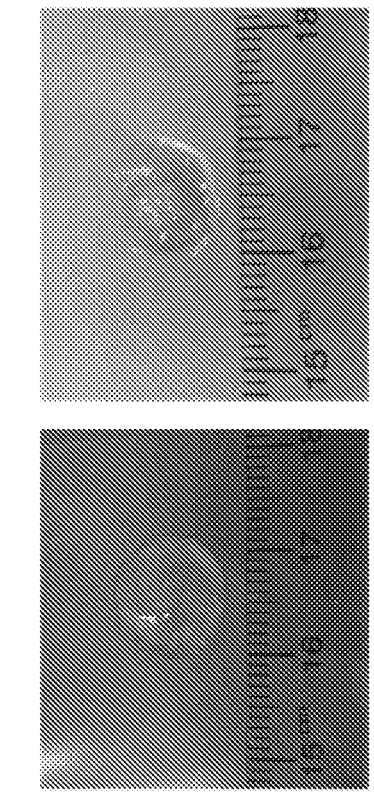
TFF2- curli hydrogel: Air dry at RT for 2-3h Yield ~ 200 mg/L of aerogel or 2.5 ml of hydrogel

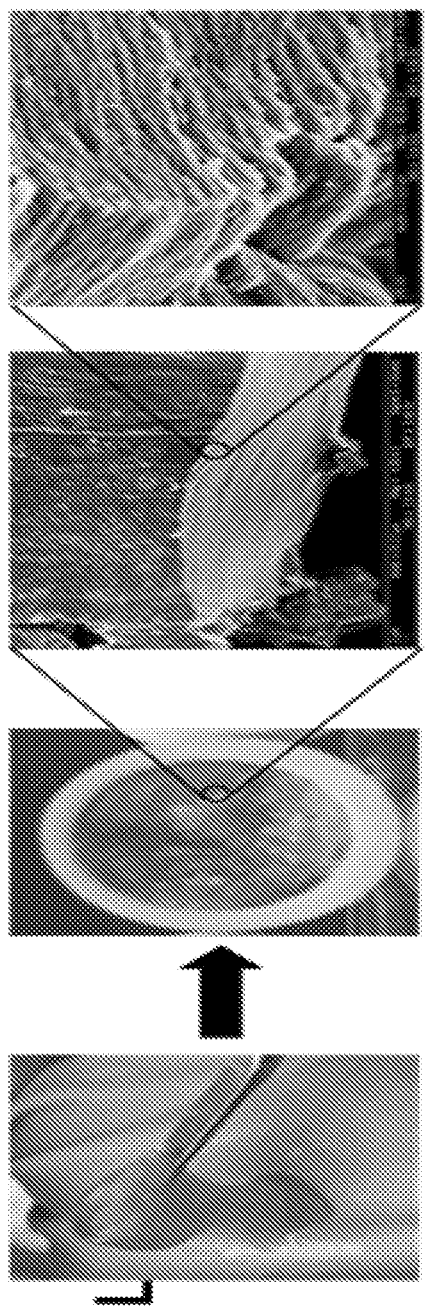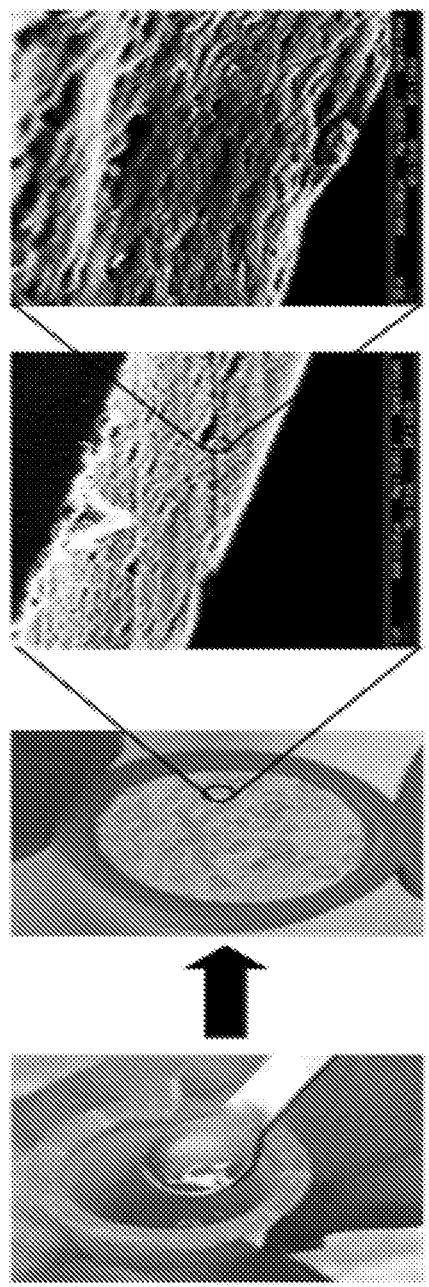
FIG. 24A
FIG. 24B

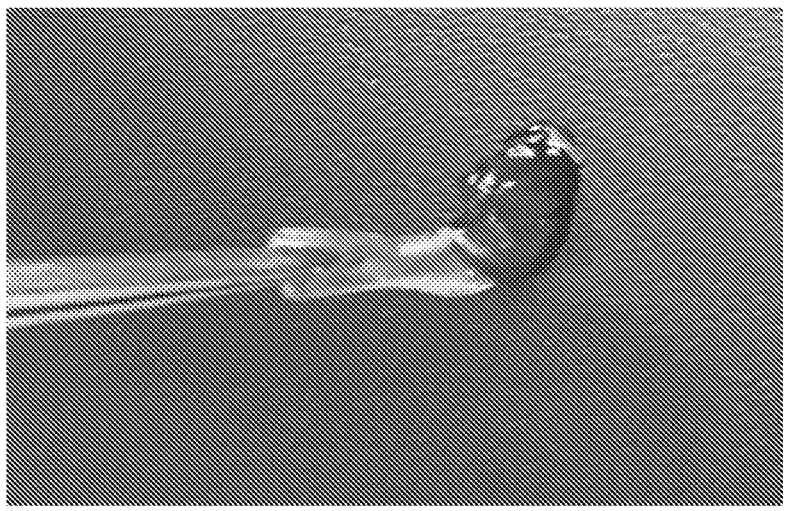
FIG. 25C — SDS only
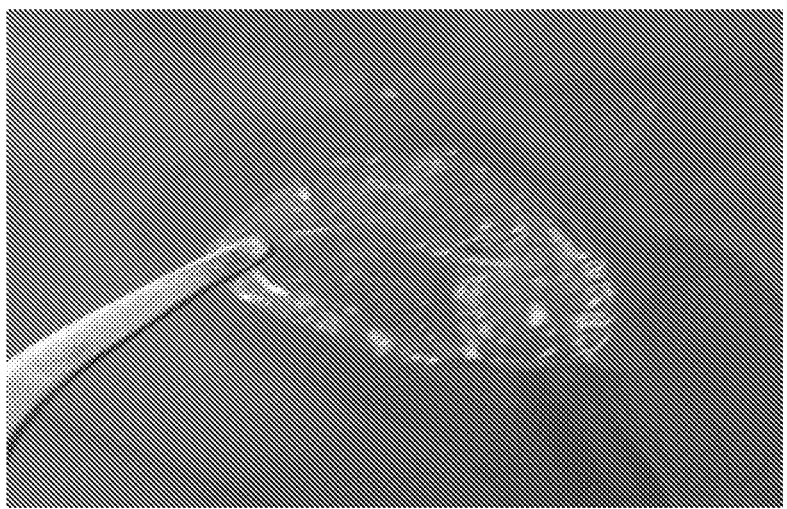
FIG. 25B — GdmCl pre-treatment only and SDS
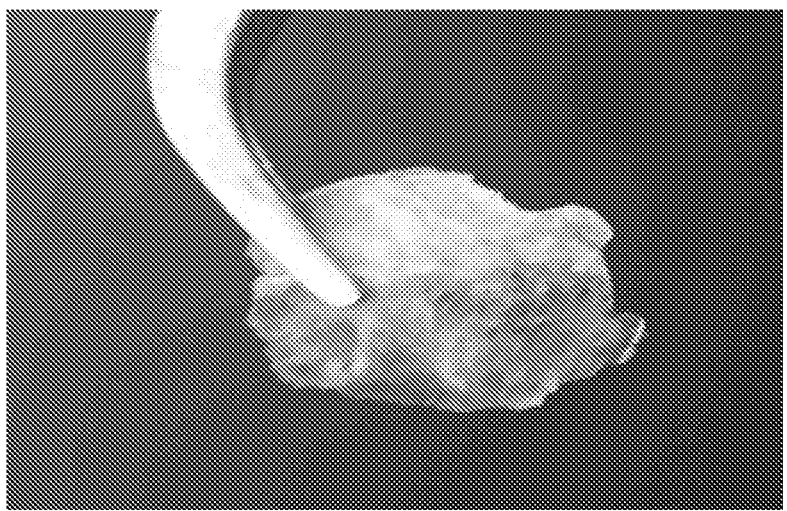
FIG. 25A — GdmCl and SDS

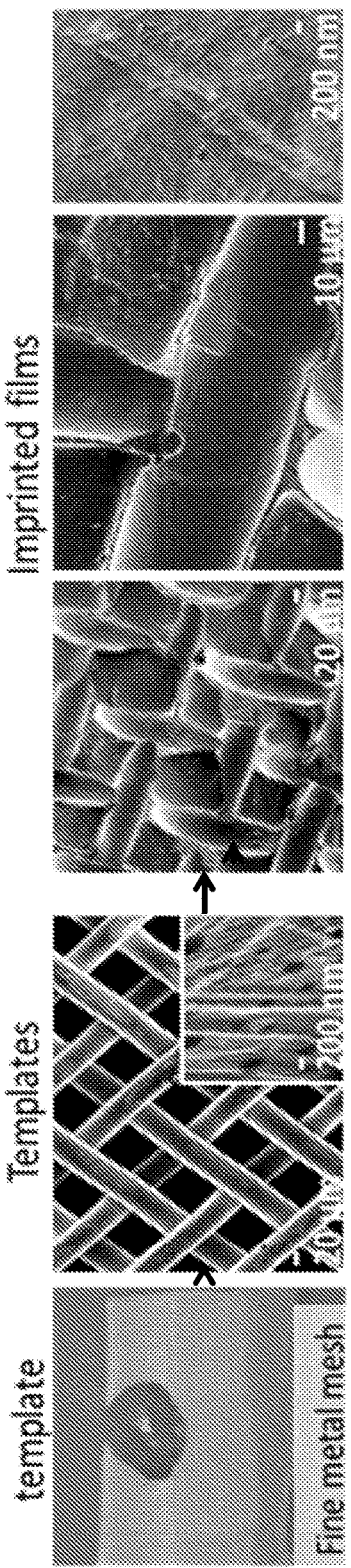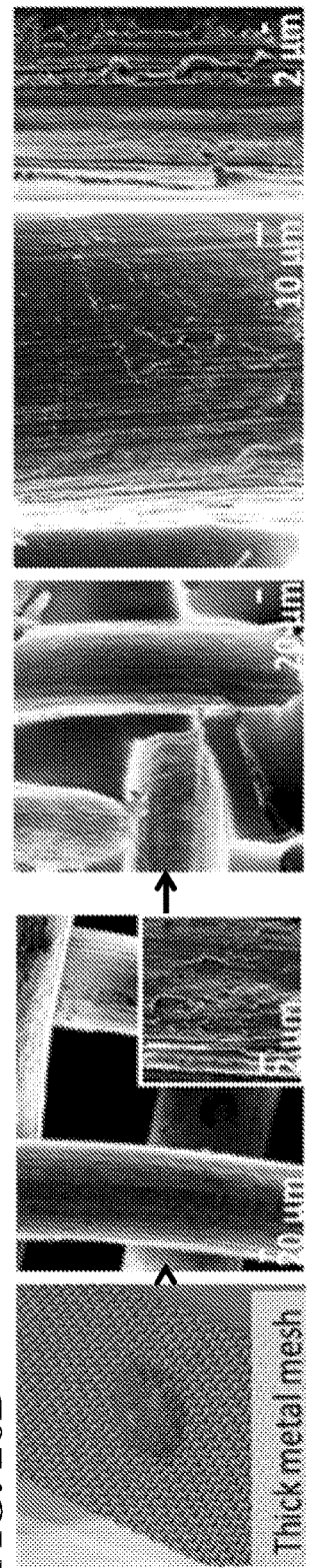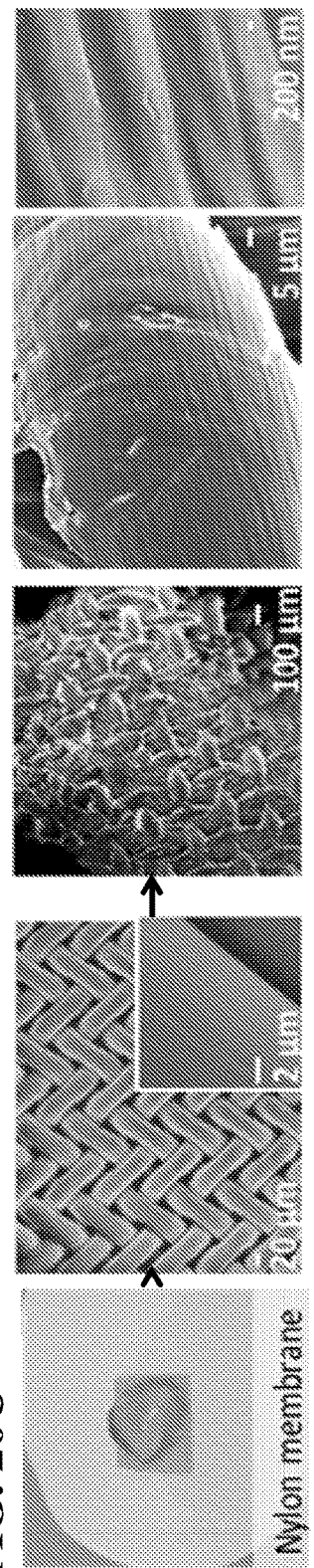
FIG. 26A Gel drying on template — Fine metal mesh
FIG. 26B Thick metal mesh
FIG. 26C Nylon membrane

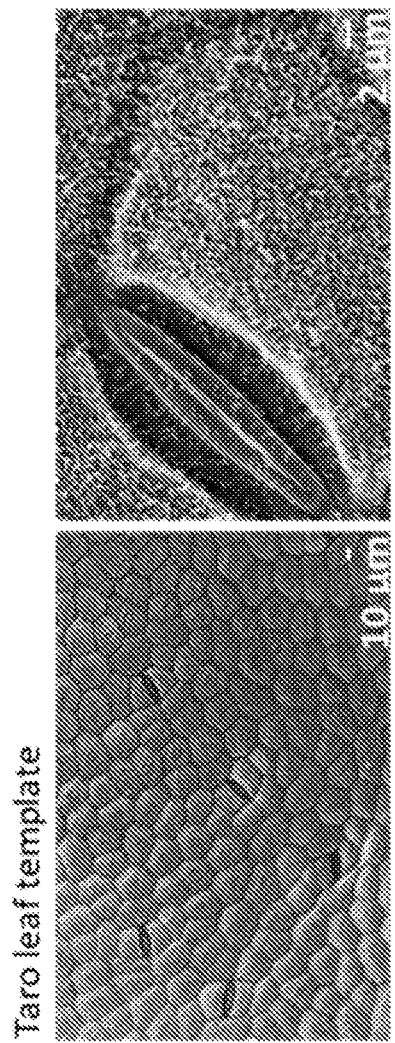
FIG. 27A
Water droplets on hydrophobic Taro leaf
FIG. 27B
Taro leaf template
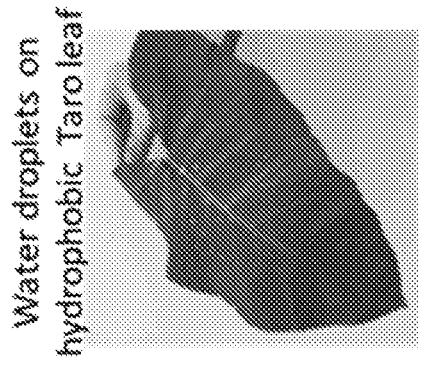
FIG. 27C
Gel drying on hydrophobic Taro leaf
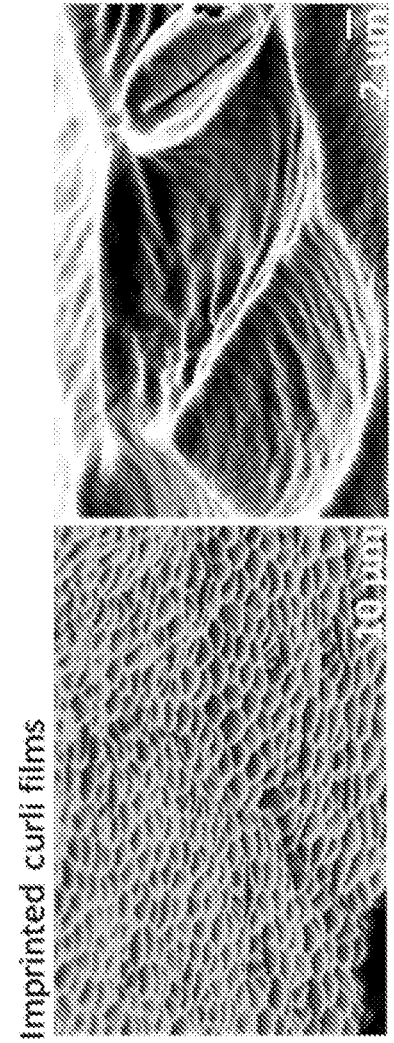
FIG. 27D
Imprinted curli films
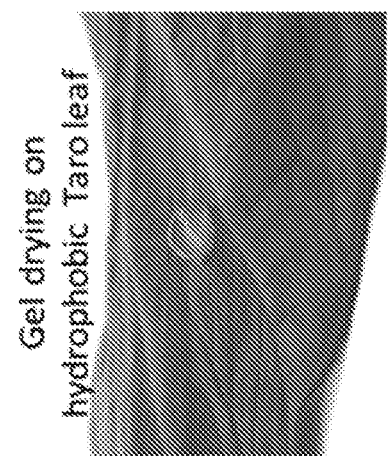

Imprinting on taro leaf
- Resulting curli film is hydrophobic

Imprinting on plastic (flat surface)
- Resulting curli film is hydrophilic and can be re-hydrated

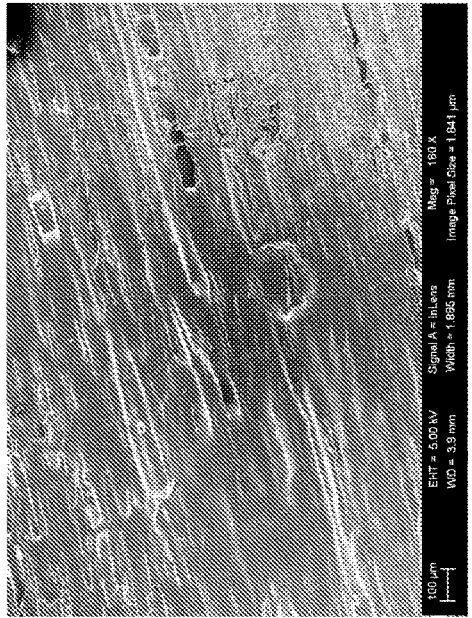
FIG. 31B Wood coated with curli film
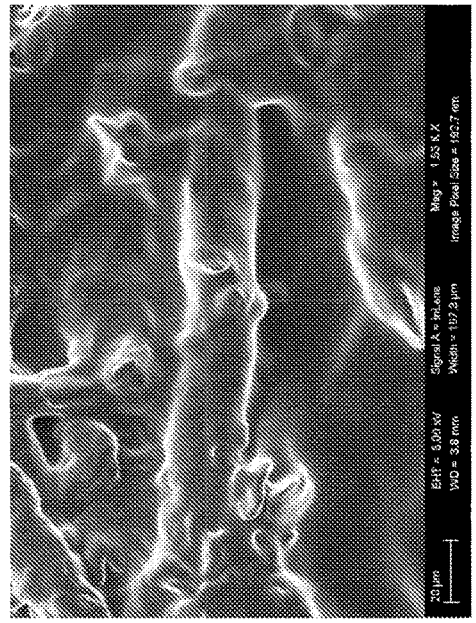
FIG. 31D Paper coated with curli film
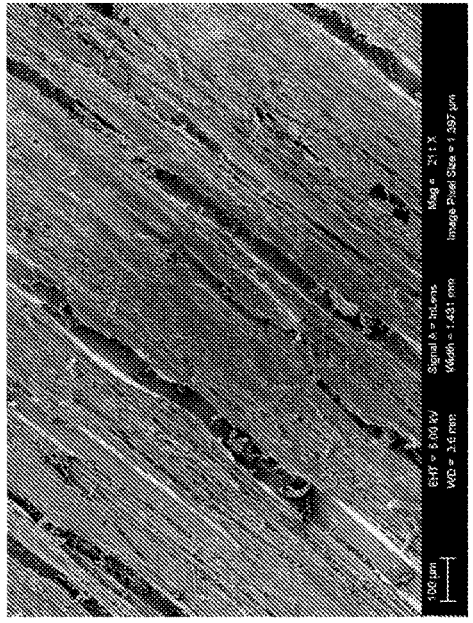
FIG. 31A Wood only
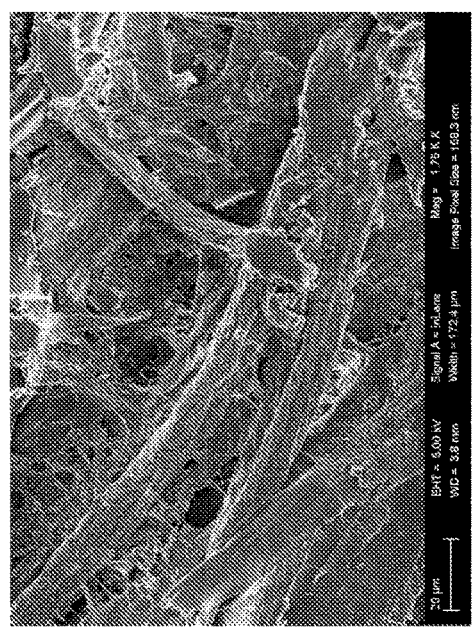
FIG. 31C Paper only Curli film integrated with metal mesh Mesh only Parallel (layered) assembly Interface between two pieces film "glued" interface "glued" interface

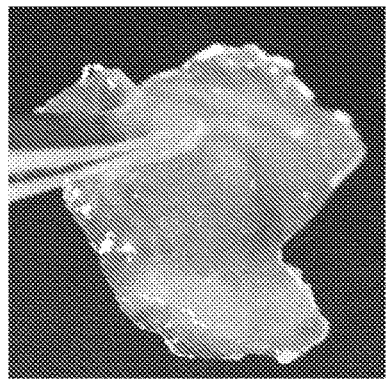
FIG. 34A pH2
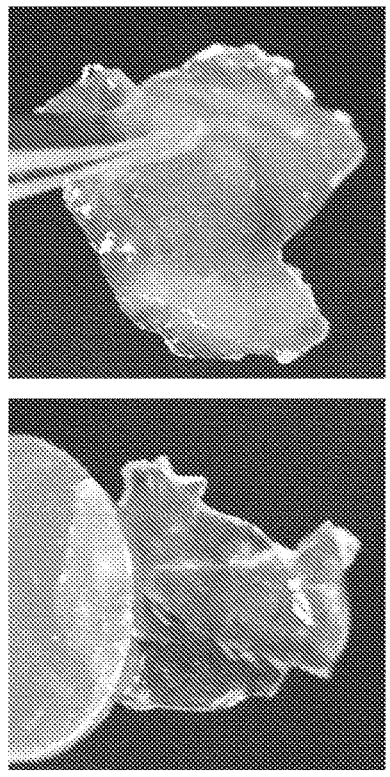
FIG. 34B pH4
FIG. 34C pH7
FIG. 34D pH10
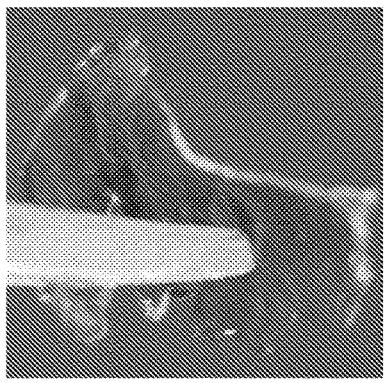
FIG. 34E HFPI
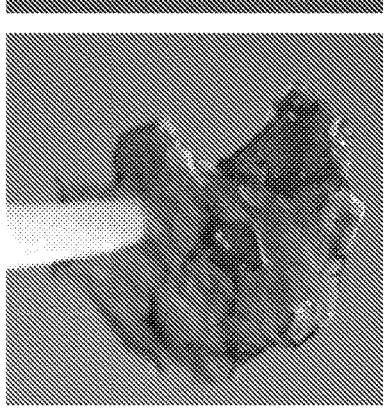
FIG. 34F TFA

```
                        SEQUENCE LISTING

<160> NUMBER OF SEQ ID NOS: 20

<210> SEQ ID NO 1
<211> LENGTH: 151
<212> TYPE: PRT
<213> ORGANISM: Escherichia coli

<400> SEQUENCE: 1

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Asn His
            20                  25                  30

Gly Gly Gly Gly Asn Asn Ser Gly Pro Asn Ser Glu Leu Asn Ile Tyr
        35                  40                  45

Gln Tyr Gly Gly Gly Asn Ser Ala Leu Ala Leu Gln Thr Asp Ala Arg
    50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Gly Asn Gly Ala Ala Val Asp Gln
            115                 120                 125

Thr Ala Ser Asn Ser Ser Val Asn Val Thr Gln Val Gly Phe Gly Asn
        130                 135                 140

Asn Ala Thr Ala His Gln Tyr
145                 150
```

```
<210> SEQ ID NO 2
<211> LENGTH: 60
<212> TYPE: PRT
<213> ORGANISM: Unknown
<220> FEATURE:
<223> OTHER INFORMATION: Description of Unknown:
      Trefoil factor 1 sequence

<400> SEQUENCE: 2

Glu Ala Gln Thr Glu Thr Cys Thr Val Ala Pro Arg Glu Arg Gln Asn
1               5                   10                  15

Cys Gly Phe Pro Gly Val Thr Pro Ser Gln Cys Ala Asn Lys Gly Cys
            20                  25                  30

Cys Phe Asp Asp Thr Val Arg Gly Val Pro Trp Cys Phe Tyr Pro Asn
        35                  40                  45

Thr Ile Asp Val Pro Pro Glu Glu Cys Glu Phe
    50                  55                  60

<210> SEQ ID NO 3
<211> LENGTH: 106
<212> TYPE: PRT
<213> ORGANISM: Unknown
<220> FEATURE:
<223> OTHER INFORMATION: Description of Unknown:
      Trefoil factor 2 sequence

<400> SEQUENCE: 3

Glu Lys Pro Ser Pro Cys Gln Cys Ser Arg Leu Ser Pro His Asn Arg
1               5                   10                  15

Thr Asn Cys Gly Phe Pro Gly Ile Thr Ser Asp Gln Cys Phe Asp Asn
            20                  25                  30

Gly Cys Cys Phe Asp Ser Ser Val Thr Gly Val Pro Trp Cys Phe His
        35                  40                  45

Pro Leu Pro Lys Gln Glu Ser Asp Gln Cys Val Met Glu Val Ser Asp
    50                  55                  60

Arg Arg Asn Cys Gly Tyr Pro Gly Ile Ser Pro Glu Glu Cys Ala Ser
65                  70                  75                  80

Arg Lys Cys Cys Phe Ser Asn Phe Ile Phe Glu Val Pro Trp Cys Phe
                85                  90                  95

Phe Pro Lys Ser Val Glu Asp Cys His Tyr
            100                 105

<210> SEQ ID NO 4
<211> LENGTH: 59
<212> TYPE: PRT
<213> ORGANISM: Unknown
<220> FEATURE:
<223> OTHER INFORMATION: Description of Unknown:
      Trefoil factor 3 sequence

<400> SEQUENCE: 4

Glu Glu Tyr Val Gly Leu Ser Ala Asn Gln Cys Ala Val Pro Ala Lys
1               5                   10                  15

Asp Arg Val Asp Cys Gly Tyr Pro His Val Thr Pro Lys Glu Cys Asn
            20                  25                  30

Asn Arg Gly Cys Cys Phe Asp Ser Arg Ile Pro Gly Val Pro Trp Cys
        35                  40                  45

Phe Lys Pro Leu Gln Glu Ala Glu Cys Thr Phe
    50                  55

<210> SEQ ID NO 5
```

```
<211> LENGTH: 135
<212> TYPE: PRT
<213> ORGANISM: Unknown
<220> FEATURE:
<223> OTHER INFORMATION: Description of Unknown:
      MAM domain sequence

<400> SEQUENCE: 5

Met Met Met Pro Ala Asn Tyr Ser Val Ile Ala Glu Asn Glu Met Thr
1               5                   10                  15

Tyr Val Asn Gly Gly Ala Asn Phe Ile Asp Ala Ile Gly Ala Val Thr
            20                  25                  30

Ala Pro Ile Trp Thr Leu Asp Asn Val Lys Thr Phe Asn Thr Asn Ile
        35                  40                  45

Val Thr Leu Val Gly Asn Thr Phe Leu Gln Ser Thr Ile Asn Arg Thr
    50                  55                  60

Ile Gly Val Leu Phe Ser Gly Asn Thr Thr Trp Lys Glu Val Gly Asn
65                  70                  75                  80

Ile Gly Lys Asn Leu Phe Gly Thr Asn Val Lys Gly Asn Pro Ile Glu
                85                  90                  95

Lys Asn Asn Phe Gly Asp Tyr Ala Met Asn Ala Leu Gly Ile Ala Ala
            100                 105                 110

Ala Val Tyr Asn Leu Gly Val Ala Pro Thr Lys Asn Thr Val Lys Glu
        115                 120                 125

Thr Glu Val Lys Phe Thr Val
    130                 135

<210> SEQ ID NO 6
<211> LENGTH: 330
<212> TYPE: PRT
<213> ORGANISM: Escherichia coli

<400> SEQUENCE: 6

Ala Glu Ile Tyr Asn Lys Asp Gly Asn Lys Leu Asp Val Tyr Gly Lys
1               5                   10                  15

Val Lys Ala Met His Tyr Met Ser Asp Asn Ala Ser Lys Asp Gly Asp
            20                  25                  30

Gln Ser Tyr Ile Arg Phe Gly Phe Lys Gly Glu Thr Gln Ile Asn Asp
        35                  40                  45

Gln Leu Thr Gly Tyr Gly Arg Trp Glu Ala Glu Phe Ala Gly Asn Lys
    50                  55                  60

Ala Glu Ser Asp Thr Ala Gln Gln Lys Thr Arg Leu Ala Phe Ala Gly
65                  70                  75                  80

Leu Lys Tyr Lys Asp Leu Gly Ser Phe Asp Tyr Gly Arg Asn Leu Gly
                85                  90                  95

Ala Leu Tyr Asp Val Glu Ala Trp Thr Asp Met Phe Pro Glu Phe Gly
            100                 105                 110

Gly Asp Ser Ser Ala Gln Thr Asp Asn Phe Met Thr Lys Arg Ala Ser
        115                 120                 125

Gly Leu Ala Thr Tyr Arg Asn Thr Asp Phe Phe Gly Val Ile Asp Gly
    130                 135                 140

Leu Asn Leu Thr Leu Gln Tyr Gln Gly Lys Asn Glu Asn Arg Asp Val
145                 150                 155                 160

Lys Lys Gln Asn Gly Asp Gly Phe Gly Thr Ser Leu Thr Tyr Asp Phe
                165                 170                 175

Gly Gly Ser Asp Phe Ala Ile Ser Gly Ala Tyr Thr Asn Ser Asp Arg
            180                 185                 190
```

```
Thr Asn Glu Gln Asn Leu Gln Ser Arg Gly Thr Gly Lys Arg Ala Glu
            195                 200                 205

Ala Trp Ala Thr Gly Leu Lys Tyr Asp Ala Asn Asn Ile Tyr Leu Ala
210                 215                 220

Thr Phe Tyr Ser Glu Thr Arg Lys Met Thr Pro Ile Thr Gly Gly Phe
225                 230                 235                 240

Ala Asn Lys Thr Gln Asn Phe Glu Ala Val Ala Gln Tyr Gln Phe Asp
            245                 250                 255

Phe Gly Leu Arg Pro Ser Leu Gly Tyr Val Leu Ser Lys Gly Lys Asp
            260                 265                 270

Ile Glu Gly Ile Gly Asp Glu Asp Leu Val Asn Tyr Ile Asp Val Gly
            275                 280                 285

Ala Thr Tyr Tyr Phe Asn Lys Asn Met Ser Ala Phe Val Asp Tyr Lys
290                 295                 300

Ile Asn Gln Leu Asp Ser Asp Asn Lys Leu Asn Ile Asn Asn Asp Asp
305                 310                 315                 320

Ile Val Ala Val Gly Met Thr Tyr Gln Phe
            325                 330

<210> SEQ ID NO 7
<211> LENGTH: 249
<212> TYPE: PRT
<213> ORGANISM: Unknown
<220> FEATURE:
<223> OTHER INFORMATION: Description of Unknown:
      Ribosomal protein S6 sequence

<400> SEQUENCE: 7

Met Lys Leu Asn Ile Ser Phe Pro Ala Thr Gly Cys Gln Lys Leu Ile
1               5                   10                  15

Glu Val Asp Asp Glu Arg Lys Leu Arg Thr Phe Tyr Glu Lys Arg Met
            20                  25                  30

Ala Thr Glu Val Ala Ala Asp Ala Leu Gly Glu Glu Trp Lys Gly Tyr
        35                  40                  45

Val Val Arg Ile Ser Gly Gly Asn Asp Lys Gln Gly Phe Pro Met Lys
50                  55                  60

Gln Gly Val Leu Thr His Gly Arg Val Arg Leu Leu Leu Ser Lys Gly
65                  70                  75                  80

His Ser Cys Tyr Arg Pro Arg Arg Thr Gly Glu Arg Lys Arg Lys Ser
                85                  90                  95

Val Arg Gly Cys Ile Val Asp Ala Asn Leu Ser Val Leu Asn Leu Val
            100                 105                 110

Ile Val Lys Lys Gly Glu Lys Asp Ile Pro Gly Leu Thr Asp Thr Thr
        115                 120                 125

Val Pro Arg Arg Leu Gly Pro Lys Arg Ala Ser Arg Ile Arg Lys Leu
130                 135                 140

Phe Asn Leu Ser Lys Glu Asp Asp Val Arg Gln Tyr Val Val Arg Lys
145                 150                 155                 160

Pro Leu Asn Lys Glu Gly Lys Lys Pro Arg Thr Lys Ala Pro Lys Ile
                165                 170                 175

Gln Arg Leu Val Thr Pro Arg Val Leu Gln His Lys Arg Arg Arg Ile
            180                 185                 190

Ala Leu Lys Lys Gln Arg Thr Lys Lys Asn Lys Glu Glu Ala Ala Glu
        195                 200                 205

Tyr Ala Lys Leu Leu Ala Lys Arg Met Lys Glu Ala Lys Glu Lys Arg
```

```
                210                 215                 220
Gln Glu Gln Ile Ala Lys Arg Arg Leu Ser Ser Leu Arg Ala Ser
225                 230                 235                 240

Thr Ser Lys Ser Glu Ser Ser Gln Lys
                245

<210> SEQ ID NO 8
<211> LENGTH: 119
<212> TYPE: PRT
<213> ORGANISM: Unknown
<220> FEATURE:
<223> OTHER INFORMATION: Description of Unknown:
      Plastocyanin sequence

<400> SEQUENCE: 8

Met Ile Ser Ser Leu Arg Ser Ala Leu Ser Ala Cys Phe Ala Leu Leu
1               5                   10                  15

Leu Val Leu Ala Phe Gly Val Ala Ser Ala Gln Ala Lys Thr Val Glu
            20                  25                  30

Val Lys Leu Gly Thr Asp Ala Gly Met Leu Ala Phe Glu Pro Ser Ser
        35                  40                  45

Val Thr Ile Ser Thr Gly Asp Ser Val Lys Phe Val Asn Asn Lys Leu
    50                  55                  60

Ala Pro His Asn Ala Val Phe Glu Gly His Glu Glu Leu Ser His Pro
65                  70                  75                  80

Asp Leu Ala Phe Ala Pro Gly Glu Ser Trp Gln Glu Thr Phe Thr Glu
                85                  90                  95

Ala Gly Thr Tyr Asp Tyr Tyr Cys Glu Pro His Arg Gly Ala Gly Met
            100                 105                 110

Val Gly Lys Val Val Val Asn
        115

<210> SEQ ID NO 9
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Tyr Lys Asp Asp Asp Asp
1               5

<210> SEQ ID NO 11
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 11

Asp Tyr Lys Asp Asp Asp Lys
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Tyr Lys Asp Asp Asp Lys
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Pro Tyr Asp Val Pro Asp Tyr Ala
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Ala Tyr Asp Val Pro Asp Tyr Ala
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Asp Val Pro Asp Tyr Ala Ser Leu
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Glu Gln Lys Leu Ile Ser Glu Glu Asp Leu
1               5                   10
```

-continued

```
<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 17

His His His His His His
1               5

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Glu Thr Ala Ala Ala Lys Phe Glu Arg Gln His Met Asp Ser
1               5                   10                  15

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Lys Pro Ile Pro Asn Pro Leu Leu Gly Leu Asp Ser Thr
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Ser Gly Gly Ser Gly Gly Ser Gly Gly Ser Gly
1               5                   10
```

METHODS OF MAKING GELS AND FILMS USING CURLI NANOFIBERS

RELATED APPLICATIONS

This application is a 35 U.S.C. § 371 national stage filing of International Application No. PCT/US2017/033579, filed on May 19, 2017, which in turn claims priority to U.S. Provisional Patent Application No. 62/338,835, filed on May 19, 2016. The entire contents of each of the foregoing applications are expressly incorporated herein by reference.

SEQUENCE LISTING

The instant application contains a Sequence Listing which has been filed electronically in ASCII format and is hereby incorporated by reference in its entirety. Said ASCII copy, created on Mar. 25, 2020, is named 117823-13603 SL.txt and is 14,487 bytes in size.

BACKGROUND

The unique self-assembling properties of amyloid proteins make them attractive fibrous materials for a variety of applications. They are highly resistant to harsh environmental conditions and can be used during various stages of assembly (monomeric proteins, oligomers, fiber or large aggregates). There exist several classes of naturally-occurring amyloid proteins in many different species, ranging from humans to bacteria. Of particular interest are curli nanofibers, naturally produced extracellularly by *Escherichia coli* and used to promote bacterial adhesion and biofilm formation. A major hurdle, however, is the large-scale production of genetically engineered amyloid materials.

Curli nanofibers can be used to form gels and films useful in numerous applications. In order to produce curli nanofiber hydrogels, aerogels and free-standing films with beneficial properties, more efficient methods are needed.

SUMMARY

The methods described herein provide a simple and versatile process for making curli nanofiber hydrogels, aerogels and free-standing films at a scale large enough to increase the opportunities for using curli fibers as functional materials. The methods are based on the use of genetically engineered, bacterially derived amyloid-based polypeptides. The methods described herein can be scaled up for the large scale production of curli nanofibers, e.g., genetically engineered curli nanofibers exhibiting a desired function.

The methods of the present disclosure may be used to generate any genetically engineered bacterially derived amyloid-based hydrogel, aerogel or free-standing film, including, but not limited to wild-type curli nanofibers, and curli nanofibers comprising CsgA fusion proteins (e.g., CsgA-TFF2 fusion proteins and CsgA-MAM fusion proteins). In some embodiments, the amyloid fibers can be genetically engineered or can be naturally-occurring (i.e., not genetically engineered). In some embodiments, genetically engineered amyloid fibers contain mutations (e.g., point mutations, random mutations, deletions, insertions, frame shifts). In some embodiments, genetically engineered amyloid fibers are fused or attached to a linker, tag (e.g., a polypeptide or nucleic acid tag), protein, enzyme, catalytic site, metal binding domain, conjugation domain, or other fusion. In exemplary embodiments, curli nanofibers are purified using the methods of the disclosure, e.g., genetically engineered curli nanofibers. Recombinant CsgA polypeptides, curli fibers and biofilms, and methods of producing recombinant CsgA polypeptides, curli fibers and biofilms have been described previously in U.S. Patent Publication No. 2016/0185828 A1, and U.S. Provisional Patent Application Nos. 62/143,560, 62/257,441, 62/336,937, and 62/354,843, the contents of each which are expressly incorporated herein by reference in their entireties.

In some embodiments, the curli nanofibers produced by the methods described herein can be imprinted with micro features and/or nano features. In some embodiments, the curli nanofibers produced as described herein can be used for a variety of purposes, e.g., absorbing agents, (e.g., contaminants, solvents, gases, lightweight structural material), catalysis, filtration, functional paper, water purification, environmental remediation, capture of metals, organic compounds or proteins, sensing (e.g., photoactive, chemically active, fluorescently active), as a therapeutic (e.g., in wound healing, tissue engineering, drug delivery, and implantation to tissue to replace natural mucosa), microfluidic devices, portable sensing, or in bioelectronics (e.g., as electronically conductive fibers).

In one aspect, provided herein is a biologic hydrogel comprising an amyloid, wherein the hydrogel comprises at least 3% (w/w) amyloid. In some embodiments, the hydrogel comprises at least 4% (w/w) amyloid. In some embodiments, the hydrogel comprises at least 5% (w/w) amyloid. In some embodiments, the hydrogel comprises at least 6% (w/w) amyloid. In some embodiments, the hydrogel comprises at least 10% (w/w) amyloid. In some embodiments, the hydrogel comprises between 3% (w/w) and 6% (w/w) amyloid. In some embodiments, the hydrogel comprises between 5% (w/w) and 10% (w/w) amyloid. In some embodiments, the hydrogel comprises between 4% (w/w) and 8% (w/w) amyloid. In some embodiments, the hydrogel comprises between 5% (w/w) and 15% (w/w) amyloid. In some embodiments, the hydrogel comprises between 3% (w/w) and 20% (w/w) amyloid. In some embodiments, the amyloid comprises an amyloid aggregate.

In one aspect, provided herein is a biologic hydrogel comprising a curli fiber, wherein the hydrogel comprises at least 3% (w/w) curli fiber. In some embodiments, the hydrogel comprises at least 4% (w/w) curli fiber. In some embodiments, the hydrogel comprises at least 5% (w/w) curli fiber. In some embodiments, the hydrogel comprises at least 6% (w/w) curli fiber. In some embodiments, the hydrogel comprises at least 10% (w/w) curli fiber. In some embodiments, the hydrogel comprises between 3% (w/w) and 6% (w/w) curli fiber. In some embodiments, the hydrogel comprises between 5% (w/w) and 10% (w/w) curli fiber. In some embodiments, the hydrogel comprises between 4% (w/w) and 8% (w/w) curli fiber. In some embodiments, the hydrogel comprises between 5% (w/w) and 15% (w/w) curli fiber. In some embodiments, the hydrogel comprises between 3% (w/w) and 20% (w/w) curli fiber.

In some embodiments, the biologic hydrogel comprises at least 90% water (w/w) or at least 90% (w/w) other solvent. In some embodiments, the biologic hydrogel comprises at least 85% water (w/w) or at least 85% (w/w) other solvent. In some embodiments, the biologic hydrogel comprises at least 80% water (w/w) or at least 80% (w/w) other solvent. In some embodiments, the biologic hydrogel comprises at least 75% water (w/w) or at least 75% (w/w) other solvent. In some embodiments, the biologic hydrogel comprises at least 70% water (w/w) or at least 70% (w/w) other solvent.

In some embodiments, the curli fiber comprises wild-type CsgA.

In some embodiments, the curli fiber comprises an engineered CsgA fusion protein, and wherein the engineered CsgA fusion protein comprises a CsgA polypeptide fused to an activity polypeptide. In some embodiments, the activity polypeptide is a mucoadhesive polypeptide, a porin, a ribosomal protein or a plastocyanin. In some embodiments, the mucoadhesive polypeptide is selected from the group consisting of: trefoil factor 1 (TFF1), trefoil factor 2 (TFF2), trefoil factor 3 (TFF3), and a MAM domain. In some embodiments, the mucoadhesive polypeptide is TFF2. In some embodiments, the mucoadhesive polypeptide is a MAM domain.

In some embodiments, the activity polypeptide is fused to the C-terminus of the CsgA polypeptide. In some embodiments, the activity polypeptide is fused to the N-terminus of the CsgA polypeptide. In some embodiments, the CsgA fusion protein comprises a linker polypeptide linker sequence adjoining the CsgA polypeptide and the activity polypeptide. In some embodiments, the polypeptide liker sequence is a flexible linker sequence.

In some embodiments, the engineered CsgA fusion protein further comprises a polypeptide tag. In some embodiments, the polypeptide tag is selected from the group consisting of a poly-histidine tag, a myc tag, a FLAG tag, a hemagglutinin (HA) tag, and a V5 tag.

In some embodiments, the biologic hydrogel comprises a cell. In some embodiments, the cell is a bacterial cell, a mammalian cell, a protozoan, or a fungus. In some embodiments, the bacterial cell is a live bacterial cell. In some embodiments, the bacterial cell is a dead bacterial cell. In some embodiments, the bacterial cell is a spore. In some embodiments, the bacterial cell is non-pathogenic. In some embodiments, the bacterial cell is of the species *Escherichia coli*. In some embodiments, the bacterial cell is a wild-type bacterial cell. In some embodiments, the bacterial cell is a genetically-modified bacterial cell. In some embodiments, the bacterial cell comprises a heterologous nucleic acid, which comprises a heterologous gene encoding an engineered CsgA fusion protein comprises a CsgA polypeptide fused to an activity polypeptide. In some embodiments, the bacterial cell comprises a heterologous nucleic acid, which comprises a heterologous gene encoding a polypeptide selected from the group consisting of an extracellular matrix component, a therapeutic polypeptide, a mucoadhesive polypeptide, a cytokine, an enzyme, an antibody, or an antibody mimetic sequence.

In some embodiments, the hydrogel comprises a nucleic acid, an extracellular matrix component, a polysaccharide, a metabolite, a metal ion, a nanoparticle, a polypeptide, cellulose, a vitamin, a nutraceutical, or a detectable compound. In some embodiments, the detectable compound comprises a fluorescent moiety, a radioactive moiety, a colorimetric dye, a fluorescent dye, a luminescent dye, a magnetic resonance imaging (MRI) contrast agent, a CT contrast agent, a PET contrast agent, or an ultrasound contrast agent. In some embodiments, the hydrogel comprises a surfactant. In some embodiments, the surfactant is an anionic surfactant. In some embodiments, the anionic surfactant is sodium dodecyl sulfate (SDS) or sodium lauroyl sarcosinate. In some embodiments, hydrogel comprises less than 30% surfactant. In some embodiments, hydrogel comprises less than 25% surfactant. In some embodiments, hydrogel comprises less than 20% surfactant. In some embodiments, hydrogel comprises less than 15% surfactant. In some embodiments, hydrogel comprises less than 14% surfactant. In some embodiments, hydrogel comprises less than 13% surfactant. In some embodiments, hydrogel comprises less than 12% surfactant. In some embodiments, hydrogel comprises less than 11% surfactant. In some embodiments, hydrogel comprises less than 10% surfactant. In some embodiments, hydrogel comprises less than 9% surfactant. In some embodiments, hydrogel comprises less than 8% surfactant. In some embodiments, hydrogel comprises less than 7% surfactant. In some embodiments, hydrogel comprises less than 6% surfactant. In some embodiments, hydrogel comprises less than 5% surfactant. In some embodiments, hydrogel comprises less than 4% surfactant. In some embodiments, hydrogel comprises less than 3% surfactant. In some embodiments, hydrogel comprises less than 2% surfactant. In some embodiments, hydrogel comprises less than 1% surfactant.

In some embodiments, the biologic hydrogel comprises curli fibers that are crosslinked.

In some embodiments, the hydrogel is dehydrated. In some embodiments, the hydrogel has been rehydrated.

In some embodiments, the biologic hydrogel is suitable for use in an application selected from the group consisting of: biocatalysis, chemical production, filtration, isolation of molecules from an aqueous solution, water filtration, bioremediation, nanoparticle synthesis, nanowire synthesis, display of optically active materials, surface coating, structural reinforcement of an object, and delivery of a therapeutic agent. In some embodiments, the biologic hydrogel is suitable for use as a therapeutic biomaterial, a biological scaffold, a delivery system for therapeutic agents, a biosensor, a biocatalyst, a coating, or an electronically-conductive material.

In some embodiments, the biologic hydrogel is injectable or sprayable.

In some embodiments, the hydrogel has a storage modulus (G') of at least 50 pascal (Pa). In some embodiments, the hydrogel has a storage modulus (G') of at least 75 pascal (Pa). In some embodiments, the hydrogel has a storage modulus (G') of at least 100 pascal (Pa). In some embodiments, the hydrogel has a storage modulus (G') of at least 200 pascal (Pa). In some embodiments, the hydrogel has a storage modulus (G') of at least 300 pascal (Pa). In some embodiments, the hydrogel has a storage modulus (G') of at least 400 pascal (Pa). In some embodiments, the hydrogel has a storage modulus (G') of at least 500 pascal (Pa). In some embodiments, the hydrogel has a storage modulus (G') of at least 1,000 pascal (Pa).

In another aspect, provided herein is a thin film comprising a biologic hydrogel described herein, wherein the biologic hydrogel has been dehydrated. In some embodiments, the film comprises less than 10% (w/w) water. In some embodiments, the film comprises less than 9% (w/w) water. In some embodiments, the film comprises less than 8% (w/w) water. In some embodiments, the film comprises less than 7% (w/w) water. In some embodiments, the film comprises less than 6% (w/w) water. In some embodiments, the film comprises less than 5% (w/w) water. In some embodiments, the film comprises less than 4% (w/w) water. In some embodiments, the film comprises less than 3% (w/w) water. In some embodiments, the film comprises less than 2% (w/w) water. In some embodiments, the film comprises less than 1% (w/w) water. In some embodiments, the film comprises between 2% and 10% (w/w) water. In some embodiments, the film comprises between 3% and 8% (w/w) water. In some embodiments, the film comprises between 2% and 6% (w/w) water.

In some embodiments, the thin film comprises a surface having a pattern. In some embodiments, the thin film is flexible. In some embodiments, the thin film is rigid.

In another aspect, provided herein is a particle comprising a biologic hydrogel described herein. In another aspect, provided herein is a composition comprising a plurality of the particles. In some embodiments, the plurality of particles comprise a size from about 1 nm to 1 µm. In some embodiments, the plurality of particles comprise a size from about 50 nm to 500 nm. In some embodiments, the plurality of particles comprise a size from about 1 nm to 50 nm.

In another aspect, provided herein is an article of manufacture comprising a biologic hydrogel described herein, a thin film described herein, a particle described herein, a composition comprising a plurality of particles described herein, or combinations thereof. In some embodiments, the article is a drug delivery device, a coating, a 3D printed composition, or a patch. In some embodiments, the drug delivery device is a syringe, an autoinjector, a drug delivery patch.

In yet another aspect, provided herein is a pharmaceutical composition comprising a biologic hydrogel described herein, a thin film described herein, or a particle described herein, and a pharmaceutically-acceptable excipient. In some embodiments, the composition is formulated for oral administration to a subject. In some embodiments, the composition is formulated for rectal administration to a subject. In some embodiments, the subject is a mammalian subject. In some embodiments, the mammalian subject is a human subject. In some embodiments, the mammalian subject is a non-human primate. In some embodiments, the mammalian subject is an animal (e.g., a cat, a dog, a rabbit, a mouse, a horse, a donkey, a goat, a cow, or a hamster). In some embodiments, the pharmaceutical composition is formulated as a pill, a capsule, a lozenge, or a suppository.

In another aspect, provided herein is a method for delivering a drug or a diagnostic agent to the mucosa of a subject in need thereof, the method comprising administering to the subject a biologic hydrogel described herein to the subject, wherein the biologic hydrogel comprises a drug or a diagnostic agent, thereby delivering the drug or diagnostic agent to the mucosa of the subject. In some embodiments, the mucosa is present in the gastrointestinal tract of the subject. In some embodiments, the subject is a mammalian subject. In some embodiments, the mammalian subject is a human subject. In some embodiments, the mammalian subject is a non-human primate. In some embodiments, the mammalian subject is an animal (e.g., a cat, a dog, a rabbit, a mouse, a horse, a donkey, a goat, a cow, or a hamster).

In yet another aspect, provided herein is a method of making a biologic hydrogel comprising concentrating a composition comprising a bacterial cell expressing an amyloid; and contacting the concentrated composition with a surfactant, thereby creating a mixture; and incubating the mixture, thereby allowing the mixture to gelate; thereby making the biologic hydrogel.

In another aspect, provided herein is a method of making a biologic hydrogel comprising concentrating a composition comprising a bacterial cell expressing a curli fiber; and contacting the concentrated composition with a surfactant, thereby creating a mixture; and incubating the mixture, thereby allowing the mixture to gelate; thereby making the biologic hydrogel.

In some embodiments, the concentrating step comprises using centrifugation. In some embodiments, the method further comprises concentrating the composition using filtration prior to contacting the composition with the surfactant.

In some embodiments, the method further comprises contacting the composition with a solubilization agent prior to contacting the composition with the surfactant. In some embodiments, the method further comprises contacting the composition with a nuclease. In some embodiments, the nuclease is a DNAse or an RNAse.

In another aspect, provided herein is a method of making a biologic hydrogel comprising contacting a liquid composition comprising a bacterial cell that expresses an amyloid with a solubilization agent, thereby creating a mixture; contacting the mixture with a filter; contacting the mixture with a surfactant; incubating the mixture, thereby allowing the mixture to gelate; and concentrating the mixture using filtration; thereby making the biologic hydrogel.

In yet another aspect, provided herein is a method of making a biologic hydrogel comprising contacting a liquid composition comprising a bacterial cell that expresses a curli fiber with a solubilization agent, thereby creating a mixture; contacting the mixture with a filter; contacting the mixture with a surfactant; incubating the mixture, thereby allowing the mixture to gelate; and concentrating the mixture using filtration; thereby making the biologic hydrogel.

In some embodiments, the solubilization agent is selected from the group consisting of guanidine hydrochloride, urea, dimethyl sulfoxide (DMSO), beta-mercaptoethanol, and n-propanol. In some embodiments, the solubilization agent is guanidine hydrochloride.

In some embodiments, the guanidine hydrochloride is present in a solution at about 0.5 M to about 10 M. In some embodiments, the guanidine hydrochloride is present in a solution at about 0.8 M. In some embodiments, the guanidine hydrochloride is present in a solution at about 8 M.

In some embodiments, the filtration is performed using vacuum filtration. In some embodiments, the method further comprises removing liquid from the biologic hydrogel by subjecting the biologic hydrogel to filtration, centrifugation, air-drying, evaporation, vacuum, desiccation, sedimentation by gravity, or combinations thereof. In some embodiments, the air-drying is performed at room temperature for at least 2 hours.

In some embodiments, the surfactant is an anionic surfactant. In some embodiments, the anionic surfactant is sodium dodecyl sulfate (SDS) or sodium lauroyl sarcosinate.

In some embodiments, the method further comprises subjecting the biologic hydrogel to solvent exchange. In some embodiments, the solvent exchange is performed using a low tension solvent.

In some embodiments, the method further comprises lyophilizing the biologic hydrogel. In some embodiments, the method further comprises rehydrating the biologic hydrogel.

In some embodiments, the method further comprises imprinting the surface of the biologic hydrogel with a mold. In some embodiments, the mold is a nano mold. In some embodiments, the mold is a micro mold. In some embodiments, the mold comprises a pattern.

In some embodiments, the biologic hydrogel comprises at least 3% (w/w) amyloid. In some embodiments, the biologic hydrogel comprises at least 4% (w/w) amyloid. In some embodiments, the hydrogel comprises at least 5% (w/w) amyloid. In some embodiments, the hydrogel comprises at least 6% (w/w) amyloid. In some embodiments, the hydrogel comprises at least 10% (w/w) amyloid. In some embodiments, the hydrogel comprises between 3% (w/w) and 6% (w/w) amyloid. In some embodiments, the hydrogel comprises between 5% (w/w) and 10% (w/w) amyloid. In some embodiments, the hydrogel comprises between 4% (w/w) and 8% (w/w) amyloid. In some embodiments, the hydrogel comprises between 5% (w/w) and 15% (w/w) amyloid. In some embodiments, the hydrogel comprises between 3% (w/w) and 20% (w/w) amyloid. In some embodiments, the amyloid comprises an amyloid aggregate.

In some embodiments, the biologic hydrogel comprises at least 3% (w/w) curli fiber. In some embodiments, the hydrogel comprises at least 4% (w/w) curli fiber. In some embodiments, the hydrogel comprises at least 5% (w/w) curli fiber. In some embodiments, the hydrogel comprises at least 6% (w/w) curli fiber. In some embodiments, the hydrogel comprises at least 10% (w/w) curli fiber. In some embodiments, the hydrogel comprises between 3% (w/w) and 6% (w/w) curli fiber. In some embodiments, the hydrogel comprises between 5% (w/w) and 10% (w/w) curli fiber. In some embodiments, the hydrogel comprises between 4% (w/w) and 8% (w/w) curli fiber. In some embodiments, the hydrogel comprises between 5% (w/w) and 15% (w/w) curli fiber. In some embodiments, the hydrogel comprises between 3% (w/w) and 20% (w/w) curli fiber.

In some embodiments, the biologic hydrogel comprises at least 90% water (w/w) or at least 90% (w/w) other solvent. In some embodiments, the biologic hydrogel comprises at least 85% water (w/w) or at least 85% (w/w) other solvent. In some embodiments, the biologic hydrogel comprises at least 80% water (w/w) or at least 80% (w/w) other solvent. In some embodiments, the biologic hydrogel comprises at least 75% water (w/w) or at least 75% (w/w) other solvent. In some embodiments, the biologic hydrogel comprises at least 70% water (w/w) or at least 70% (w/w) other solvent.

In some embodiments, the curli fiber comprises wild-type amyloid protein or an engineered amyloid protein. In some embodiments, the curli fiber comprises an engineered CsgA fusion protein, and wherein the engineered CsgA fusion protein comprises a CsgA polypeptide fused to an activity polypeptide. In some embodiments, the activity polypeptide is a mucoadhesive polypeptide, a porin, a ribosomal protein, or a plastocyanin. In some embodiments, the mucoadhesive polypeptide is selected from the group consisting of: trefoil factor 1 (TFF1), trefoil factor 2 (TFF2), trefoil factor 3 (TFF3), and a MAM domain. In some embodiments, the mucoadhesive polypeptide is TFF2. In some embodiments, the mucoadhesive polypeptide is a MAM domain. In some embodiments, the activity polypeptide is fused to the C-terminus of the CsgA polypeptide. In some embodiments, the activity polypeptide is fused to the N-terminus of the CsgA polypeptide. In some embodiments, the CsgA fusion protein comprises a linker polypeptide linker sequence adjoining the CsgA polypeptide and the activity polypeptide. In some embodiments, the polypeptide liker sequence is a flexible linker sequence. In some embodiments, the engineered CsgA fusion protein further comprises a polypeptide tag. In some embodiments, the polypeptide tag is selected from the group consisting of a poly-histidine tag, a myc tag, a FLAG tag, a hemagglutinin (HA) tag, and a V5 tag.

In some embodiments, the bacterial cell is of the species *Escherichia coli*. In some embodiments, the bacterial cell is a wild-type bacterial cell. In some embodiments, the bacterial cell is a genetically-modified bacterial cell.

In another aspect, provided herein is a biologic hydrogel produced using a method described herein.

In yet another aspect, provided herein is a method of producing a multilayered composition comprising a thin film, the method comprising overlaying the surface of a porous substrate with a biologic hydrogel comprising a curli fiber, wherein the hydrogel comprises at least 3% (w/w) curli fiber, drying the biologic hydrogel, thereby producing the multilayered composition comprising the thin film. In some embodiments, the porous substrate comprises wood, a metal mesh, paper, nylon, or combinations thereof. In yet another aspect, provided herein is a multilayered composition produced using this method.

In one aspect, provided herein is a method of making a biologic hydrogel comprising contacting a composition comprising a bacterial cell expressing an amyloid (e.g., a curli fiber) with a surfactant, thereby creating a mixture; and incubating the mixture, thereby allowing the mixture to gelate; thereby making the biologic hydrogel. In some embodiments, the method further comprises concentrating the composition using centrifugation prior to contacting the composition with the surfactant.

In one aspect, provided herein is a method of making a curli nanofiber hydrogel comprising incubating a composition comprising a curli nanofiber with guanidine HCl; incubating the composition with a nuclease; incubating the composition with a surfactant; contacting a composition comprising the curli nanofiber with a filter membrane; washing the filter membrane; and removing the curli nanofiber hydrogel from the filter membrane thereby making the curli nanofiber hydrogel.

In some embodiments, the surfactant is an anionic surfactant. In some embodiments, the anionic surfactant is SDS.

In some embodiments, the curli nanofiber is a CsgA polypeptide.

In some embodiments, the curli nanofiber is a modified curli nanofiber comprising a C-terminal CsgA fusion protein. In some embodiments, the C-terminal CsgA fusion protein is selected from the group consisting of a CsgA-TFF2 fusion protein and a CsgA-MAM fusion protein.

In some embodiments, the curli nanofiber is a modified curli nanofiber comprising a N-terminal CsgA fusion protein. In some embodiments, the N-terminal CsgA fusion protein is selected from the group consisting of a CsgA-TFF2 fusion protein and a CsgA-MAM fusion protein.

In some embodiments, the composition comprising a curli nanofiber is incubated with 0.8 M guanidine HCl for one hour and subsequently incubated with 8M guanidine HCl for five minutes.

In another aspect, provided herein is a curli nanofiber hydrogel produced using a method comprising incubating a composition comprising a curli nanofiber with guanidine HCl; incubating the composition with a nuclease; incubating the composition with a surfactant; contacting a composition comprising the curli nanofiber with a filter membrane; washing the filter membrane; and removing the curli nanofiber hydrogel from the filter membrane thereby making the curli nanofiber hydrogel.

In yet another aspect, provided herein is a method of making a curli nanofiber aerogel comprising incubating a composition comprising a curli nanofiber with guanidine HCl; incubating the composition with a nuclease; incubating the composition with a surfactant; contacting a composition comprising the curli nanofiber with a filter membrane; washing the filter membrane; removing the curli nanofiber hydrogel from the filter membrane; and lyophilizing the curli nanofiber hydrogel, thereby making the curli nanofiber aerogel.

In some embodiments, the lyophilizing comprises a slow evaporation after solvent exchange in a low tension solvent.

In yet another aspect, provided herein is a method of making a curli nanofiber film comprising incubating a composition comprising a curli nanofiber with guanidine HCl; incubating the composition with a nuclease; incubating the composition with a surfactant; contacting a composition comprising the curli nanofiber with a filter membrane;

washing the filter membrane; removing the curli nanofiber hydrogel from the filter membrane; and drying the curli nanofiber hydrogel, thereby making the curli nanofiber film. In some embodiments, the hydrogel is dried over a substrate or support. In some embodiments, the substrate or support is porous or comprise a porous surface. In some embodiments, the substrate or support comprises wood, paper, cloth, textile, or a metal mesh (e.g., a fine metal mesh).

In some embodiments, the drying is at room temperature for at least two hours.

In another aspect, provided herein is a method of making an amyloid-based composite material comprising incubating a composition comprising a curli nanofiber with guanidine HCl; incubating the composition with a nuclease; incubating the composition with a surfactant; contacting a composition comprising the curli nanofiber with a filter membrane; washing the filter membrane; removing the curli nanofiber hydrogel from the filter membrane; drying the curli nanofiber hydrogel to make a curli nanofiber film; and imprinting a micro and nano mold on the curli nanofiber film, thereby making the amyloid-based composite material.

In another aspect, provided herein is a curli nanofiber aerogel produced using a method provided herein.

In another aspect, provided herein is an engineered bacterial cell comprising a heterologous nucleic acid encoding an engineered CsgA fusion protein, wherein the engineered CsgA fusion protein comprises a CsgA polypeptide fused to a mucoadhesive polypeptide. In some embodiments, the mucoadhesive polypeptide is selected from the group consisting of: trefoil factor 1 (TFF1), trefoil factor 2 (TFF2), trefoil factor 3 (TFF3), and a MAM domain. In some embodiments, the mucoadhesive polypeptide is TFF2. In some embodiments, the mucoadhesive polypeptide is a MAM domain. In some embodiments, the mucoadhesive polypeptide is fused to the C-terminus of the CsgA polypeptide. In some embodiments, the mucoadhesive polypeptide is fused to the N-terminus of the CsgA polypeptide. In some embodiments, the CsgA fusion protein comprises a linker polypeptide linker sequence adjoining the CsgA polypeptide and the mucoadhesive polypeptide. In some embodiments, the polypeptide liker sequence is a flexible linker sequence. In some embodiments, the engineered CsgA fusion protein further comprises a polypeptide tag. In some embodiments, the polypeptide tag is selected from the group consisting of a poly-histidine tag, a myc tag, a FLAG tag, a hemagglutinin (HA) tag, and a V5 tag. In some embodiments, the engineered bacterial cell is non-pathogenic. In some embodiments, the engineered bacterial cell is of the species *Escherichia coli*.

BRIEF DESCRIPTION OF THE FIGURES

The foregoing and other features and advantages of the present embodiments will be more fully understood from the following detailed description of illustrative embodiments taken in conjunction with the accompanying drawings in which:

FIGS. 1A and B depict certain proteins for use in CsgA fusion proteins used in making curli nanofibers hydrogels, aerogels and films. FIG. 1A depicts the anti-inflammatory cytokine TFF2.

FIG. 1B depicts the microbial anti-inflammatory molecule MAM.

FIGS. 2A, 2B and 2C show staining of curli nanofiber hydrogels. FIG. 2A depicts images of tubes containing the curli nanofiber hydrogels comprising either CsgA-MAM or Csga-TFF2, as indicated. FIG. 2B depicts the Congo Red staining of curli nanofiber hydrogels demonstrating the presence of the curli fibers, CsgA-MAM and CsgA-TFF2. FIG. 2C depicts the Thioflavin T staining of curli nanofiber hydrogels in the absence (left, bottom panel of FIG. 2B) and presence (right, bottom panel of FIG. 2B) of DNase, demonstrating the presence of the curli fibers.

FIGS. 6A, 6B and 6C depict schemes for the formation of curli nanofiber hydrogels. FIG. 6A depicts the formation of CsgA-MAM-based curli nanofiber matrix in the presence of 2-8M guanidine HCl. FIG. 6B depicts the formation of CsgA-TFF2-based curli nanofiber matrix in the presence of 2-8M guanidine HCl. FIG. 6C depicts the formation of wt-CsgA-based curli nanofiber matrix in the presence of 2-8M urea.

FIGS. 7A, 7B, 7C, and 7D depict the morphology of curli nanofiber hydrogels. FIGS. 7A and 7B depict the morphology of a curli nanofiber hydrogel on a filter as observed by scanning electron microscopy (SEM). FIGS. 7C and 7D depict the morphology of a curli nanofiber hydrogel sample as observed by SEM.

FIGS. 8A and 8B depict curli nanofiber films. FIG. 8A depicts a CsgA-TFF2-based curli nanofiber hydrogel before and after air drying the hydrogel at room temperature for 2-3 hours. FIG. 8B depicts a CsgA-MAM-based curli nanofiber hydrogel and a CsgA-TFF2-based curli nanofiber hydrogel stained with Congo Red before and after air drying the hydrogels.

0M GdmCl"); no pretreatment, followed by treatment with 0.8 M guanidine hydrochloride ("0M/8M GdmCl"); pretreatment with 0.8 M guanidine hydrochloride, followed by no treatment ("0.8M/0M GdmCl"); pretreatment/treatment with 0.8 M and 2 M, respectively of guanidine hydrochloride ("0.8M/2M GdmCl"); pretreatment/treatment with 0.8 M and 4 M, respectively of guanidine hydrochloride ("0.8M/4M GdmCl"); pretreatment/treatment with 0.8 M and 8 M, respectively of guanidine hydrochloride ("0.8M/8M GdmCl"); pretreatment/treatment with 0.8 M and 8 M, respectively of urea ("0.8M/8M Urea"); pretreatment/treatment with 0.5% and 5%, respectively of DMSO ("0.5%/5% DMSO"); and pretreatment/treatment with 0.5% and 5%, respectively of SDS ("0.5%/5% SDS").

Figure 15A:
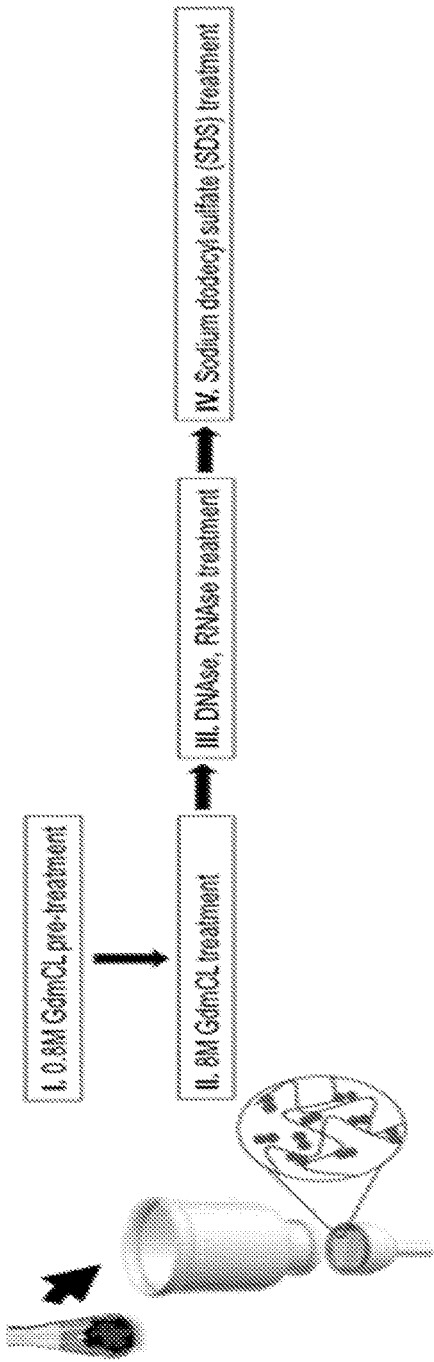
FIG. 15A depicts an exemplary schema for producing a biologic hydrogel using a filtration method, including Steps I and II (pre-treatment and treatment with guanidine hydrochloride at 0.8 M and 8 M, respectively, to cause bacterial lysis); Step III (treatment with DNAse and/or RNAse to remove DNA and RNA, respectively); and Step IV (treatment with sodium dodecyl sulfate (SDS)).
Figure 15B:
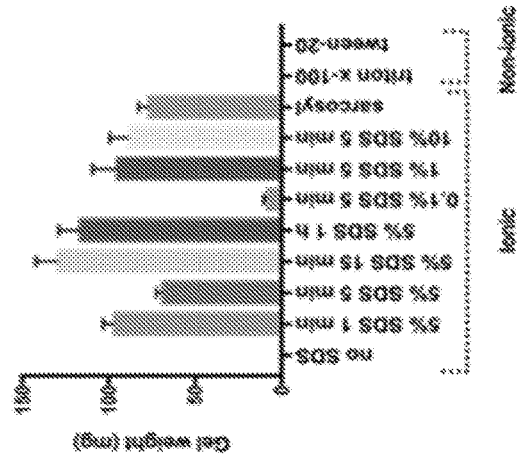
FIG. 15B depicts a bar graph showing the effect on the weight of the formed biologic hydrogel after either: no pretreatment/treatment with guanidine hydrochloride ("0M/
Figure 15C:
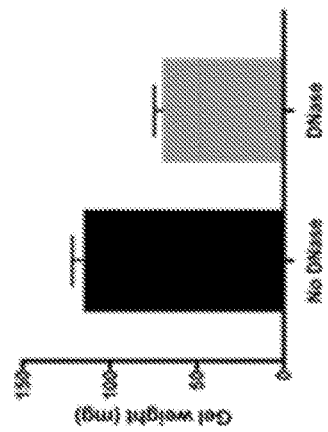

FIG. 15C depicts a bar graph showing the weight of the formed biologic hydrogel after treatment with DNAse ("DNase") or no treatment with DNAse ("No DNase").

Figure 15D:
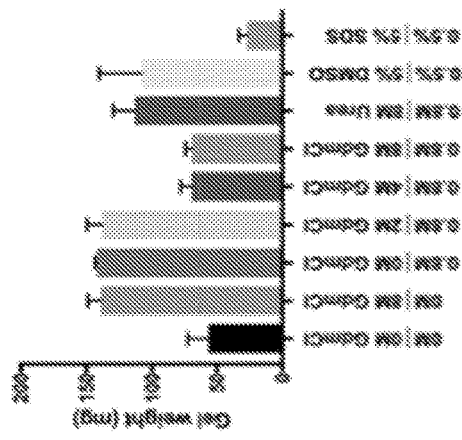

FIG. 15D depicts a bar graph showing the effect on the weight of the formed biologic hydrogel after treatment with either: no SDS, 5% SDS during 1 minute, 5% SDS during 5 minutes, 5% SDS during 15 minutes, 5% SDS during 1 hour, 0.1% SDS during 5 minutes, 1% SDS during 5 minutes, 10% SDS during 5 minutes, sarcosyl (also known as sodium lauroyl sarcosinate), Triton X-100, or Tween 20.

Figure 16B:
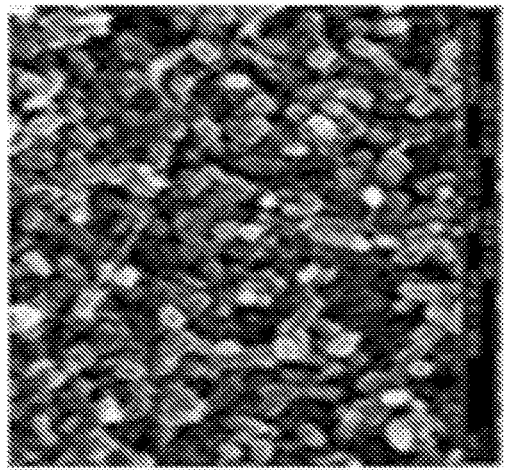
Figure 16D:
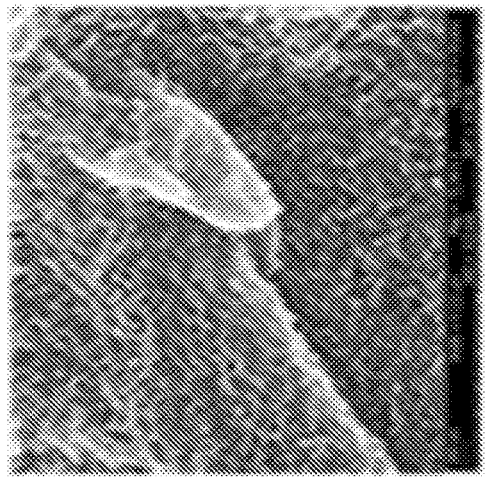
Figure 16A:
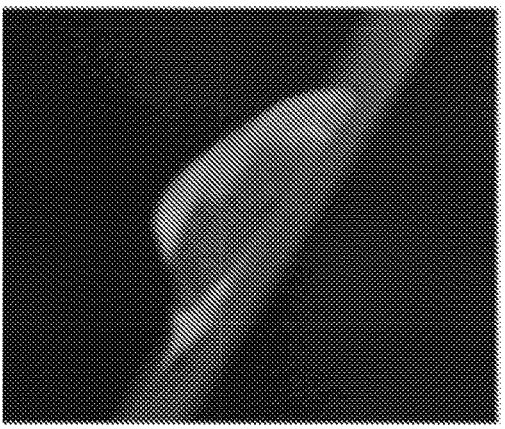
Figure 16C:
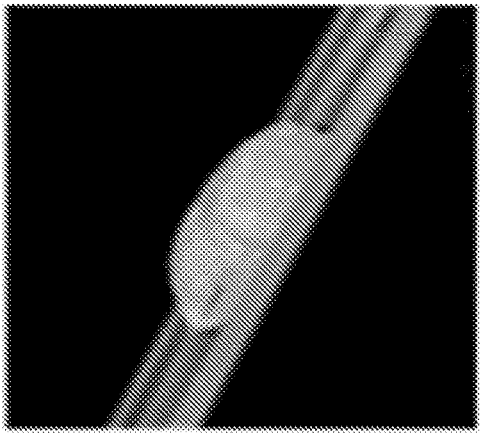

FIG. 16A is a photograph of a biologic hydrogel comprising bacterial cells (also referred to herein as a "live hydrogel"). FIG. 16B depicts an SEM image of the morphology of a biologic hydrogel comprising bacterial cells. FIG. 16C is a photograph of a bacteria-free biologic hydrogel. FIG. 16D depicts an SEM image of the morphology of a bacteria-free biologic hydrogel.

Figure 17E:
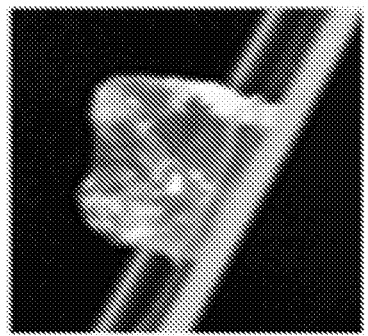
Figure 17F:
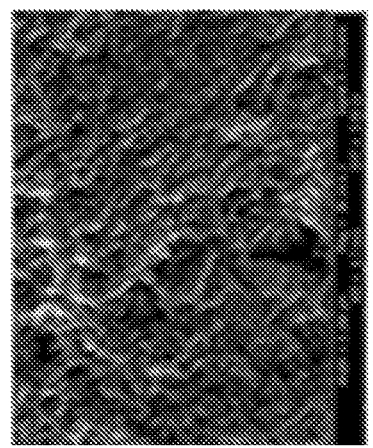
Figure 17C:
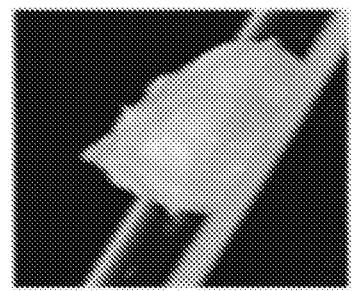
Figure 17D:
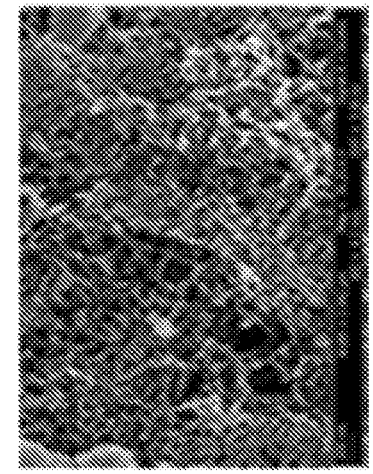
Figure 17A:
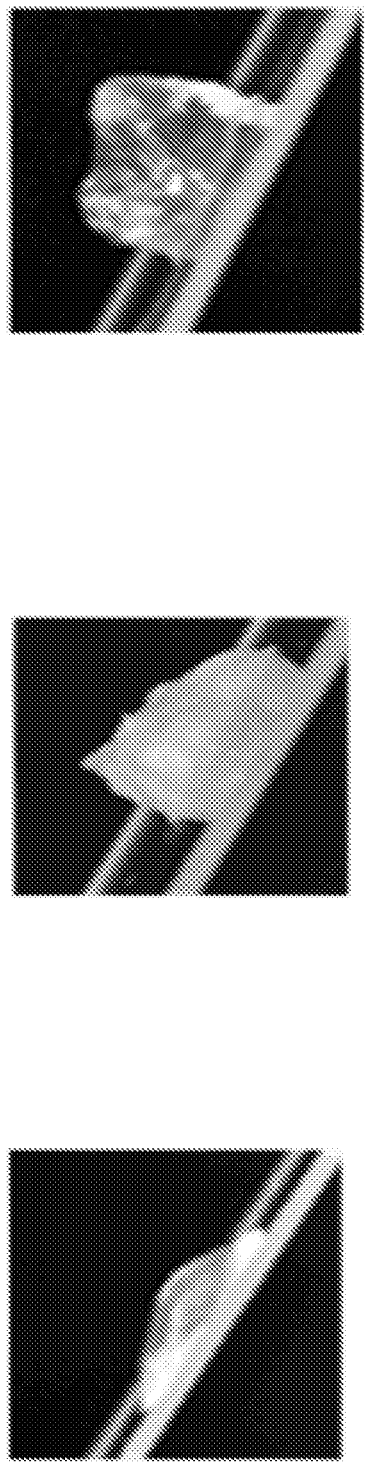
Figure 17B:
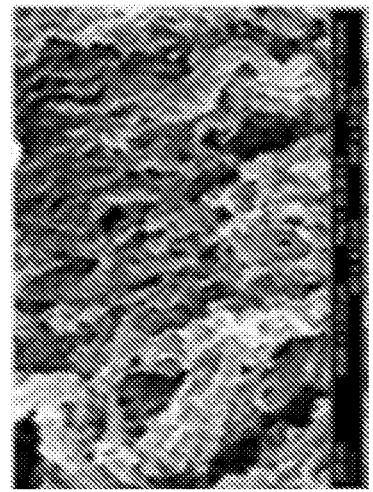

FIGS. 17A and 17B, respectively, are a photograph of a biologic hydrogel comprising curli fiber comprising CsgA-TTF1 and a SEM image depicting the morphology of the biologic hydrogel. FIGS. 17C and 17D, respectively, are a photograph of a biologic hydrogel comprising curli fiber comprising CsgA-TTF2 and a SEM image depicting the morphology of the biologic hydrogel. FIGS. 17E and 17F, respectively, are a photograph of a biologic hydrogel comprising curli fiber comprising CsgA-TTF3 and a SEM image depicting the morphology of the biologic hydrogel.

Figure 18A:
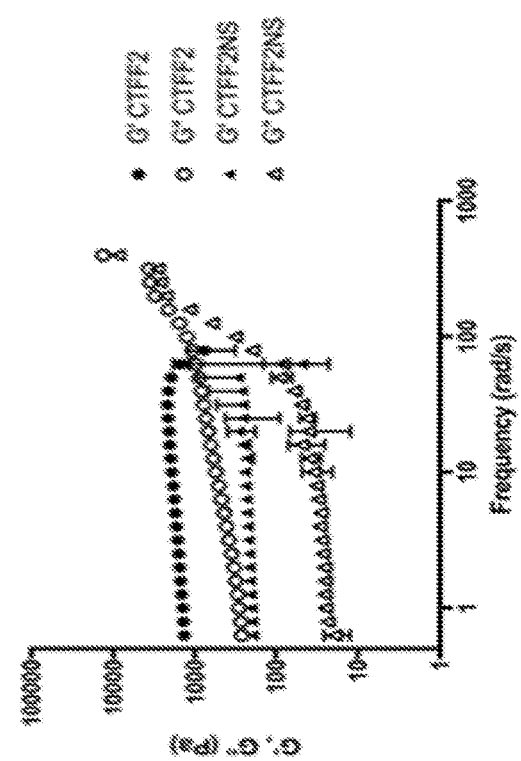
Figure 18C:
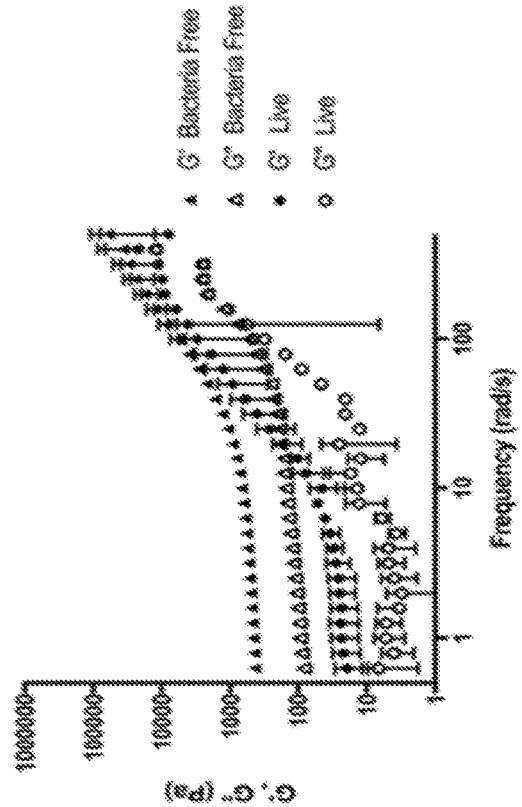
Figure 18B:
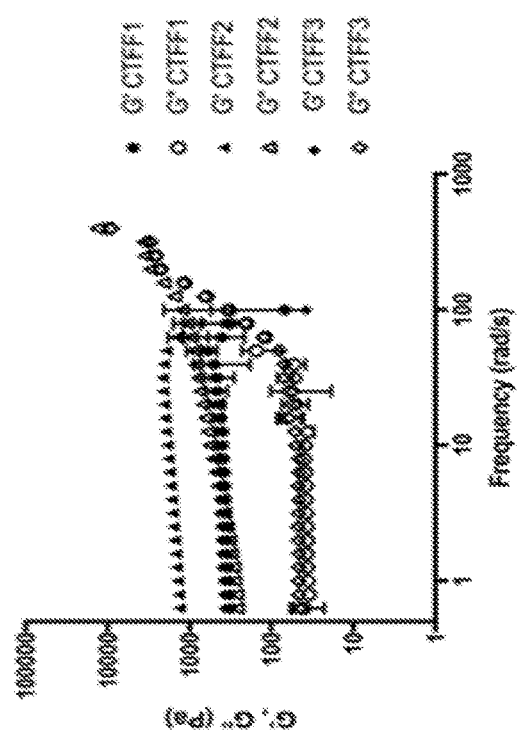
Figure 18D:
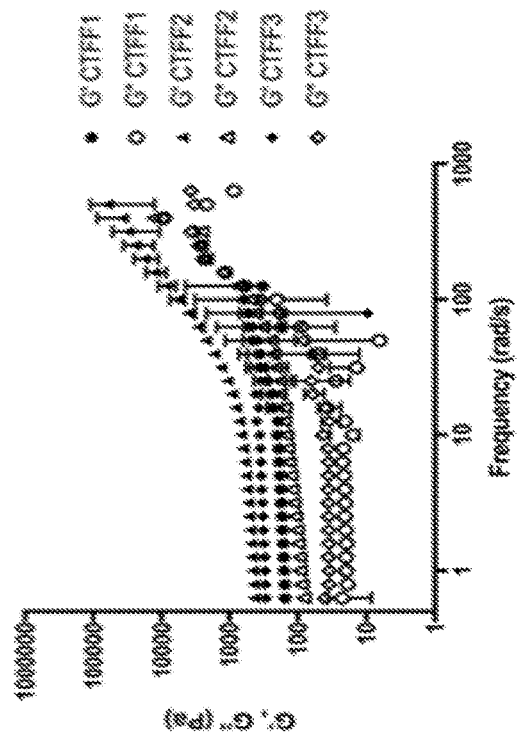

FIGS. 18A, 18B, 18C and 18D depict the rheological properties of engineered hydrogels as the storage modulus (G') and loss modulus (G") presented as a function of frequency. FIG. 18A shows the effect of treatment with guanidine hydrochloride which kills bacterial cells on the storage modulus and loss modulus of the hydrogel. Guanidine hydrochloride untreated hydrogels="Live"; Guanidine hydrochloride-treated hydrogels="Bacteria Free". FIG. 18B shows the effect of disulfide bonding on the storage moduli and loss moduli of hydrogels comprising curli fiber comprising non-mutant CsgA-TTF2 ("CTFF2"), or CsgA-TTF2 in which all cysteines have been mutated to alanine residues ("CTFF2NS"). FIG. 18C shows the storage moduli and loss moduli of biologic hydrogels comprising curli fibers comprising either CsgA-TFF1 ("CTFF1"), CsgA-TFF2 ("CTFF2"), or CsgA-TFF3 ("CTFF3") that have not been treated with DNAse. FIG. 18D shows the storage moduli and loss moduli of biologic hydrogels comprising curli fibers comprising either CsgA-TFF1 ("CTFF1"), CsgA-TFF2 ("CTFF2"), or CsgA-TFF3 ("CTFF3") that have been treated with DNAse.

Figure 19A:
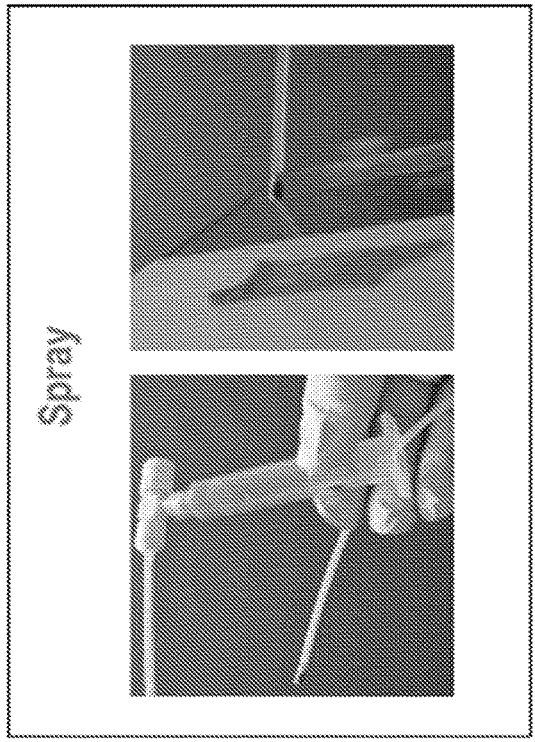
Figure 19B:
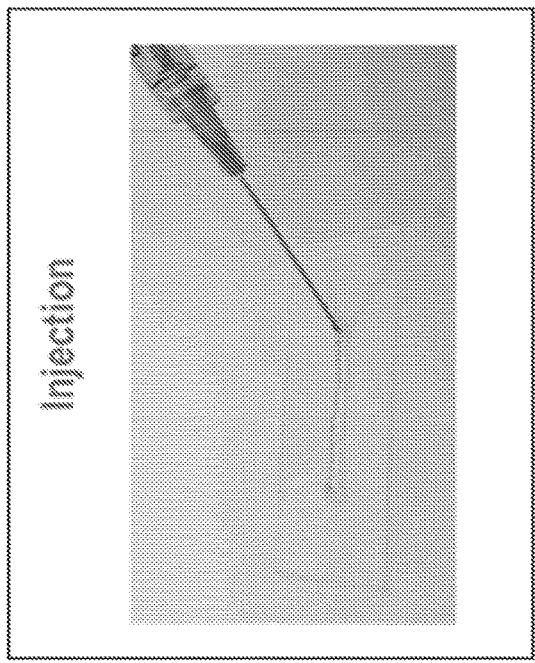
Figure 19D:
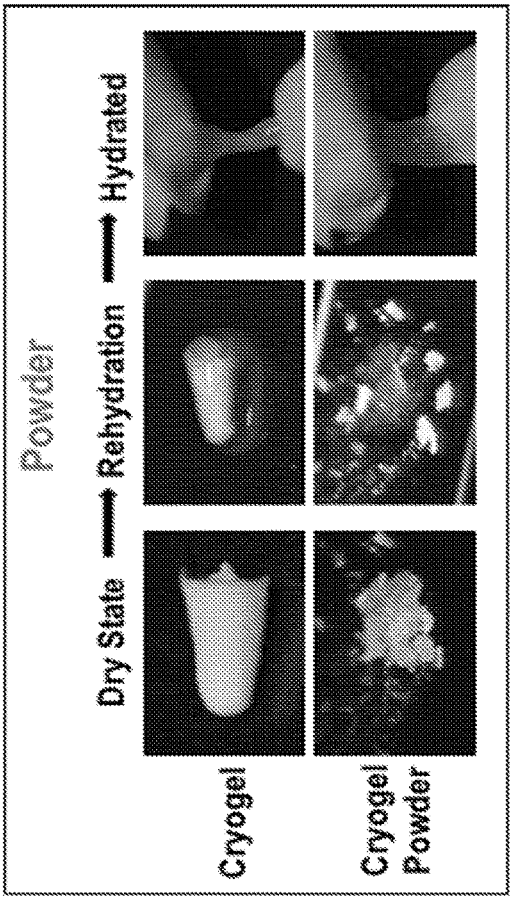
Figure 19C:
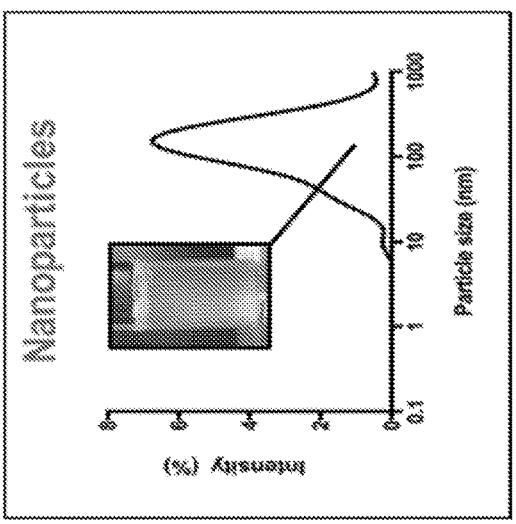

FIGS. 19A, 19B, 19C and 19D depict various alternative methods for delivering biologic hydrogels. FIG. 19A depicts the delivery of a biologic hydrogel comprising curli fibers comprising CsgA-TFF2 by injection. FIG. 19B depicts the delivery of a biologic hydrogel comprising curli fibers comprising CsgA-TFF2 by spraying using an endoscopic device on a mucosal site of a goat intestine. FIG. 19C depicts the size distribution of nanoparticles generated from a biologic hydrogel comprising curli fibers comprising CsgA-TFF2 (graph), and a photograph of a solution comprising the nanoparticles (inset photograph). FIG. 19D depicts a biologic hydrogel comprising curli fibers comprising CsgA-TFF2 in a variety of physical forms including a cryogel and a cryogel powder, and shows the ability of the cryogel and cryogel powder to rapidly resume its previous shape upon rehydration.

Figure 20B:
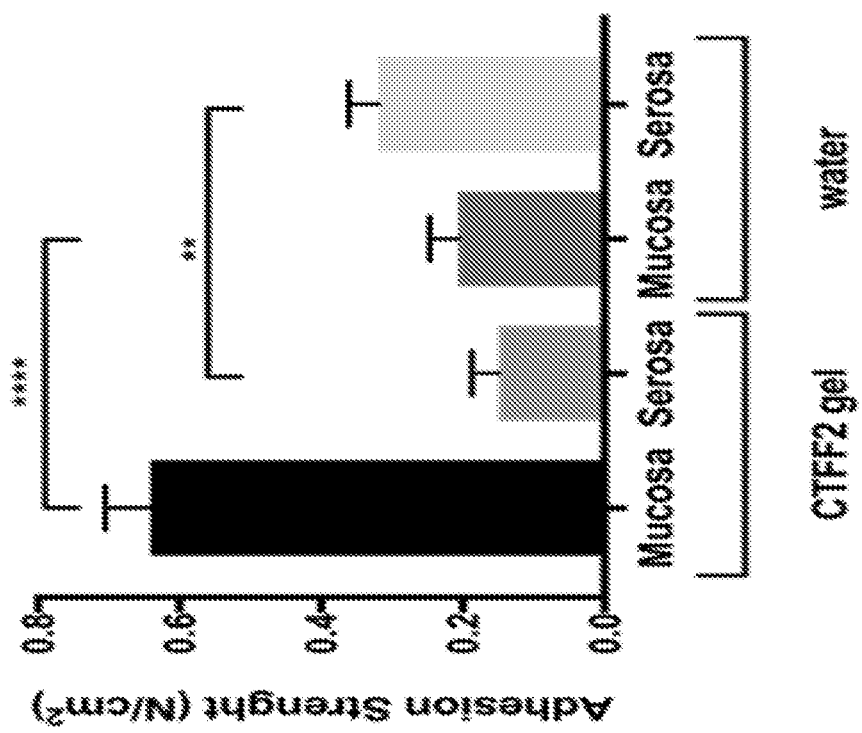
Figure 20A:
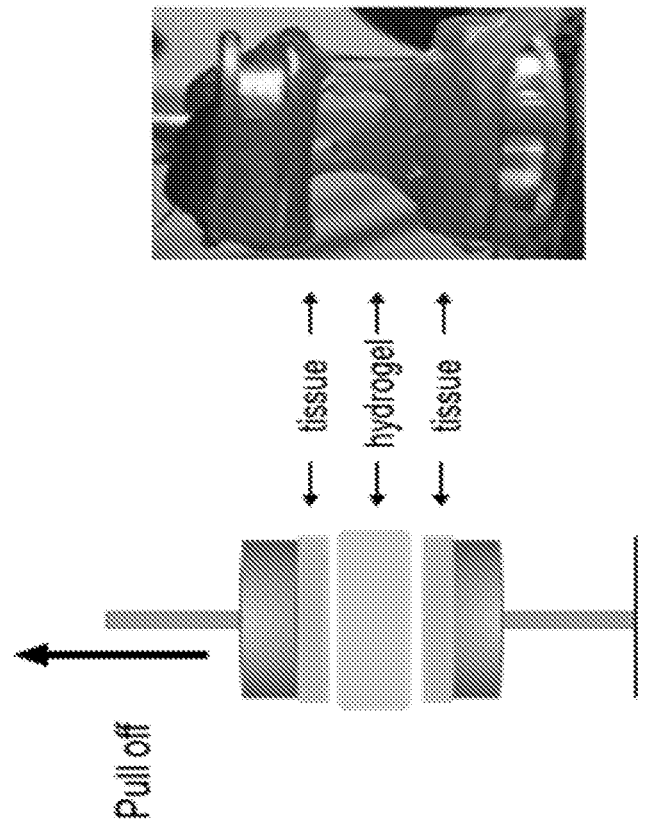

FIG. 20A depicts a schematic and a photograph of a probe with the hydrogel comprising curli fibers comprising CsgA-TFF2 ("cTFF2 gel") attached to goat mucosa. The probe is withdrawn at specific rate. FIG. 20B is a bar graph depicting the mucoadhesive strength of a biologic hydrogel comprising curli fiber comprising CsgA-TFF2 ("cTFF2 gel") to either the mucosal or the serosal side of the goat colon. Mean±s.e.m.; n=3, P<0.0047, *P<0.0001.

Figure 21A:
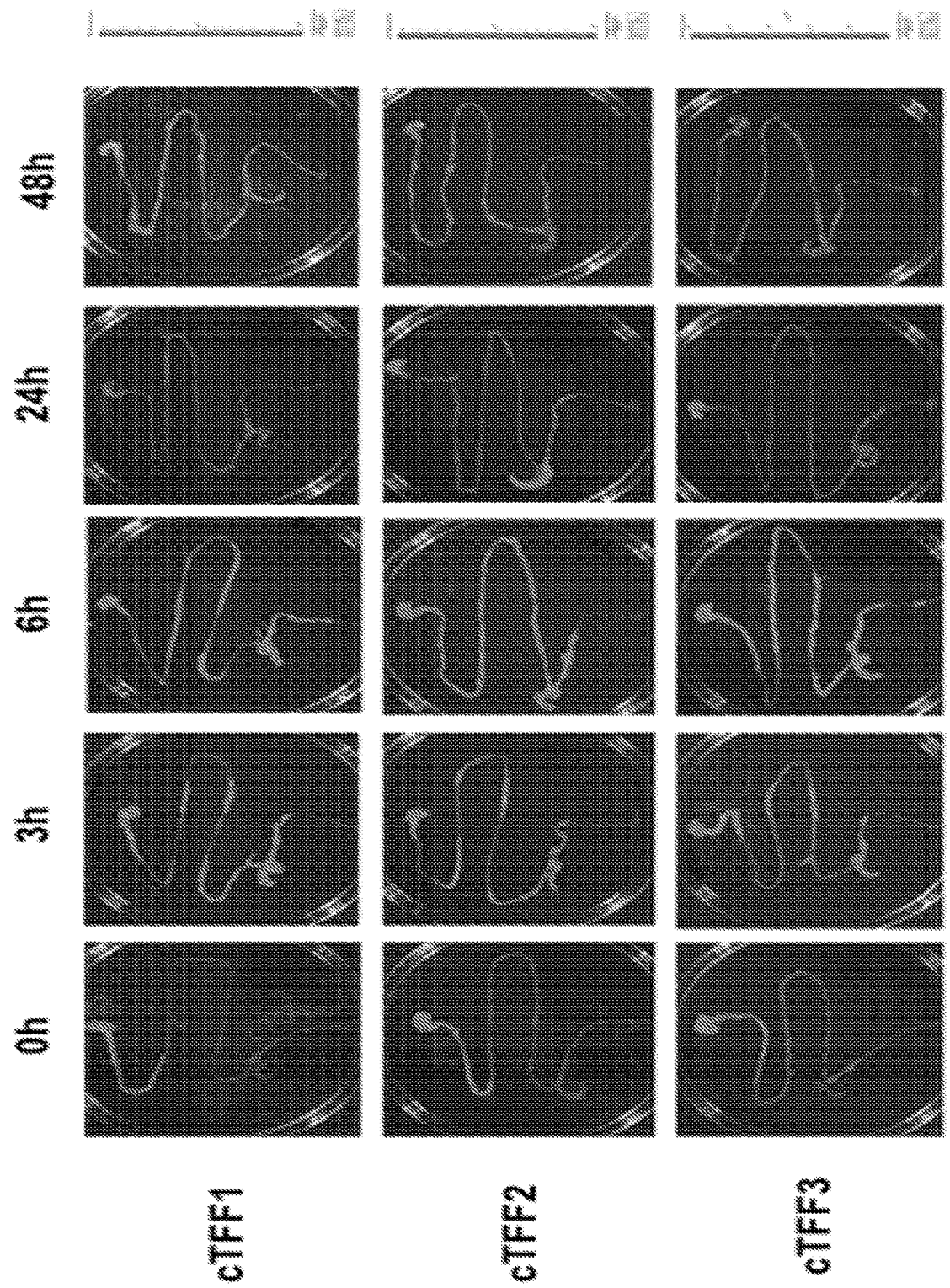
Figure 21B:
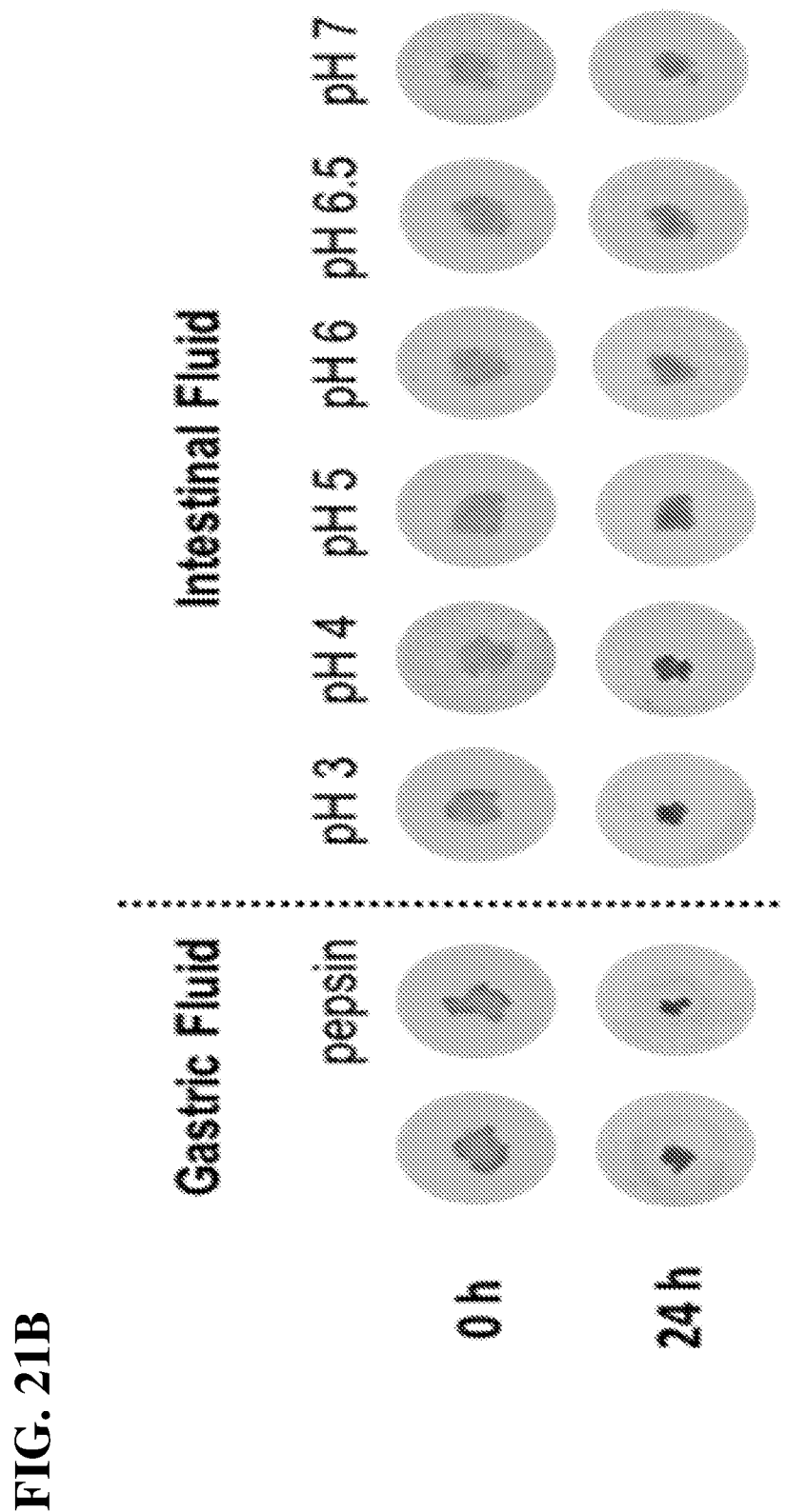

FIGS. 21A and 21B depict the in vivo tracking and visualization of biologic hydrogels in mouse intestines. FIG. 21A depicts images of dissected intestines by IVIS following administration of Cy7-labeled biologic hydrogels comprising curli fibers comprising either CsgA-TFF1 ("cTFF1"), CsgA-TFF2 ("cTFF2"), or CsgA-TFF3 ("cTFF3"). Bar graphs (right) show quantification of fluorescence. FIG. 21B depicts the hydrogel stability in gastric and intestinal fluids.

Figure 22A:
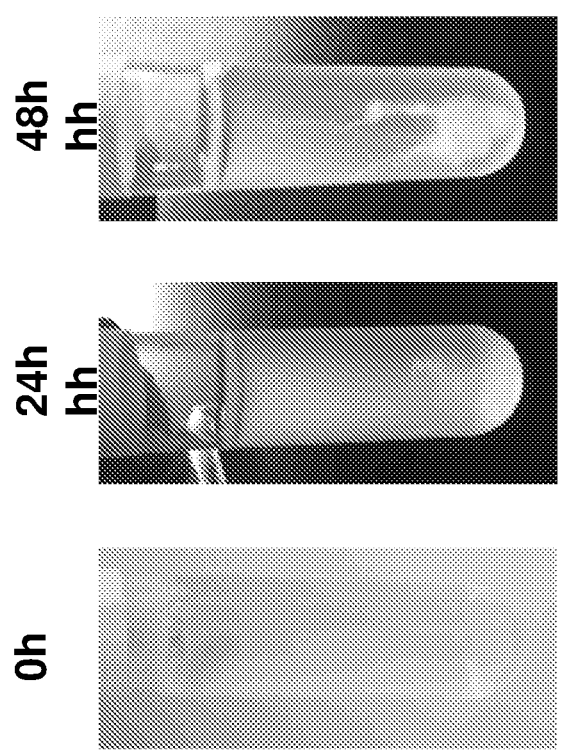

FIG. 22A depicts a bar graph showing the growth rate of bacteria present in a biologic hydrogel comprising curli fibers comprising CsgA-TFF2 at 24 hours, as determined by measuring the dry mass of the hydrogel, following the addition of either water, Luria Broth (LB) without SDS, LB with 0.1% SDS, and LB with 1% SDS, as a gelling agent. Mean±s.e.m.; n=3 (a,b) *P<0.019,P<0.0003, *P<0.0001 by ANOVA test.

Figure 22B:
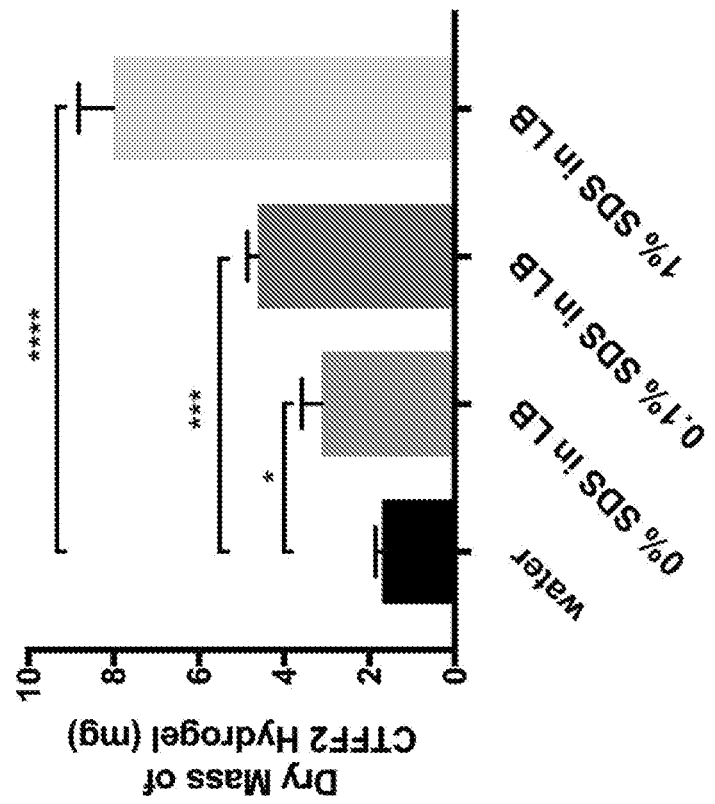

FIG. 22B depicts optical photographs of the growth rate of CTTF2 hydrogel after 24 hours and 48 hours.

Figure 23:
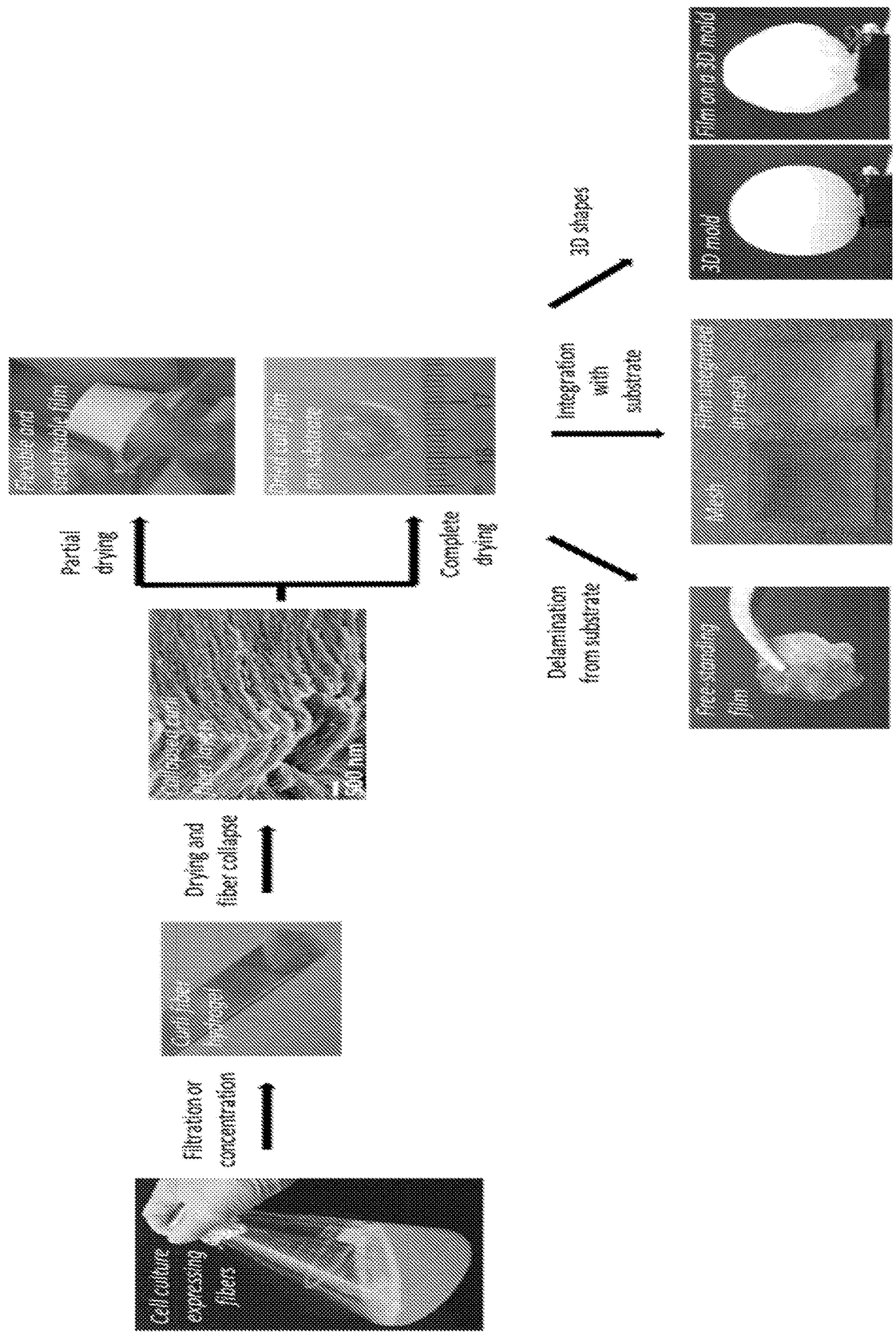

FIG. 23 is an exemplary scheme for the fabrication of thin films and 3D structures using a biologic hydrogel comprising curli fibers.

FIG. 24A depicts the cross-sectional film morphology, as determined using SEM, of a bacteria-free biologic hydrogel formed after treatment with guanidine hydrochloride ("Gdn-HCL") using SDS as a gelling agent. FIG. 24B depicts the cross-sectional film morphology, as determined using SEM, of a biologic hydrogel comprising bacteria formed using SDS as a gelling agent. Bacteria are observed between the collapsed curli layers.

FIGS. 25A, 25B, and 25C depict dehydrated biologic hydrogels that were fabricated by either using pretreatment with 0.8 M guanidine hydrochloride and treatment with 8 M guanidine hydrochloride and SDS (gelling agent) (FIG. 25A), pretreatment with guanidine hydrochloride and SDS (FIG. 25B), or SDS alone without guanidine hydrochloride pretreatment (FIG. 25C) after rehydration with water.

FIGS. 26A, 26B, and 26C show that biologic hydrogels dried on nanostructured or microstructured templates can conform to the shape of the template and imprint on their surface the features of the template. FIG. 26A depicts a biologic hydrogel gel dried on a fine metal mesh template, an SEM image of the metal mesh template, and SEM images at distinct magnifications of the dried film showing the imprinted features of the template on the film's surface. FIG. 26B depicts a biologic hydrogel gel dried on a thick metal mesh template, an SEM image of the metal mesh template, and SEM images at distinct magnifications of the dried film showing the imprinted features of the template on the film's surface. FIG. 26C depicts a biologic hydrogel gel dried on a nylon membrane template, an SEM image of the metal mesh template, and SEM images at distinct magnifications of the dried film showing the imprinted features of the template on the film's surface.

FIG. 27A is a photograph of a water droplets on the surface of a hydrophobic taro leaf. FIG. 27B depicts SEM images at two different magnifications of the taro leaf surface, which was used as a template for drying the biologic hydrogel. FIG. 27C is a photograph of a biologic hydrogel dried on a hydrophobic taro leaf. FIG. 27D depicts SEM images at two different magnifications of the surface of thin films formed by imprinting a biologic hydrogel on the surface of a taro leaf.

Figure 28:
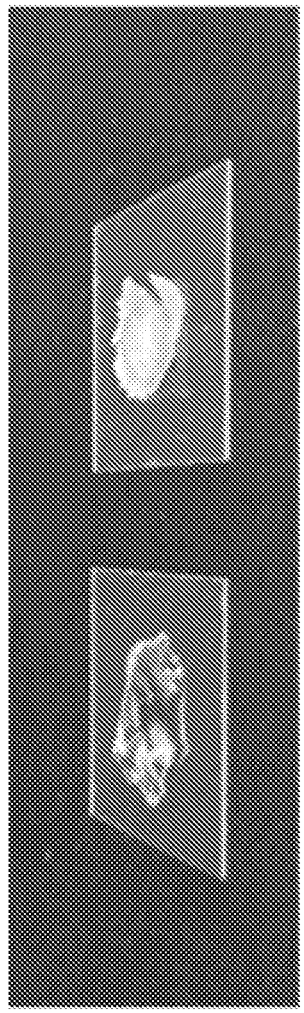

FIG. 28 shows thin films produced by imprinting a biologic hydrogel on either a plastic (flat surface) (left) or a taro leaf (right). Thin films imprinted on the plastic flat surface are hydrophilic and can be rehydrated using water. Thin films imprinted on the hydrophobic taro leaf are hydrophobic and cannot be rehydrated using water.

Figure 29B:
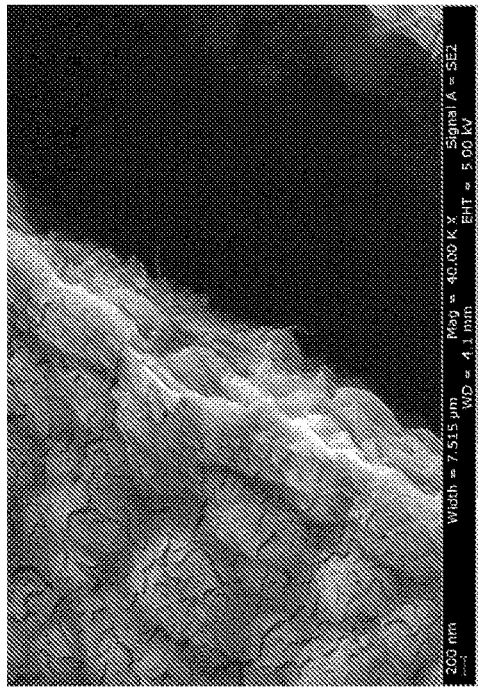
Figure 29D:
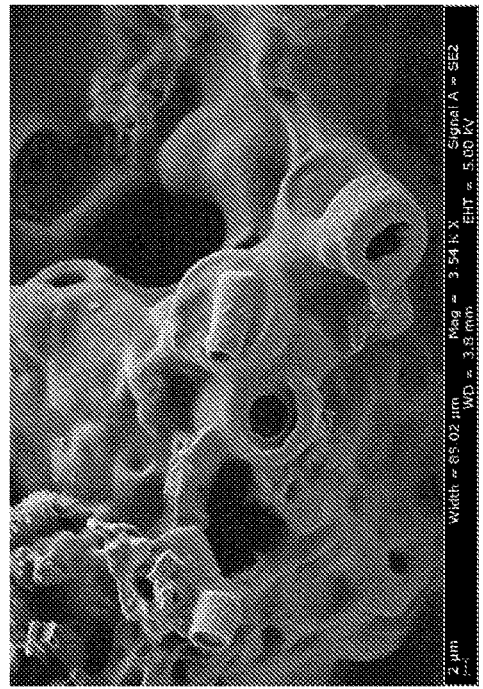
Figure 29A:
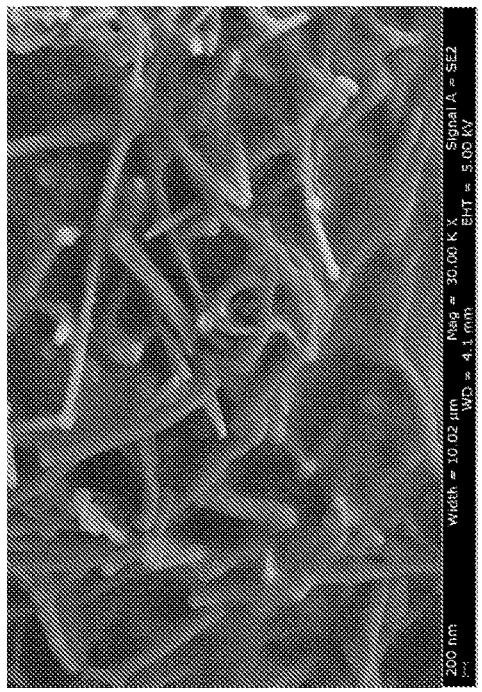
Figure 29C:
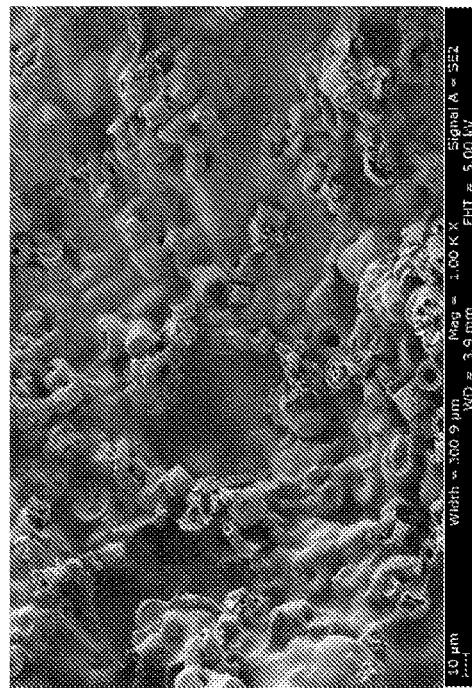

FIGS. 29A and 29B depict SEM images at different magnifications of a biologic hydrogel comprising carbon nanotubes. A culture expressing CsgA-TFF2 was mixed with diatomaceous earth, or with carbon nanotubes. The mixture was filtered onto a 10 μm pore nylon membrane and the composite was concentrated to form a gel. FIGS. 29C and 29D depict SEM images at different magnifications of a biologic hydrogel comprising diatoms.

Figure 30A:
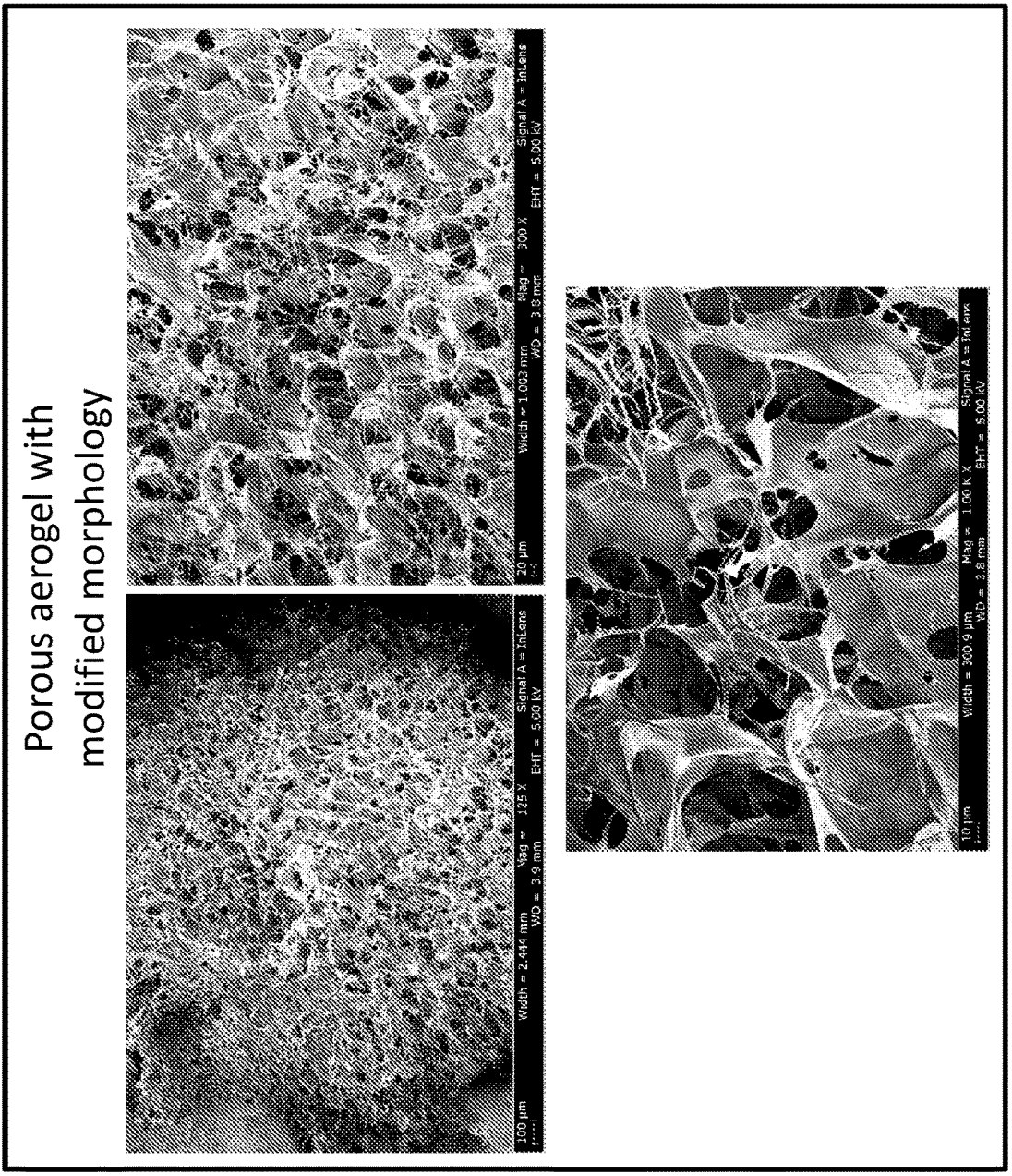
Figure 30B:
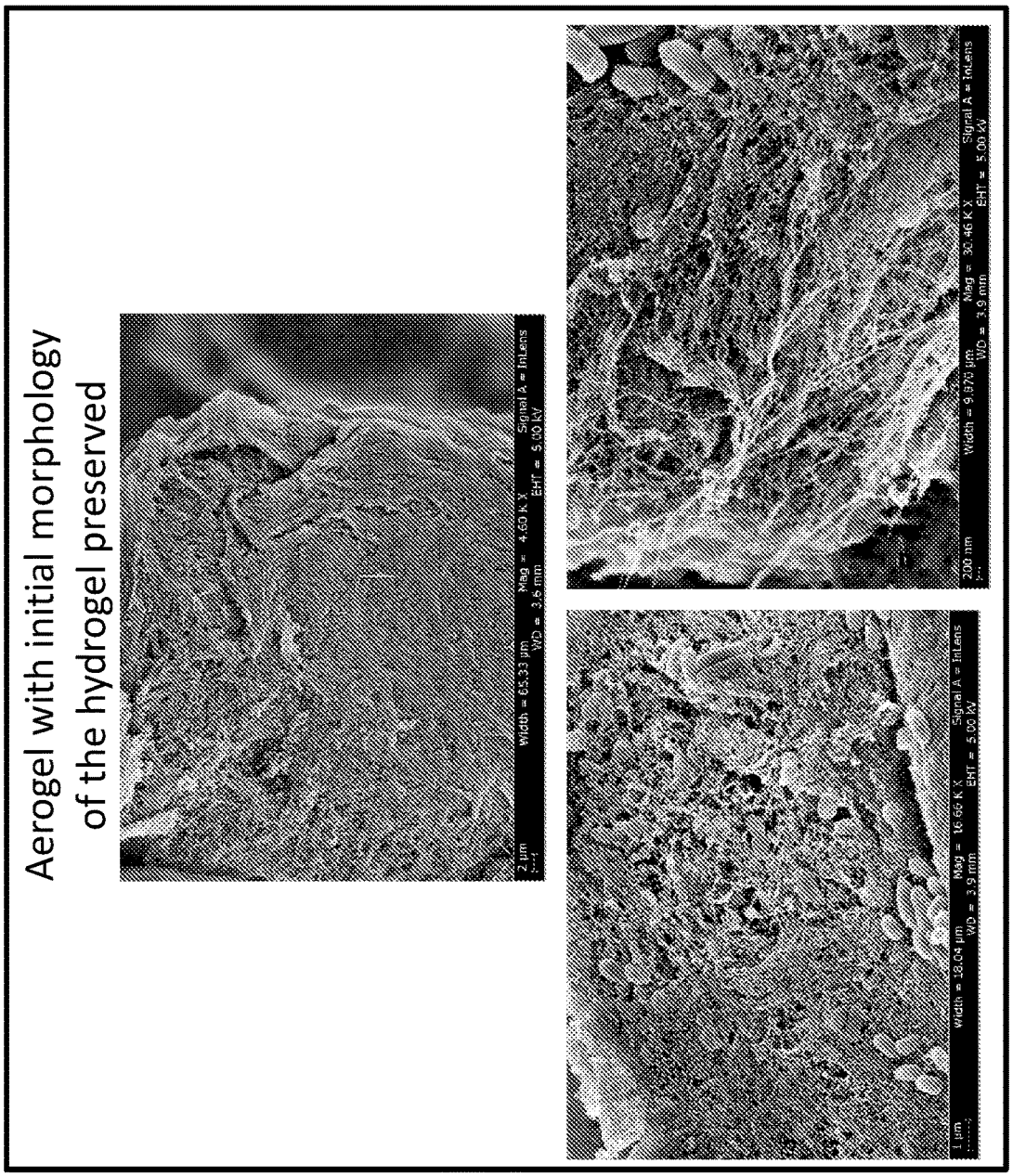

FIGS. 30A and 30B are SEM images of aerogels prepared from a hydrogel by lyophilization or drying using a critical point dryer. FIG. 30A shows SEM images depicting the morphology of a aerogel formed by lyophilizing (i.e., freeze-drying) a hydrogel. Following lyophilization, the hydrogel exhibits modified morphology as compared to the morphology of the hydrogel. FIG. 30B shows SEM images of aerogels prepared from a hydrogel that was subjected to gradual solvent exchange from water to ethanol, and then subjected to critical point drying. The initial morphology of the hydrogel is preserved using this method.

Figure 31F:
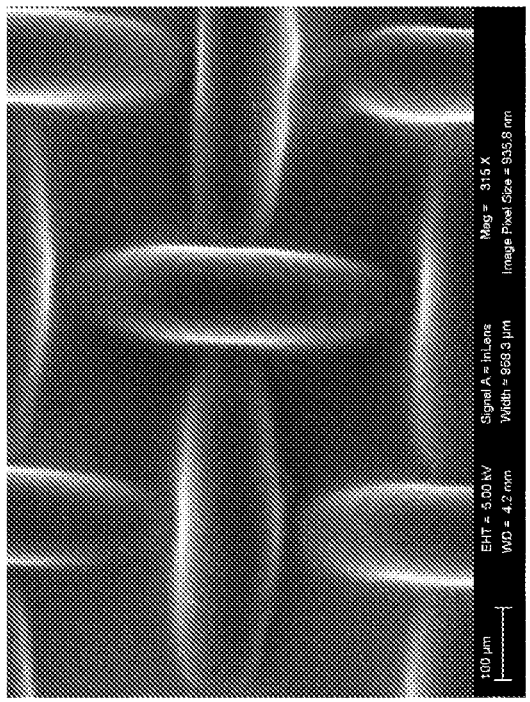
Figure 31E:
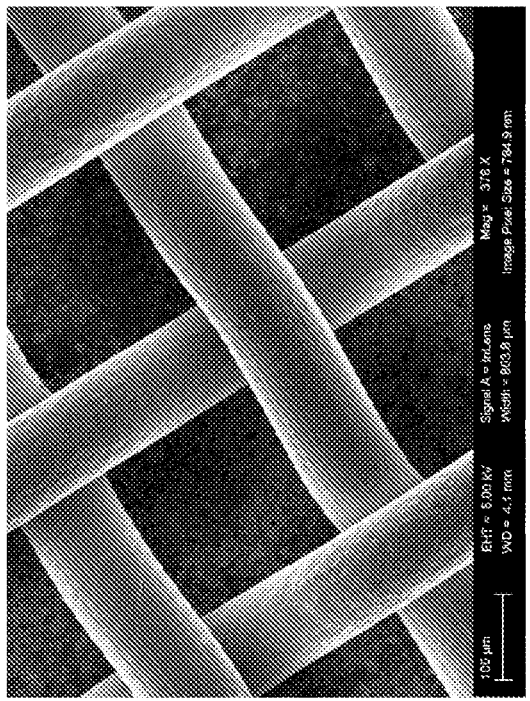

FIGS. 31A, 31B, 31C, 31D, 31E, and 31F are SEM images of several porous supports before and after a biologic hydrogel was overlayed and dried on the porous supports. The dried hydrogels form a conformal coating on the porous supports and integrated with the porous matrix. FIG. 31A is an SEM image of a wood support alone. FIG. 31B is an SEM image of a wood support coated with a curli film. FIG. 31C is an SEM image of a paper support alone. FIG. 31D is an SEM image of a paper support coated with a curli film. FIG. 31E is an SEM image of a fine metal mesh support alone. FIG. 31F is an SEM image of a fine metal mesh support coated with a curli film.

Figure 32B:
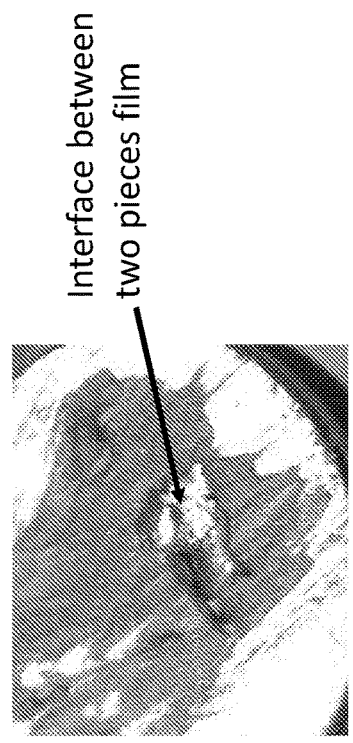
Figure 32D:
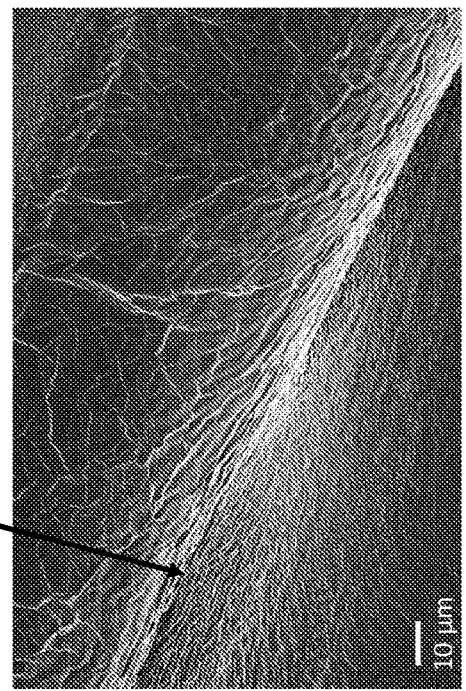
Figure 32A:
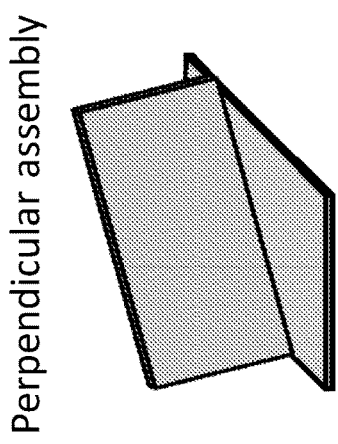
Figure 32C:
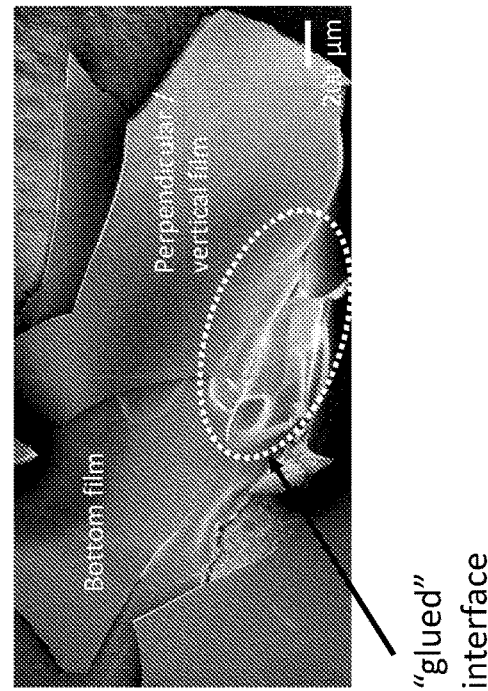

FIGS. 32A, 32B, 32C, and 32D depict an exemplary perpendicular assembly of thin films comprising curli fiber as building blocks for 3D structures. FIG. 32A is an image of the assembly of two pieces of curli thin films forming a perpendicular assembly. FIG. 32B is an optical image of a perpendicular film assembly. Films were deposited on SEM holders using silver paste and coated with 5 nm of Pt/Pd for imaging. FIG. 32C is an SEM image of the fused curli thin films at low magnification. FIG. 32D is an SEM image of the interfaces forming the "glue" or attachment point of the two pieces of film.

Figure 33A:
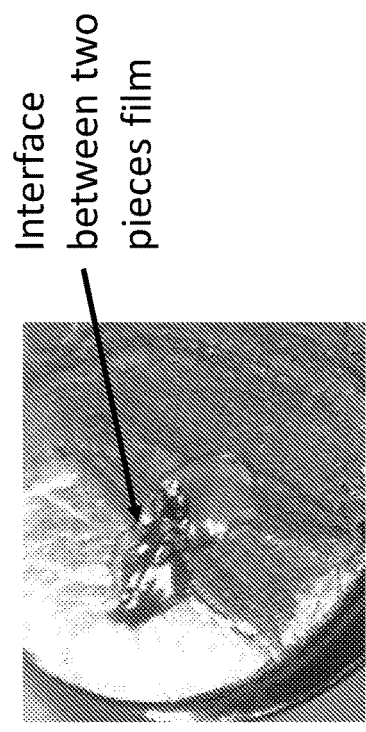
Figure 33B:
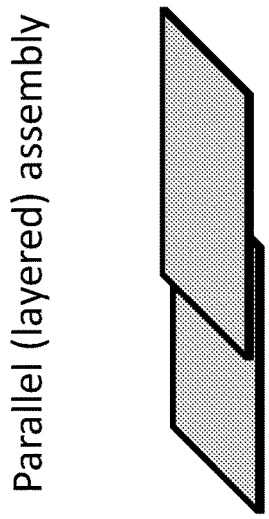
Figure 33C:
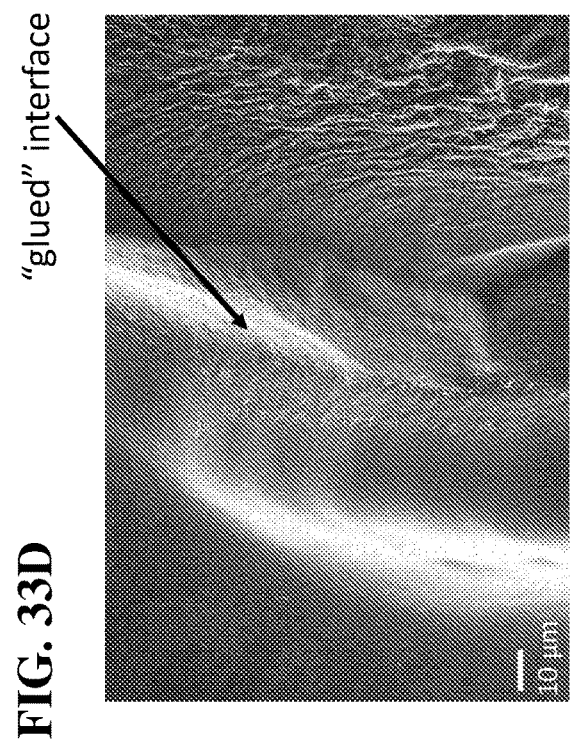
Figure 33D:
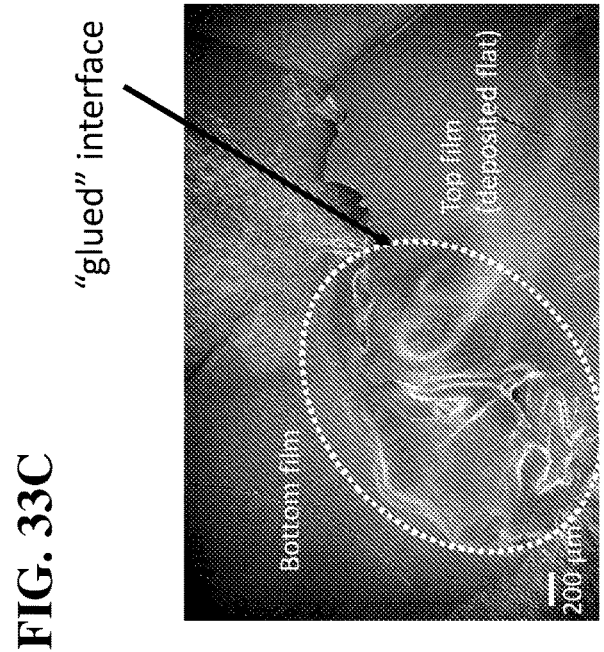

FIGS. 33A, 33B, 33C, and 33D depict an exemplary parallel (layered) assembly of thin films comprising curli fiber as building blocks for 3D structures. FIG. 33A is an image of the assembly of two pieces of curli thin films forming a parallel assembly. FIG. 33B is an optical image of a perpendicular film assembly. Films were deposited on SEM holders using silver paste and coated with 5 nm of Pt/Pd for imaging. FIG. 33C is an SEM image of the fused curli thin films at low magnification. FIG. 33D is an SEM image of the interfaces forming the "glue" or attachment point of the two pieces of film.

FIGS. 34A, 34B, 34C, 34D, 34E, and 34F are images of thin film comprising curli fibers that were in buffer solutions at pH 2 (FIG. 34A), pH 4 (FIG. 34B), pH 7 (FIG. 34C), pH 10 (FIG. 34D), or in the solvents hexafluoroisopropanol (HFPI) (FIG. 34E) or trifluoroacetic acid (TFA) (FIG. 34F) for 24 hours. Despite changes in color/transparency, the films remained intact, showing their resistance to harsh environments (low and high pH, and solvents known to disassemble curli fibers).

DETAILED DESCRIPTION

Definitions

In order that the present invention may be more readily understood, certain term are first defined.

As used herein, the term "curli nanofiber," "curli fiber" or "curli nanofiber aggregate" are used interchangeably to refer to a curli fiber that comprises a CsgA polypeptide. A "curli nanofiber" or "curli nanofiber aggregate" may be produced by a microorganism engineered to produce a curli fiber. Curli nanofibers can be naturally occurring, or genetically engineered. A "mucoadhesive curli fiber" refers to a curli fiber comprising a subunit capable of binding to a mucosal component (e.g., a mucosal protein such as mucin).

As used herein, the term "hydrogel" refers to a network of polymer chains (e.g., recombinant proteins) in which water or a solvent acts as a dispersion medium. In some embodiments, hydrogels have tunable mechanical properties which are not possible to achieve with other compositions, such as biofilms. In some embodiments, a hydrogel may be self-healing, in that the hydrogel can be broken apart and put back together. In other words, dried pieces of a hydrogel can be rehydrated and assembled together using the re-hydrated gel as a "glue."

As used herein, the term "biologic hydrogel" refers to a hydrogel that has been prepared from any biologic composition, e.g., from a microbial culture, e.g., a bacterial culture or a yeast culture. In some embodiments, the biologic hydrogel comprises a higher storage modulus (G') than loss modulus (G"). In some embodiments, the biologic hydrogel comprises a cell (e.g., a bacterial cell, a yeast cell, or a mammalian cell) or a component thereof. In some embodiments, the biologic hydrogel comprises at least 1%, e.g., at least 1%, 2%, 2.5%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70% (w/w) or more cells. In some embodiments, the cell is a live cell (e.g., a live bacterial cell, a live yeast cell, or a live mammalian cell). In other embodiments, a cell has been removed from the biologic hydrogel. In some embodiments, the biological hydrogel comprises less than 90% (w/w), e.g., less than 80%, 70%, 60%, 50%, 40%, 30%, 20%, 10%, 5%, 2.5%, 1%, 0.5% (w/w), or less cells (e.g., bacterial cells). In some embodiments, the biologic hydrogel comprises a therapeutic protein. In some embodiments, the biologic hydrogel comprises a medium wherein cells (e.g., microbial cells (e.g., bacterial cells or yeast cells) and/or mammalian cells) may be cultured. For example, in some embodiments, the biologic hydrogel comprises a medium wherein cells, e.g., microbial cells (e.g., bacterial cells and/or yeast cells) and/or mammalian cells, can proliferate. In some embodiments, the biological hydrogel comprises pores. In some embodiments, the biological hydrogel comprises at least 1%, e.g., at least 1%, 2%, 2.5%, 3%, 4%, 5%, 6%, 7%, 8%, 9%, 10%, 20%, 30%, 40%, 50%, 60%, 70% (w/w) or more curli fiber. In some embodiments, the biological hydrogel comprises at least 3% (w/w) curli fibers. In some embodiments, the biological hydrogel comprises at least 4% (w/w) curli fibers. In some embodiments, the biological hydrogel comprises at least 5% (w/w) curli fibers. In some embodiments, the biological hydrogel comprises between about 3% and about 5% curli fiber (w/w). In some embodiments, the biological hydrogel has a storage modulus (G') of at least 50 pascal (Pa) (e.g., at least 60, at least 70, at least 80, at least 90, at least 100, at least 150, at least 200, at least 250, at least 300, at least 350, at least 400, at least 450, at least 500, at least 600, at least 700, at least 800, at least 900, at least 1000, at least 1500, at least 2000, at least 3000, at least 4000, at least 5000, at least 6000, at least 7000, at least 8000, at least 9000, or greater pascal (Pa)). In some embodiments, the biological hydrogel comprises at least 70% water (w/w) (e.g., at least 75%, at least 80%, at least 85%, at least 90%, at least 95% (w/w) or more water). In other embodiments, the biologic hydrogel comprises less than 10% (w/w), e.g., less than 9%, 8%, 7%, 6%, 5%, 4%, 3%, 2%, 1%, 0.5%, 0.25%, 0.1%, 0.05% (w/w), or less surfactant (e.g., SDS).

As used herein, the term "aerogel" refers to a porous material derived from a gel in which the liquid component of the gel has been replaced with a gas. Aerogels may be produced, in one embodiment, by removing the liquid component of a hydrogel through critical point drying (e.g., using a critical point dryer). Aerogels may also be prepared, in some embodiments, by lyophilizing (i.e., freeze-drying) a hydrogel.

As used herein, the term "filtration" or "filtering" refers to the process of purifying curli nanofiber aggregates away from microbes, such as bacteria or viruses, nucleic acids, such as DNA or RNA, proteins that are not expressed as part of the curli fiber or are otherwise attached to the curli fiber, or any other organic or inorganic contaminants using a filter.

As used herein, the term "engineered bacterium" or "engineered bacterial cell" refers to a bacterial cell that has been genetically modified from their native state. For instance, an engineered bacterial cell may have nucleotide insertions, nucleotide deletions, nucleotide rearrangements, and nucleotide modifications introduced into their DNA. These genetic modifications may be present in the chromosome of the bacteria or bacterial cell, or on a plasmid in the bacteria or bacterial cell. Engineered bacterial cells of the disclosure may comprise exogenous nucleotide sequences on plasmids. Alternatively, recombinant bacterial cells may comprise exogenous nucleotide sequences stably incorporated into their chromosome. In some embodiments, the engineered bacterium is non-pathogenic. In some embodiments, the engineered bacterium is pathogenic.

"Probiotic", as used herein, refers to a live, non-pathogenic microorganisms, e.g., bacteria, which can confer health benefits to a host organism. In some embodiments, the host organism is a mammal. In some embodiments, the host organism is a human. Some species, strains, and/or subtypes of non-pathogenic bacteria are currently recognized as probiotic bacteria. Examples of probiotic bacteria include, but are not limited to, *Bifidobacteria, Escherichia coli, Lactobacillus,* and *Saccharomyces,* e.g., *Bifidobacterium bifidum, Enterococcus faecium, Escherichia coli* strain Nissle, *Lactobacillus acidophilus, Lactobacillus bulgaricus, Lactobacillus paracasei,* and *Lactobacillus plantarum*. The probiotic may be a variant or a mutant strain of bacterium. Non-pathogenic bacteria may be genetically engineered to enhance or improve desired biological properties, e.g., survivability. Non-pathogenic bacteria may be genetically engineered to provide probiotic properties. Probiotic bacteria may be genetically engineered to enhance or improve probiotic properties.

As used herein, the term "gene" refers to a nucleic acid fragment that encodes a protein or fragment thereof, optionally including regulatory sequences preceding (5' non-coding sequences) and following (3' non-coding sequences) the coding sequence. In one embodiment, a "gene" does not include regulatory sequences preceding and following the coding sequence.

As used herein, a "heterologous" gene or "heterologous sequence" refers to a nucleotide sequence that is not normally found in a given cell in nature. As used herein, a heterologous sequence encompasses a nucleic acid sequence that is exogenously introduced into a given cell. "Heterologous gene" includes a native gene, or fragment thereof, that has been introduced into the host cell in a form that is different from the corresponding native gene. A heterologous gene may include a native gene, or fragment thereof, introduced into a non-native host cell. Thus, a heterologous gene may be foreign or native to the recipient cell; a nucleic acid sequence that is naturally found in a given cell but expresses an unnatural amount of the nucleic acid and/or the polypeptide which it encodes; and/or two or more nucleic acid sequences that are not found in the same relationship to each other in nature. As used herein, the term "endogenous gene" refers to a native gene in its natural location in the genome of an organism. As used herein, the term "transgene" refers to a gene that has been introduced into the host organism, e.g., host bacterial cell's genome.

A "promoter" as used herein, refers to a nucleotide sequence that is capable of controlling the expression of a coding sequence or gene. Promoters are generally located 5' of the sequence that they regulate. Promoters may be derived in their entirety from a native gene, or be composed of different elements derived from promoters found in nature, and/or comprise synthetic nucleotide segments. Those skilled in the art will readily ascertain that different promoters may regulate expression of a coding sequence or gene in response to a particular stimulus, e.g., in a cell-specific or tissue-specific manner, in response to different environmental or physiological conditions, or in response to specific compounds. Prokaryotic promoters are typically classified into two classes: inducible and constitutive.

"Constitutive promoter" refers to a promoter that is capable of facilitating continuous transcription of a coding sequence or gene under its control and/or to which it is operably linked. Constitutive promoters and variants are well known in the art and include, but are not limited to, a constitutive *Escherichia coli* $\sigma^S$ promoter, a constitutive *Escherichia coli* $\sigma^{32}$ promoter, a constitutive *Escherichia coli* $\sigma^{70}$ promoter, a constitutive *Bacillus subtilis* $\sigma^A$ promoter, a constitutive *Bacillus subtilis* $\sigma^B$ promoter, and a bacteriophage T7 promoter.

An "inducible promoter" refers to a promoter that initiates increased levels of transcription of the coding sequence or gene under its control in response to a stimulus or an exogenous environmental condition. A "directly inducible promoter" refers to a regulatory region, wherein the regulatory region is operably linked to a gene encoding a protein or polypeptide, where, in the presence of an inducer of said regulatory region, the protein or polypeptide is expressed.

An "indirectly inducible promoter" refers to a regulatory system comprising two or more regulatory regions, for example, a first regulatory region that is operably linked to a first gene encoding a first protein, polypeptide, or factor, e.g., a transcriptional regulator, which is capable of regulating a second regulatory region that is operably linked to a second gene, the second regulatory region may be activated or repressed, thereby activating or repressing expression of the second gene. Both a directly inducible promoter and an indirectly inducible promoter are encompassed by "inducible promoter."

The term "operatively linked" includes having an appropriate transcription start signal (e.g., promoter) in front of the polynucleotide sequence to be expressed, and having an appropriate translation start signal (e.g., a Shine Delgarno sequence and a start codon (ATG)) in front of the polypeptide coding sequence and maintaining the correct reading frame to permit expression of the polynucleotide sequence under the control of the expression control sequence, and, optionally, production of the desired polypeptide encoded by the polynucleotide sequence. In some examples, transcription of a gene encoding a recombinant polypeptide as described herein is under the control of a promoter sequence (or other transcriptional regulatory sequence) which controls the expression of the nucleic acid in a cell-type in which expression is intended. It will also be understood that the gene encoding a recombinant polypeptide as described herein can be under the control of transcriptional regulatory sequences which are the same or which are different from those sequences which control transcription of the naturally-occurring form of a protein.

As used herein, the term "expression" refers to the transcription and stable accumulation of sense (mRNA) or anti-sense RNA derived from a nucleic acid, and/or to translation of an mRNA into a polypeptide.

The terms "overexpression" or "overexpress", as used herein refers to the expression of a functional nucleic acid, polypeptide or protein encoded by DNA in a host cell, wherein the nucleic acid, polypeptide or protein is either not normally present in the host cell, or wherein the nucleic acid, polypeptide or protein is present in the host cell at a higher level than that normally expressed from the endogenous gene encoding the nucleic acid, polypeptide or protein.

The term "genetic modification," as used herein, refers to any genetic change. Exemplary genetic modifications include those that increase, decrease, or abolish the expression of a gene, including, for example, modifications of native chromosomal or extrachromosomal genetic material. Exemplary genetic modifications also include the introduction of at least one plasmid, modification, mutation, base deletion, base addition, and/or codon modification of chromosomal or extrachromosomal genetic sequence(s), gene over-expression, gene amplification, gene suppression, promoter modification or substitution, gene addition (either single or multi-copy), antisense expression or suppression, or any other change to the genetic elements of a host cell, whether the change produces a change in phenotype or not. Genetic modification can include the introduction of a plasmid, e.g., a plasmid comprising at least one gene encoding an amyloid protein operably linked to a promoter, into a bacterial cell. Genetic modification can also involve a targeted replacement in the chromosome, e.g., to replace a native gene promoter with an inducible promoter, regulated promoter, strong promoter, or constitutive promoter. Genetic modification can also involve gene amplification, e.g., introduction of at least one additional copy of a native gene into the chromosome of the cell. Alternatively, chromosomal genetic modification can involve a genetic mutation.

As used herein, the term "crosslinking agent" refers to a substance that is able to form chemical linkages between two polymers (e.g., two polypeptides) or two different regions of the same polymer (e.g., two regions of one protein).

As used herein, the term "surfactant" refers to a natural or synthetic amphiphilic compound. In some embodiments, the surfactant is non-ionic. In some embodiments, the surfactant is anionic. In some embodiments, the surfactant is zwitterionic. In some embodiments, the surfactant is ionic. Exemplary surfactants include, but are not limited to, SDS, 4-octylphenol polyethoxylate, polyethylene glycol sorbitan monolaurate, sodium lauroyl sarcosinate, and polyethylene glycol sorbitan monooleate. In one embodiment, the use of a surfactant speeds up the formation of a hydrogel.

As used herein, the term "solvent" generally refers to a liquid capable of holding a substance in solution. In some embodiments, the solvent is selected from the group consisting of water, glycerol, ethanol, methanol, Dimethyl sulfoxide (DMSO), or combinations thereof. In some embodiments, the solvent is a water miscible solvent.

A "pharmaceutical composition," as used herein, refers to a composition comprising an active ingredient (e.g., a bacterial cell, a drug, or a detectable compound) with other components, such as a physiologically suitable carrier and/or excipient.

As used herein, the term "pharmaceutically acceptable" or "pharmacologically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Moreover, for animal (e.g., human) administration, it will be understood that compositions should meet sterility, pyrogenicity, general safety and purity standards as required by the FDA Office of Biological Standards.

As used herein, the term "pharmaceutically acceptable excipient" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, disintegrating agents, binders, sweetening agents, flavoring agents, perfuming agents, protease inhibitors, plasticizers, emulsifiers, stabilizing agents, viscosity increasing agents, film forming agents, solubilizing agents, surfactants, preservative and antioxidants can also be present in the formulation. The terms such as "excipient", "carrier", "pharmaceutically acceptable excipient" or the like are used interchangeably herein.

A "plasmid" or "vector" includes a nucleic acid construct designed for delivery to a host cell or transfer between different host cell. An "expression plasmid" or "expression vector" can be a plasmid that has the ability to incorporate and express heterologous nucleic acid fragments in a cell. An expression plasmid may comprise additional elements, for example, the expression vector may have two replication systems, thus allowing it to be maintained in two organisms. The nucleic acid incorporated into the plasmid can be operatively linked to an expression control sequence when the expression control sequence controls and regulates the transcription and translation of that polynucleotide sequence.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

A "nucleic acid" or "nucleic acid sequence" may be any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

The term "non-pathogenic" as used herein to refer to bacteria refers to bacteria that are not capable of causing disease or harmful responses in a host. In some embodiments, non-pathogenic bacteria are commensal bacteria. Examples of non-pathogenic bacteria include, but are not limited to *Bacillus, Bacteroides, Bifidobacterium, Brevibacteria, Clostridium, Enterococcus, Escherichia coli*, e.g., *Escherichia coli* Nissle 1917, *Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus*, and *Lactococcus lactis*. Naturally pathogenic bacteria may be genetically engineered to provide reduce or eliminate pathogenicity.

As used herein, the term "activity polypeptide" refers to a polypeptide having an activity or function, such that when it is present on a curli fiber and/or in a biofilm, it confers upon the curli fiber and/or biofilm a property, function, or activity which it did not have in the absence of the polypeptide. Such functions include catalytic function, recognition function, or structural function. A functionalizing polypeptide can be of any size and include, e.g., an enzyme, a polypeptide that binds another molecule, an antibody, an antibody mimetic sequence, a polypeptide that binds a metal, an antibody, a therapeutic agent, a diagnostic agent, a metal, an antimicrobial agent, an anti-inflammatory agent, or an anticancer agent. Examples of polypeptides for use as activity polypeptides include, but are not limited to, an enzyme, a porin, a ribosomal protein, a silk protein, a nanobody, a metal binding domain (MBD), a graphene binding (GBP) domain, a carbon nanotube binding (CBP) domain, a gold binding (A3) domain, CT43, FLAG, Z8, E14, QBP1, CLP12, and AFP8.

As used herein, the term "therapeutic polypeptide" refers to any polypeptide that has a therapeutic effect or may be used for diagnostic purposes when introduced into a eukaryotic organism (e.g., a mammalian subject such as human). In some embodiments, the therapeutic polypeptide is an antibody. In some embodiments, the therapeutic polypeptide is a single domain antibody. In some embodiments, the therapeutic polypeptide is a fusion protein, a hormone, an antigen, a thrombolytic agent, a cytokine or a growth factor. In some embodiments the therapeutic polypeptide is an immunotoxin (e.g., an antibody fused to a cellular toxin). In some embodiments, a therapeutic polypeptide is an enzyme.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence, e.g., SEQ ID NO:1. The degree of homology (percent identity) between a native and a mutant sequence can be determined, for example, by comparing the two sequences using freely available computer programs commonly employed for this purpose on the world wide web (e.g., BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); and U.S. Pat. Nos. 4,518,584 and 4,737,462, which are herein incorporated by reference in their entireties.

As used herein, the term "filter" refers to a surface used to trap curli nanofiber aggregates while allowing microbes or microbial cells, nucleic acids, and proteins that are not expressed as part of the curli fiber or are otherwise attached to the curli fiber to flow through the surface, thereby purifying or isolating the curli nanofiber aggregates. A filter can be, for example, a filter membrane, a mesh, or a cloth or other fabric having pores of a size capable of purifying or isolating amyloid fibers, e.g., curli fibers.

As used herein, the term "filtration" or "filtering" refers to the process of purifying curli nanofiber aggregates away from microbes or microbial cells, such as bacteria or viruses, nucleic acids, such as DNA or RNA, and proteins that are not expressed as part of the curli fiber or are otherwise attached to the curli fiber, using a filter.

As used herein, the term "thin film" or "nanofiber film" refers to one or more layers of amyloid nanofibers, e.g., curli fibers, that form a film. A thin film can be removed from a purification filter so that it is free-standing, or it can be applied to the surface of a substrate. A "free-standing film" refers to a film that is capable of supporting its own weight, e.g., after removal from a filter. A thin film can be completely free of microbes, such as bacteria, or can include microbes, such as bacteria. In some embodiments, the thin film is porous. In some embodiments, the thin film is non porous. In some embodiments, the thin film comprises less than 70% (w/w), e.g., less than 60%, 50%, 40%, 30%, 20%, 10%, 5%, 2.5%, 1%, 0.5% (w/w), or less water. In some embodiments, the thin film remains intact after exposure to a buffered solution at pH 2 for at least 24 hours. In some embodiments, the thin film remains intact after exposure to a buffered solution at pH 4 for at least 24 hours. In some embodiments, the thin film remains intact after exposure to a buffered solution at pH 7 for at least 24 hours. In some embodiments, the thin film remains intact after exposure to a buffered solution at pH 10 for at least 24 hours. In some embodiments, the thin film remains intact after exposure to hexafluoroisopropanol (HFPI) for at least 24 hours. In some embodiments, the thin film remains intact after exposure to trifluoroacetic acid (TFA) for at least 24 hours. In some embodiments, two or more thin films can be used to assemble a three dimensional structure (e.g., in parallel or perpendicular (layered) assembly).

As used herein, the term "biofilm matrix" or "biofilm extracellular matrix" refers to a matrix of extracellular polymeric substances, including, but not limited to extracellular DNA, proteins, glycopeptides, and polysaccharides, which was produced by a mass of microorganisms, such as bacteria, but wherein the microorganisms have been completely or almost completely killed or removed. Accordingly, in one embodiment, a "biofilm matrix" does not comprise any microorganisms, such as bacteria. In one embodiment, a "biofilm matrix" does not comprise any live microorganisms, such as bacteria.

As used herein, the term "biofilm" refers to a matrix of extracellular polymeric substances, including, but not limited to extracellular DNA, proteins, glycopeptides, and polysaccharides, which are produced by a mass of microorganisms, such as bacteria. In one embodiment, a biofilm comprises a biofilm matrix and bacteria. In one embodiment, the bacteria are live bacteria.

As used herein, the term "enzyme" refers to a polypeptide that can act as a catalyst to accelerate or catalyze a chemical reaction. As used herein, the term "enzymatic cascade" refers to two or more polypeptides which are involved in a series of successive chemical reactions.

Definitions of common terms in cell biology and molecular biology can be found in The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Other than in the operating examples, or where otherwise indicated, all numbers expressing quantities of ingredients or reaction conditions used herein should be understood as modified in all instances by the term "about." The term "about" when used in connection with percentages can mean±1%.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Engineered Bacteria of the Invention

In one aspect, provided herein is an engineered bacterial cell has been genetically modified to comprise a heterologous nucleic acid encoding an engineered CsgA fusion protein comprising a CsgA polypeptide and an activity polypeptide. The activity polypeptide may be any polypeptide of interest. For example, in some embodiments the activity polypeptide is a mucoadhesive polypeptide. In some embodiments, the activity polypeptide is a pore-forming polypeptide (e.g., a porin). In some embodiments, the activity polypeptide is a ribosomal polypeptide (e.g., ribosomal protein S6 (RPS6). In some embodiments, the activity polypeptide is a metal binding polypeptide (e.g., a copper-binding polypeptide, a gold-binding polypeptide, or a nickel-binding polypeptide). In some embodiments, the activity polypeptide is a plastocyanin.

In some embodiments, the engineered bacterial cell expresses and secretes the CsgA fusion protein. In some embodiments, the engineered bacterial cell expresses but does not secrete the CsgA fusion protein. In some embodiments, the engineered bacteria comprises one or more curli fiber assembly proteins which allow for the secretion and assembly of curli fibers on the surface of the bacterial cell.

Methods of the present invention use the curli fiber production systems of a bacterium, such as *E. coli* to produce curli fibers that comprise an amyloid domain (e.g., CsgA) Curli fibers are the primary proteinaceous structural component of *E. coli* biofilms. They are highly robust functional amyloid nanofibers with a diameter of approximately 4-7 nm that exist as extended tangled networks encapsulating the cells. Curli fibers or curli are formed from the extracellular self-assembly of CsgA, a small secreted 13-kDa protein (see, e.g., Chapman, M. R. et al. Role of *Escherichia coli* curli operons in directing amyloid fiber formation. Science 295, 851-855 (2002)). A homologous outer-membrane protein, CsgB, nucleates CsgA assembly and also anchors the nanofibers to the bacterial surface. Detached curli fibers can also exist as non-cell associated structural components of the extracellular matrix (ECM). The curli genes exist as two divergently transcribed operons (csgBAC and csgDEFG), whose seven products mediate the structure (CsgA), nucleation (CsgB), processing (CsgE, CsgF), secretion (CsgC, CsgG), and direct transcriptional regulation (CsgD) of curli nanofibers. This curli secretion system is considered a distinct secretion system of its own in gram-negative bacterium and is named the Type-VIII secretion system (T8SS) (see, e.g., Desvaux et al., *Trends Microbiol.* 17, 139-45 (2009), which is hereby incorporated by reference in its entirety).

CsgA is the major structural subunit of curli. The sequences of CsgA and its homologs are known in a number of species, see e.g., *E. coli* (NCBI Gene ID NO: 949055; NCBI Ref Seq: NP_415560). The amino acid sequence of an *E. coli* CsgA polypeptide is provided below:

1   mkllkvaaia    aivfsgsala    gvvpqyggggg    nhggggnnsg
    pnselniyqy    gggnsalalq
61  tdarnsdlti    tqhgggngad    vgqgsddssi    dltqrgfgns    atldqwngkn
    semtvkqfgg
121 gngaavdqta    snssvnvtqv    gfgnnatahq    y (SEQ ID NO: 1)

In some embodiments, "CsgA" refers to an *E. coli* CsgA. In some embodiments, "CsgA" refers to a polypeptide having at least 80% homology to SEQ ID NO: 1 (e.g., 80% or greater homology, 90% or greater homology, or 95% or greater homology), e.g. naturally occurring mutations or variants of CsgA, homologs of CsgA, or engineered mutations or variants of CsgA. In some embodiments, CsgA refers to a polypeptide comprising an amino acid sequence having at least 80%, 81%, 82%, 83% 84%, 85%, 86%, 87%, 88%, 89%, 90%, 91%, 92%, 93%, 94%, 95%, 96%, 97%, 98%, 99%, or 100% identity to the amino acid sequence of SEQ ID NO: 1. In some embodiments, CsgA refers to a polypeptide comprising an amino acid sequence having at least 80%, 81%, 82%, 83% 84%, 85%, 86%, 87%, 88%, 89%, 90%, 91%, 92%, 93%, 94%, 95%, 96%, 97%, 98%, 99%, or 100% homology to the amino acid sequence of SEQ ID NO: 1. The activity polypeptide may be directly connected to the CsgA polypeptide or be connected via a linker at either the C-terminus or the N-terminus or both of the CsgA polypeptide. CsgA within the scope of the present disclosure includes an amyloid domain which self-assembles into an amyloid structure. According to certain aspects, a linker may be attached to either the C-terminus or the N-terminus or separate linkers may be attached to both the C terminus and the N terminus of the CsgA.

In some embodiments, the CsgA fusion protein comprises a mucoadhesive polypeptide. Any mucoadhesive polypeptide known in the art may be fused to a CsgA polypeptide. Without wishing to be bound by any particular theory, CsgA fusion proteins comprising a mucoadhesive polypeptide are able to attach to a mucosa (e.g., a mammalian mucosal surface). The trefoil factors (TFFs) are a family of human cytokines that exhibit specific binding affinity for various mucins. In some embodiments, the mucoadhesive polypeptide is a polypeptide capable of specifically binding to a mucin. In some embodiments, the mucoadhesive polypeptide is selected from the group consisting of trefoil factor 1 (TFF1), trefoil factor 2 (TFF2), trefoil factor 3 (TFF3), and a MAM domain.

The CsgA polypeptide may comprise a mucoadhesive polypeptide described in Table 1, which provides the amino acid sequences thereof.

TABLE 1

Exemplary Mucoadhesive Polypeptides

| Mucoadhesive polypeptide | Amino Acid Sequence |
|---|---|
| Trefoil Factor 1 (TFF1) | EAQTETCTVAPRERQNCGFPGVTPSQCANKGCC FDDTVRGVPWCFYPNTIDVPPEEECEF (SEQ ID NO: 2) |
| Trefoil Factor 2 (TFF2) | EKPSPCQCSRLSPHNRTNCGFPGITSDQCFDNGC CFDSSVTGVPWCFHPLPKQESDQCVMEVSDRRN CGYPGISPEECASRKCCFSNFIFEVPWCFFPKSVE DCHY (SEQ ID NO: 3) |
| Trefoil Factor 3 (TFF3) | EEYVGLSANQCAVPAKDRVDCGYPHVTPKECN NRGCCFDSRIPGVPWCFKPLQEAECTF (SEQ ID NO: 4) |
| MAM domain | MMMPANYSVIAENEMTYVNGGANFIDAIGAVT APIWTLDNVKTFNTNIVTLVGNTFLQSTINRTIGV LFSGNTTWKEVGNIGKNLFGTNVKGNPIEKNNF GDYAMNALGIAAAVYNLGVAPTKNTVKETEVK FTV (SEQ ID NO: 5) |

In some embodiments, the mucoadhesive polypeptide is TFF1. In some embodiments, the CsgA fusion protein comprises a mucoadhesive polypeptide having at least 80%, 81%, 82%, 83% 84%, 85%, 86%, 87%, 88%, 89%, 90%, 91%, 92%, 93%, 94%, 95%, 96%, 97%, 98%, 99%, or 100% identity to the amino acid sequence of SEQ ID NO: 2. In some embodiments, the CsgA fusion protein comprises a mucoadhesive polypeptide having at least 80%, 81%, 82%, 83% 84%, 85%, 86%, 87%, 88%, 89%, 90%, 91%, 92%, 93%, 94%, 95%, 96%, 97%, 98%, 99%, or 100% homology to the amino acid sequence of SEQ ID NO: 2.

In some embodiments, the mucoadhesive polypeptide is TFF2. In some embodiments, the CsgA fusion protein comprises a mucoadhesive polypeptide having at least 80%, 81%, 82%, 83% 84%, 85%, 86%, 87%, 88%, 89%, 90%, 91%, 92%, 93%, 94%, 95%, 96%, 97%, 98%, 99%, or 100% identity to the amino acid sequence of SEQ ID NO: 3. In some embodiments, the CsgA fusion protein comprises a mucoadhesive polypeptide having at least 80%, 81%, 82%, 83% 84%, 85%, 86%, 87%, 88%, 89%, 90%, 91%, 92%, 93%, 94%, 95%, 96%, 97%, 98%, 99%, or 100% homology to the amino acid sequence of SEQ ID NO: 3.

In some embodiments, the mucoadhesive polypeptide is TFF3. In some embodiments, the CsgA fusion protein comprises a mucoadhesive polypeptide having at least 80%, 81%, 82%, 83% 84%, 85%, 86%, 87%, 88%, 89%, 90%, 91%, 92%, 93%, 94%, 95%, 96%, 97%, 98%, 99%, or 100% identity to the amino acid sequence of SEQ ID NO: 4. In some embodiments, the CsgA fusion protein comprises a mucoadhesive polypeptide having at least 80%, 81%, 82%, 83% 84%, 85%, 86%, 87%, 88%, 89%, 90%, 91%, 92%, 93%, 94%, 95%, 96%, 97%, 98%, 99%, or 100% homology to the amino acid sequence of SEQ ID NO: 4.

In some embodiments, the mucoadhesive polypeptide is a MAM domain. In some embodiments, the CsgA fusion protein comprises a mucoadhesive polypeptide having at least 80%, 81%, 82%, 83% 84%, 85%, 86%, 87%, 88%, 89%, 90%, 91%, 92%, 93%, 94%, 95%, 96%, 97%, 98%, 99%, or 100% identity to the amino acid sequence of SEQ ID NO: 5. In some embodiments, the CsgA fusion protein comprises a mucoadhesive polypeptide having at least 80%, 81%, 82%, 83% 84%, 85%, 86%, 87%, 88%, 89%, 90%, 91%, 92%, 93%, 94%, 95%, 96%, 97%, 98%, 99%, or 100% homology to the amino acid sequence of SEQ ID NO: 5.

In some embodiments, the activity polypeptide is a porin. In some embodiments, the activity polypeptide is an *E. coli* porin. In some embodiments, the CsgA fusion protein comprises an activity polypeptide having at least 80%, 81%, 82%, 83% 84%, 85%, 86%, 87%, 88%, 89%, 90%, 91%, 92%, 93%, 94%, 95%, 96%, 97%, 98%, 99%, or 100% identity to the amino acid sequence of SEQ ID NO: 6. In some embodiments, the CsgA fusion protein comprises an activity polypeptide having at least 80%, 81%, 82%, 83% 84%, 85%, 86%, 87%, 88%, 89%, 90%, 91%, 92%, 93%, 94%, 95%, 96%, 97%, 98%, 99%, or 100% homology to the amino acid sequence of SEQ ID NO: 6.

In some embodiments, the activity polypeptide is a ribosomal protein. In some embodiments, the activity polypeptide is ribosomal protein S6. In some embodiments, the CsgA fusion protein comprises an activity polypeptide having at least 80%, 81%, 82%, 83% 84%, 85%, 86%, 87%, 88%, 89%, 90%, 91%, 92%, 93%, 94%, 95%, 96%, 97%, 98%, 99%, or 100% identity to the amino acid sequence of SEQ ID NO: 7. In some embodiments, the CsgA fusion protein comprises an activity polypeptide having at least 80%, 81%, 82%, 83% 84%, 85%, 86%, 87%, 88%, 89%, 90%, 91%, 92%, 93%, 94%, 95%, 96%, 97%, 98%, 99%, or 100% homology to the amino acid sequence of SEQ ID NO: 7.

In some embodiments, the activity polypeptide is a plastocyanin. In some embodiments, the CsgA fusion protein comprises an activity polypeptide having at least 80%, 81%, 82%, 83% 84%, 85%, 86%, 87%, 88%, 89%, 90%, 91%, 92%, 93%, 94%, 95%, 96%, 97%, 98%, 99%, or 100% identity to the amino acid sequence of SEQ ID NO: 8. In some embodiments, the CsgA fusion protein comprises an activity polypeptide having at least 80%, 81%, 82%, 83% 84%, 85%, 86%, 87%, 88%, 89%, 90%, 91%, 92%, 93%, 94%, 95%, 96%, 97%, 98%, 99%, or 100% homology to the amino acid sequence of SEQ ID NO: 8.

TABLE 2

Exemplary activity polypeptides

| Activity Polypeptide | Amino Acid Sequence |
|---|---|
| *E. coli* porin | AEIYNKDGNKLDVYGKVKAMHYMSDNASKDGDQSYI RFGFKGETQINDQLTGYGRWEAEFAGNKAESDTAQQK TRLAFAGLKYKDLGSFDYGRNLGALYDVEAWTDMFPE FGGDSSAQTDNFMTKRASGLATYRNTDFFGVIDGLNL TLQYQGKNENRDVKKQNGDGFGTSLTYDFGGSDFAIS GAYTNSDRTNEQNLQSRGTGKRAEAWATGLKYDANNI YLATFYSETRKMTPITGGFANKTQNFEAVAQYQFDFG LRPSLGYVLSKGKDIEGIGDEDLVNYIDVGATYYFNK NMAFVDYKINQLDSDNKLNINNDDIVAVGMTYQF (SEQ ID NO: 6) |
| ribosomal protein S6 | MKLNISFPATGCQKLIEVDDERKLRTFYEKRMATEVAA DALGEEWKGYVVRISGGNDKQGFPMKQGVLTHGRVRL LLSKGHSCYRPRRTGERKRKSVRGCIVDANLSVLNLV IVKKGEKDIPGLTDTTVPRRLGPKRASRIRKLFNLSK EDDVRQYVVRKPLNKEGKKPRTKAPKIQRLVTPRVLQ HKRRRIALKKQRTKKNKEEAAEYAKLLAKRMKEAKEK RQEQIAKRRRLSSLRASTSKSESSQK (SEQ ID NO: 7) |

TABLE 2 -continued

Exemplary activity polypeptides

| Activity Polypeptide | Amino Acid Sequence |
|---|---|
| plastocyanin | MISSLRSALSACFALLLVLAFGVASAQAKTVEVKLGTD AGMLAFEPSSVTISTGDSVKFVNNKLAPHNAVFEGHEE LSHPDLAFAPGESWQETFTEAGTYDYYCEPHRGAGMV GKVVVN (SEQ ID NO: 8) |

In some embodiments, the CsgA fusion protein comprises a polypeptide tag. Multiple polypeptide tags are known in the art and can be used as described herein. The polypeptide tag may be used to separate and/or purify the CsgA fusion protein. The polypeptide tag may also be used to detect the CsgA fusion protein. The nucleic acid sequence encoding the polypeptide tag may be located, in-frame, at any position in the open reading frame of the heterologous nucleic acid encoding the CsgA fusion protein. In some embodiments, the nucleic acid sequence encoding the polypeptide tag is upstream from the nucleic acid encoding the CsgA fusion protein. In some embodiments, the nucleic acid sequence encoding the polypeptide tag is located downstream from the nucleic acid encoding the CsgA fusion protein. In some embodiments, the polypeptide tag is located N-terminal to the CsgA fusion protein. In some embodiments, the polypeptide tag is located C-terminal to the CsgA fusion protein. In some embodiments, the polypeptide tag is located between the CsgA polypeptide and the activity polypeptide of the CsgA fusion protein. In some embodiments, the polypeptide tag is a poly-histidine tag, a myc tag a FLAG tag, a hemagglutinin (HA) tag, or a V5 tag. In some embodiments, the CsgA fusion protein comprises more than one polypeptide tag. Exemplary polypeptide tags for use as described herein include, but are not limited to, the polypeptide tags shown in Table 3.

TABLE 3

Exemplary polypeptide tags

| Tag | Epitope |
|---|---|
| CBP | KRRWKKNFIAVSAANRFKKISSSGAL (SEQ ID NO: 9) |
| FLAG | DYKDDDD (SEQ ID NO: 10) or DYKDDDDK (SEQ ID NO: 11) or DYKDDDK (SEQ ID NO: 12) |
| HA | YPYDVPDYA (SEQ ID NO: 13) or YAYDVPDYA (SEQ ID NO: 14) or YDVPDYASL (SEQ ID NO: 15) |
| Myc | EQKLISEEDL (SEQ ID NO: 16) |
| poly His | HHHHHH (SEQ ID NO: 17) |
| S-tag | KETAAAKFERQHMDS (SEQ ID NO: 18) |
| V5 | GKPIPNPLLGLDST (SEQ ID NO: 19) |

In some embodiments, the CsgA fusion protein expressed by the engineered bacterium described herein comprises a polypeptide linker. In some embodiments, the polypeptide linker is one, two, three, four, five, six, seven, eight, nine, ten, eleven, twelve, thirteen, fourteen, fifteen, sixteen, seventeen, eighteen, nineteen, twenty, twenty-five, thirty, thirty-five, forty, forty-five, fifty, or more amino acids in length. In some embodiments, the polypeptide linker is twelve, twenty-four, thirty-six, forty-eight, sixty, seventy-two, eighty-four, or ninety-six amino acids in length. In some embodiments, the polypeptide linker is N-terminus of the protein. In some embodiments, the polypeptide linker is C-terminus of the protein. In some embodiments, the polypeptide linker is located between the CsgA polypeptide and the activity polypeptide of the CsgA fusion protein. In some embodiments, the polypeptide linker is flexible. In some embodiments, the polypeptide linker is rigid.

In some embodiments, the bacterium comprises a genetic modification in a csgA gene or a csgB gene. In some embodiments, the genetic modification is a point mutation, a partial deletion, or a knockout of the gene. In some embodiments, the bacterium does not transcribe or translate an mRNA encoding CsgA. In some embodiments, the bacterium does not express CsgA. In some embodiments, the bacterium does not transcribe or translate an mRNA encoding CsgB. In some embodiments, the bacterium does not express CsgB. In some embodiments, the bacterium comprises a deletion in the csgA gene. In some embodiment, the bacterium comprises a deletion of a curli operon. In some embodiments, the bacterium comprises a deletion of one or more endogenous csg genes. In some embodiments, the bacterium comprises a deletion of csgA. In some embodiments, the bacterium comprises a deletion of csgB. In some embodiments, the bacterium comprises a deletion of csgC. In some embodiments, the bacterium comprises a deletion of csgD. In some embodiments, the bacterium comprises a deletion of csgB and csgD. In some embodiments, the bacterium comprises a deletion of csgE. In some embodiments, the bacterium comprises a deletion of csgF. In some embodiments, the bacterium comprises a deletion of csgG. In some embodiments, the bacterium comprises a deletion of the csgBAC operon. In some embodiments, the bacterium comprises a deletion of the csgDEFG operon. In some embodiments, the bacterium comprises a deletion of the csgBAC and csgDEFG operons.

Many plasmids (also referred to as "vectors" herein) useful for transferring genes into bacterial cells are available. The plasmids may be episomal or may be integrated into the bacterial cell's genome through homologous recombination or random integration. In some embodiments, is an expression vector. A plasmid can be viral or non-viral. Plasmids for use as described herein can include, but are not limited to, pBR322, pBR325, pACYC177, pACYC184, pUC8, pUC9, pUC18, pUC19, pLG339, pR290, pKC37, pKC101, SV 40, pBluescript II SK+/– or KS+/–(see "Stratagene Cloning Systems" Catalog (1993) from Stratagene, La Jolla, Calif, which is hereby incorporated by reference), pQE, pIH821, pGEX, pET series (see Studier et al. (1990) "Use of T7 RNA Polymerase to Direct Expression of Cloned Genes," Gene Expression Technology 185, which is hereby incorporated by reference in its entirety).

The expression of any of the genes incorporated into the engineered bacterium described herein may be regulated using any promoter known in the art. In some embodiments, the promoter is a constitutive promoter. In some embodiments, the promoter is an inducible promoter. An "inducible promoter" may be one that is characterized by initiating or enhancing transcriptional activity when in the presence of, influenced by, or contacted by an inducer or inducing agent than when not in the presence of, under the influence of, or in contact with the inducer or inducing agent. An "inducer" or "inducing agent" may be endogenous, or a normally exogenous compound or protein that is administered in such a way as to be active in inducing transcriptional activity from the inducible promoter. In some embodiments, the inducer or inducing agent, e.g., a chemical, a compound or a protein, can itself be the result of transcription or expression of a nucleic acid sequence (e.g., an inducer can be a transcriptional repressor protein), which itself may be under the control or an inducible promoter. Non-limiting examples of inducible promoters include but are not limited to, the lac operon promoter, a nitrogen-sensitive promoter, an IPTG-inducible promoter, a salt-inducible promoter, tetracycline-inducible promoter, the lambda phage pL promoter, steroid-responsive promoters, rapamycin responsive promoters and the like. Inducible promoters for use in prokaryotic systems are well known in the art, see, e.g. the β-lactamase and lactose promoter systems (Chang et al. (1978) Nature 275: 615, which is incorporated herein by reference; Goeddel et al. (1979) Nature 281: 544, which is incorporated herein by reference), the arabinose promoter system, including the araBAD promoter (Guzman et al. (1992) J. Bacteriol. 174: 7716-28, which is incorporated herein by reference; Guzman et al. (1995) J. Bacteriol., 177: 4121-30, which is incorporated herein by reference; Siegele and Hu (1997) Proc. Natl. Acad. Sci. USA 94: 8168-72, which is incorporated herein by reference), the rhamnose promoter (Haldimann et al. (1998) J. Bacteriol. 180: 1277-86, which is incorporated herein by reference), the alkaline phosphatase promoter, a tryptophan (trp) promoter system (Goeddel (1980) Nucleic Acids Res., 8: 4057, which is incorporated herein by reference), the PLtetO-1 and Plac/are-1 promoters (Lutz and Bujard (1997) Nucleic Acids Res. 25: 1203-10, which is incorporated herein by reference), the phage lambda pL promoter system and pR promoter system (Simmons et al. (1984) Gene 28(1): 55-64; Gilman and Love (2016) Biochem. Soc. Trans. 44(3): 731-7; and Valdez-Cruz et al. (2010) Microb. Cell Fact. 9: 18. which are incorporated herein by reference), and hybrid promoters such as the tac promoter (see deBoer et al. (1983) Proc. Natl. Acad. Sci. USA 80: 21-5, which is incorporated herein by reference).

An inducible promoter useful in the methods and systems as disclosed herein can be induced by one or more physiological conditions, such as changes in pH, temperature, radiation, osmotic pressure, saline gradients, cell surface binding, and the concentration of one or more extrinsic or intrinsic inducing agents. The extrinsic inducer or inducing agent may comprise amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones, and combinations thereof. In specific embodiments, the inducible promoter is activated or repressed in response to a change of an environmental condition, such as the change in concentration of a chemical, metal, temperature, radiation, nutrient or change in pH. Thus, an inducible promoter useful in the methods and systems as disclosed herein can be a phage inducible promoter, nutrient inducible promoter, temperature inducible promoter, radiation inducible promoter, metal inducible promoter, hormone inducible promoter, steroid inducible promoter, and/or hybrids and combinations thereof. Appropriate environmental inducers can include, but are not limited to, exposure to heat (i.e., thermal pulses or constant heat exposure), various steroidal compounds, divalent cations (including $Cu^{2+}$, $Co^{2+}$, and $Zn^{2+}$), galactose, arabinose, anhydrotetracycline (ATc), tetracycline, IPTG (isopropyl-β-D thiogalactoside), as well as other naturally occurring and synthetic inducing agents and gratuitous inducers.

Inducible promoters useful in the methods and systems as disclosed herein also include those that are repressed by "transcriptional repressors" that are subject to inactivation by the action of environmental, external agents, or the product of another gene. Such inducible promoters may also be termed "repressible promoters" where it is required to distinguish between other types of promoters in a given module or component of the biological switch converters described herein. Preferred repressors for use in the present invention are sensitive to inactivation by physiologically benign agent. Thus, where a lac repressor protein is used to control the expression of a promoter sequence that has been engineered to contain a lacO operator sequence, treatment of the host cell with IPTG will cause the dissociation of the lac repressor from the engineered promoter containing a lacO operator sequence and allow transcription to occur. Similarly, where a tet repressor is used to control the expression of a promoter sequence that has been engineered to contain a tetO operator sequence, treatment of the host cell with tetracycline, or the tetracycline analog anhydrotetracycline (ATc), will cause the dissociation of the tet repressor from the engineered promoter and allow transcription of the sequence downstream of the engineered promoter to occur.

Bacteria for use in the methods and compositions described herein can be of any species. Preferably, the bacteria are of a species and/or strain which is amenable to culture and genetic manipulation. In some embodiments, the bacterium is a gram-positive bacterium. In some embodiments, the bacterium is a gram-negative bacterium. In some embodiments, the bacterium is a probiotic. In some embodiments, the bacterium is Generally Recognized as Safe (GRAS) by a regulatory authority. In some embodiments, the bacterium is pathogenic. In some embodiments, the bacterium is non-pathogenic. In some embodiments, the bacterium is an attenuated pathogenic bacterium. In some embodiments, the parental strain of the bacterium used herein is of a strain optimized for protein expression.

Non-limiting examples of bacterial species and strains suitable for use in the present technologies include *Escherichia coli, E. coli* BL21, *E. coli* Tuner, *E. coli* Rosetta, *E. coli* JM101, and derivatives of any of the foregoing. In one embodiment, the bacterium is of the *E. coli* Nissle 1917 strain. Other non-pathogenic bacterial strains known to those of skill in the art such as MG1655, K12-derived strains, and the like, may also be used.

Compositions of the Invention

Provided herein are biologic hydrogels comprising a curli fiber. In some embodiments, the biologic hydrogel comprises a curli fiber produced from a wild-type microorganism. In some embodiments, the biologic hydrogel comprises a curli fiber produced from a genetically engineered microorganism.

In some embodiments, the biologic hydrogel comprises a curli fiber, wherein the curli fiber comprises a CsgA protein. In some embodiments, the CsgA protein is an *E. coli* CsgA protein. In some embodiments, the CsgA protein is a wild-type CsgA protein. In some embodiments, the CsgA protein in an engineered CsgA protein (e.g., an engineered CsgA fusion protein).

In some embodiments, the biologic hydrogel comprises a curli fiber, wherein the curli fiber comprises an engineered CsgA fusion protein, wherein the CsgA fusion protein comprises a CsgA polypeptide fused to an activity polypeptide. The activity polypeptide may be any polypeptide of interest. For example, in some embodiments the activity polypeptide is a mucoadhesive polypeptide. In some embodiments, the activity polypeptide is a pore-forming polypeptide (e.g., a porin). In some embodiments, the activity polypeptide is a ribosomal polypeptide (e.g., ribosomal protein S6 (RPS6)). In some embodiments, the activity polypeptide is a metal binding polypeptide (e.g., a copper-binding polypeptide, a gold-binding polypeptide, or a nickel-binding polypeptide). In some embodiments, the activity polypeptide is a plastocyanin.

In some embodiments, the biologic hydrogel comprises a curli fiber, wherein the curli fiber comprises an engineered CsgA fusion protein, wherein the CsgA fusion protein comprises a CsgA polypeptide fused to an mucoadhesive polypeptide. Without wishing to be bound by any particular theory, the biologic hydrogels described herein are capable of binding to a mucosa which allows for their use in a multitude of applications, including for example, therapeutic applications whereby the hydrogels can attach to a mucosal surface in vivo (e.g., an intestinal lining) allowing for specific targeting of the hydrogel. Thus, for example, the hydrogels described herein may be advantageously used for the delivery of a drug to a mucosal tissue.

In some embodiments, the biologic hydrogel comprises a CsgA fusion protein comprising a CsgA polypeptide (e.g., an *E. coli* CsgA polypeptide) and an activity polypeptide. In some embodiments, the activity polypeptide is a mucoadhesive polypeptide selected from the group consisting of: trefoil factor 1 (TFF1), trefoil factor 2 (TFF2), trefoil factor 3 (TFF3), and a MAM domain. In some embodiments, the CsgA fusion protein comprises a CsgA polypeptide and TFF1. In some embodiments, the CsgA fusion protein comprises a CsgA polypeptide and TFF2. In some embodiments, the CsgA fusion protein comprises a CsgA polypeptide and TFF3. In some embodiments, the CsgA fusion protein comprises a CsgA polypeptide and a MAM domain. In some embodiments, the biologic hydrogel comprises a CsgA fusion protein comprising a CsgA polypeptide and an activity polypeptide, wherein the activity polypeptide is selected from the group consisting of a porin, a ribosomal protein, or a plastocyanin. In some embodiments, the CsgA fusion protein comprises a CsgA polypeptide and *E. coli* porin (SEQ ID NO: 6). In some embodiments, the CsgA fusion protein comprises a CsgA polypeptide and ribosomal protein S6 (SEQ ID NO: 7). In some embodiments, the CsgA fusion protein comprises a CsgA polypeptide and plastocyanin (SEQ ID NO: 8).

In some embodiments the biologic hydrogel comprises a microbe. In some embodiments, the biologic hydrogel comprises a bacterial cell, a mammalian cell, a virus, a prion, a protozoan, or a fungus. In some embodiments, the bacterial cell is a live bacterial cell. In some embodiments, the biologic hydrogels described herein are capable of supporting the growth of a cell thereby allowing for the cell therein to continuously grow, and as applicable, produce a substance of interest (e.g., a therapeutic polypeptide), thereby allowing for the continual general of the substance of interest. In some embodiments, the biologic hydrogel comprises a dead cell (e.g., a dead bacterial cell). In some embodiments, the biologic hydrogel comprises a non-pathogenic cell (e.g., a non-pathogenic bacterial cell). In some embodiments, the biologic hydrogel comprises an bacterial cell of the species *E. coli*.

In some embodiments, the biologic hydrogel comprises a wild-type bacterial cell. In some embodiments, the biologic hydrogel comprises an engineered bacterial cell. In some embodiments, the biologic hydrogel comprises an engineered bacterial cell comprising a heterologous nucleic acid comprising a heterologous gene encoding an engineered CsgA fusion protein, wherein the CsgA fusion protein comprises a CsgA polypeptide fused to an activity polypeptide (e.g. a mucoadhesive polypeptide). In some embodiments, the engineered bacterial cell is an *E. coli* comprising a csgBACEFG operon or a csgACEFG operon. In some embodiments, the engineered bacterial cell is an *E. coli* strain comprising a deletion in an endogenous csgB gene. In some embodiments, the engineered bacterial cell is an *E. coli* strain comprising a deletion in an endogenous csgD gene. In some embodiments, the engineered bacterial cell comprises a heterologous nucleic acid comprising a heterologous gene encoding a polypeptide selected from the group consisting of an extracellular matrix component, a therapeutic polypeptide, a mucoadhesive polypeptide, a cytokine, an antibody, an antibody mimetic polypeptide, and an enzyme.

The biologic hydrogel may comprise additional components. In some embodiments, the biologic hydrogel comprises one or more of a nucleic acid, an extracellular matrix component, a polysaccharide, a metabolite, a metal ion, a nanoparticle, a polypeptide, cellulose, a vitamin, a nutraceutical, and a detectable compound. In some embodiments, the biologic hydrogel comprises a detectable compound comprising a fluorescent moiety, a radioactive moiety, a colorimetric dye, a fluorescent dye, a luminescent dye, a magnetic resonance imaging (MRI) contrast agent, a CT contrast agent, a PET contrast agent, or an ultrasound contrast agent.

In some embodiments, the curli fibers within the biologic hydrogel are fully crosslinked. In some embodiments, the curli fibers within the biologic hydrogel are partially cross-linked. Crosslinking agents that may be used to cross-link the curli fibers and/or any additional cross-linkable component of the curli fiber includes urea, SDS, and guanidine hydrochloride.

In some embodiments, the biologic hydrogel comprises a diatom. In some embodiments, the biologic hydrogel comprises a carbon nanotube.

In some embodiments, the biologic hydrogel is dehydrated. In some embodiments, the biologic hydrogel has been rehydrated (e.g., using water or a buffered solution).

In some embodiments the biologic hydrogel described herein are suitable for use in an application selected from the group consisting of biocatalysis, chemical production, filtration, isolation of molecules from an aqueous solution, water filtration, bioremediation, nanoparticle synthesis, nanowire synthesis, display of optically active materials, surface coating, structural reinforcement of an object, and delivery of a therapeutic agent. In some embodiments, the biologic hydrogel described herein is suitable for use as a therapeutic biomaterial, a biological scaffold, a delivery system for therapeutic agents, a biosensor, a biocatalyst, a coating, an electronically-conductive material.

In some embodiments, the biologic hydrogel described herein is injectable. In some embodiments, the biologic hydrogel described herein is sprayable. In some embodiments, the biologic hydrogel described herein may be aerosolized.

Also provided is an article of manufacture comprising a biologic hydrogel described herein. In some embodiments, the article is a drug delivery device, a coating, a 3D printed composition, or a patch. In some embodiments, the drug delivery device is a syringe, an autoinjector, a drug delivery patch. In some embodiments, the article of manufacture is coated with the biologic hydrogel. In some embodiments, the article of manufacture comprises a vessel containing the biologic hydrogel.

Also provided is a thin film comprising a biologic hydrogel described herein. In some embodiments, the thin film is a dehydrated thin film. In some embodiments, the thin film is hydrophilic. In some embodiments, the thin film is hydrophobic.

Advantageously, thin films formed using the methods and compositions described herein may be formed in any desired shape or form, for example by using a mold.

In addition, thin films described herein may comprises a surface having a pattern. Without wishing to be bound by any particular theory, the thin films described herein may be formed by overlaying a non-dehydrated biological hydrogel described herein over a structured surface and drying (e.g., air drying) the biologic hydrogel. The formed thin film readily imprints the pattern of the surface over which it was overlayed. In some embodiments, the pattern is a geometric pattern. In some embodiments, the pattern is a repetitive pattern. In some embodiments, the biologic hydrogel is overlayed over a porous structure and dried. In some embodiments, the porous structure comprises wood, nylon, paper, a metal mesh (e.g., a thin metal mesh). In some embodiments, the thin film is flexible. In some embodiments, the thin film is rigid.

In another aspect, provided herein are methods of assembling a three-dimensional structure comprising hydrating a first thin film described herein at a first location, attaching a second thin film to the hydrated first location of the first thin film thereby forming an assembly of two thin films, and drying the assembly of the two thin films, thereby forming a three-dimensional structure.

In another aspect, provided herein are particles comprising a biologic hydrogel described herein. In some embodiments, the particles are obtained by fractionating a biological hydrogel described herein. In some embodiments, the particles are obtained by sonicating a biologic hydrogel described herein. In some embodiments, the particles are obtained by spraying a biologic hydrogel described herein. In some embodiments, the particles are obtained by emulsifying a biologic hydrogel described herein. In some embodiments, the particles are obtained by extrusion of a biologic hydrogel described herein. In some embodiments, the particle is a macroparticle. In some embodiments, the particle is a microparticle. In some embodiments, the particle is a nano-particle. In some embodiments, the particle is of a size range from about 1 nm to about 1 µm. In some embodiments, the particle is of a size range from about 50 nm to about 500 nm. In some embodiments, the particle is of a size range from about 1 nm to about 50 nm. In some embodiments, the particle is of a size range from about 1 nm to about 10 nm. In some embodiments, the particle is of a size range from about 1 nm to about 100 nm. In some embodiments the particle is 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm, 60 nm, 61 nm, 62 nm, 63 nm, 64 nm, 65 nm, 66 nm, 67 nm, 68 nm, 69 nm, 70 nm, 71 nm, 72 nm, 73 nm, 74 nm, 75 nm, 76 nm, 77 nm, 78 nm, 79 nm, 80 nm, 81 nm, 82 nm, 83 nm, 84 nm, 85 nm, 86 nm, 87 nm, 88 nm, 89 nm, 90 nm, 91 nm, 92 nm, 93 nm, 94 nm, 95 nm, 96 nm, 97 nm, 98 nm, 99 nm, 100 nm, or more in size. In some embodiments, the particle is of a size range from about 1 µm to about 50% tin. In some embodiments, the particle is of a size range from about 1 µm to about 10 µm. In some embodiments, the particle is of a size range from about 1 µm to about 100 µm. In some embodiments the particle is 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 21 μm, 22 μm, 23 μm, 24 μm, 25 μm, 26 μm, 27 μm, 28 μm, 29 μm, 30 μm, 31 μm, 32 μm, 33 μm, 34 μm, 35 μm, 36 μm, 37 μm, 38 μm, 39 μm, 40 μm, 41 μm, 42 μm, 43 μm, 44 μm, 45 μm, 46 μm, 47 μm, 48 μm, 49 μm, 50 μm, 51 μm, 52 μm, 53 μm, 54 μm, 55 μm, 56 μm, 57 μm, 58 μm, 59 μm, 60 μm, 61 μm, 62 μm, 63 μm, 64 μm, 65 μm, 66 μm, 67 μm, 68 μm, 69 μm, 70 μm, 71 μm, 72 μm, 73 μm, 74 μm, 75 μm, 76 μm, 77 μm, 78 μm, 79 μm, 80 μm, 81 μm, 82 μm, 83 μm, 84 μm, 85 μm, 86 μm, 87 μm, 88 μm, 89 μm, 90 μm, 91 μm, 92 μm, 93 μm, 94 μm, 95 μm, 96 μm, 97 μm, 98 μm, 99 μm, 100 μm, or more in size.

Pharmaceutical compositions comprising a biologic hydrogel, a thin film, or a particle described herein are also provided. These pharmaceutical compositions may be used to diagnose, treat, manage, ameliorate, and/or prevent a disease or disorder, as described herein. Pharmaceutical compositions comprising a biologic hydrogel, a thin film, or a particle described herein, either alone or in combination with prophylactic agents, therapeutic agents, and/or pharmaceutically acceptable carriers are provided.

In some embodiments, a biologic hydrogel, thin film, or particle described herein comprises a drug or a diagnostic agent. Exemplary diagnostic agents are described, e.g., in WO 2016/164422, incorporated herein by reference in its entirety. In embodiments, methods of diagnosing a disease or disorder comprising use of a biologic hydrogel, thin film, or particle described herein can be performed, in part, using one or more diagnostic methods described in WO 2016/164422.

The pharmaceutical compositions described herein may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, Pa.). In some embodiments, the pharmaceutical compositions are subjected to tableting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The biologic hydrogels, thin films, or particles described herein may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, immediate-release, pulsatile-release, delayed-release, or sustained release). The composition may be administered once or more daily, weekly, or monthly.

The pharmaceutical compositions may comprise one or more pharmaceutically acceptable carriers, thickeners, diluents, buffers, buffering agents, surface active agents, neutral or cationic lipids, lipid complexes, nanoparticles, liposomes, penetration enhancers, carrier compounds, and other pharmaceutically acceptable carriers or agents. For example, the pharmaceutical composition may include, but is not limited to, the addition of calcium bicarbonate, sodium bicarbonate, calcium phosphate, various sugars and types of starch, cellulose derivatives, gelatin, vegetable oils, polyethylene glycols, and surfactants, including, for example, polysorbate 20. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc. The pharmaceutical compositions disclosed herein may be administered topically and formulated in the form of an ointment, cream, transdermal patch, lotion, gel, shampoo, spray, aerosol, solution, emulsion, or other form well-known to one of skill in the art. See, e.g., "Remington's Pharmaceutical Sciences," Mack Publishing Co., Easton, Pa. In an embodiment, for non-sprayable topical dosage forms, viscous to semi-solid or solid forms comprising a carrier or one or more excipients compatible with topical application and having a dynamic viscosity greater than water are employed. Suitable formulations include, but are not limited to, solutions, suspensions, emulsions, creams, ointments, powders, liniments, salves, etc., which may be sterilized or mixed with auxiliary agents (e.g., preservatives, stabilizers, wetting agents, buffers, or salts) for influencing various properties, e.g., osmotic pressure. Other suitable topical dosage forms include sprayable aerosol preparations wherein the active ingredient in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms. Examples of such additional ingredients are well known in the art.

The pharmaceutical compositions disclosed herein may be administered orally and formulated as tablets, pills, dragees, capsules, liquids, gels, syrups, slurries, suspensions, etc. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) or polyethylene glycol (PEG). Disintegrating agents may also be added, such as cross-linked polyvinylpyrrolidone, agar, alginic acid or a salt thereof such as sodium alginate.

Tablets or capsules can be prepared by conventional means with pharmaceutically acceptable excipients such as binding agents (e.g., pregelatinised maize starch, polyvinylpyrrolidone, hydroxypropyl methylcellulose, carboxymethylcellulose, polyethylene glycol, sucrose, glucose, sorbitol, starch, gum, kaolin, and tragacanth); fillers (e.g., lactose, microcrystalline cellulose, or calcium hydrogen phosphate); lubricants (e.g., calcium, aluminum, zinc, stearic acid, polyethylene glycol, sodium lauryl sulfate, starch, sodium benzoate, L-leucine, magnesium stearate, talc, or silica); disintegrants (e.g., starch, potato starch, sodium starch glycolate, sugars, cellulose derivatives, silica powders); or wetting agents (e.g., sodium lauryl sulphate). The tablets may be coated by methods well known in the art. A coating shell may be present, and common membranes include, but are not limited to, polylactide, polyglycolic acid, polyanhydride, other biodegradable polymers, alginate-polylysine-alginate (APA), alginate-polymethylene-co-guanidine-alginate (A-PMCG-A), hydroymethylacrylate-methyl methacrylate (HEMA-MMA), multilayered HEMA-MMA-MAA, polyacrylonitrilevinylchloride (PAN-PVC), acrylonitrile/sodium methallylsulfonate (AN-69), polyethylene glycol/poly pentamethylcyclopentasiloxane/polydimethylsiloxane (PEG/PD5/PDMS), poly N,N-dimethyl acrylamide (PDMAAm), siliceous encapsulates, cellulose sulphate/sodium alginate/polymethylene-co-guanidine (CS/A/PMCG), cellulose acetate phthalate, calcium alginate, k-carrageenan-locust bean gum gel beads, gellan-xanthan beads, poly(lactide-co-glycolides), carrageenan, starch poly-anhydrides, starch polymethacrylates, polyamino acids, and enteric coating polymers.

Liquid preparations for oral administration may take the form of solutions, syrups, suspensions, or a dry product for constitution with water or other suitable vehicle before use. Such liquid preparations may be prepared by conventional means with pharmaceutically acceptable agents such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of the biological hydrogel, thin film or particle described herein.

In some embodiments, the pharmaceutical composition is formulated for intraintestinal administration, intrajejunal administration, intraduodenal administration, intraileal administration, gastric shunt administration, or intracolic administration, via nanoparticles, nanocapsules, microcapsules, or microtablets, which are enterically coated or uncoated. The pharmaceutical compositions may also be formulated in rectal compositions such as suppositories or retention enemas, using, e.g., conventional suppository bases such as cocoa butter or other glycerides. The compositions may be suspensions, solutions, or emulsions in oily or aqueous vehicles, and may contain suspending, stabilizing and/or dispersing agents. In some embodiments, the pharmaceutical composition is suitable for administration to a mammalian subject (e.g., a domestic animal) In some embodiments, the pharmaceutical composition is suitable for administration to a non-mammalian subject. In some embodiments, the pharmaceutical composition is suitable for administration to a human subject.

The pharmaceutical compositions described herein may be administered intranasally, formulated in an aerosol form, spray, mist, or in the form of drops, and conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). Pressurized aerosol dosage units may be determined by providing a valve to deliver a metered amount. Capsules and cartridges (e.g., of gelatin) for use in an inhaler or insufflator may be formulated containing a powder mix of the compound and a suitable powder base such as lactose or starch.

The pharmaceutical compositions may be administered and formulated as depot preparations. Such long acting formulations may be administered by implantation or by injection, including intravenous injection, subcutaneous injection, local injection, direct injection, or infusion. For example, the compositions may be formulated with suitable polymeric or hydrophobic materials (e.g., as an emulsion in an acceptable oil) or ion exchange resins, or as sparingly soluble derivatives (e.g., as a sparingly soluble salt).

In some embodiments, disclosed herein are pharmaceutically acceptable compositions in single dosage forms. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, lozenge, etc. In alternate embodiments, a single dosage form may be administered over a period of time, e.g., by infusion.

Single dosage forms of the pharmaceutical composition may be prepared by portioning the pharmaceutical composition into smaller aliquots, single dose containers, single dose liquid forms, or single dose solid forms, such as tablets, granulates, nanoparticles, nanocapsules, microcapsules, microtablets, pellets, or powders, which may be enterically coated or uncoated. A single dose in a solid form may be reconstituted by adding liquid, typically sterile water or saline solution, prior to administration to a patient.

In other embodiments, the composition can be delivered in a controlled release or sustained release system. In one embodiment, a pump may be used to achieve controlled or sustained release. In another embodiment, polymeric materials can be used to achieve controlled or sustained release of the therapies of the present disclosure (see e.g., U.S. Pat. No. 5,989,463). Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

Methods of Making a Biologic Hydrogel

In another aspect, provide herein are methods of making a biologic hydrogel comprising contacting a composition comprising a bacterial cell (e.g., a bacterial cell culture) expressing a curli fiber with a surfactant, thereby creating a mixture; and incubating the mixture, thereby allowing the mixture to gelate; thereby making the biologic hydrogel. In some embodiments, the methods described herein advantageously allow for the formation of a biologic hydrogel directly from a microbial culture.

In some embodiments, the methods described herein further comprise concentrating the composition using centrifugation prior to contacting the composition with the surfactant.

In some embodiments, the methods further comprise concentrating the composition using filtration prior to contacting the composition with the surfactant.

In some embodiments, the methods further comprise contacting the composition with a solubilization agent prior to contacting the composition with the surfactant.

In some embodiments, the methods further comprise contacting the composition with a nuclease. Exposure to the nuclease will allow for the break-down or degradation of a nucleic acid present in the hydrogel. In some embodiments, the nuclease is a DNAse. In some embodiments, the nuclease is an RNAse.

In another aspect, provided herein is a method of making a biologic hydrogel comprising contacting a liquid composition comprising a bacterial cell that expresses a curli fiber with a solubilization agent, thereby creating a mixture; contacting the mixture with a filter; contacting the mixture with a surfactant; incubating the mixture, thereby allowing the mixture to gelate; and concentrating the mixture using filtration; thereby making the biologic hydrogel.

In some embodiments, the solubilization agent can be a denaturing solubilization agent, a non-denaturing solubilization agent, or a mild denaturing solubilization agent. In some embodiments, the solubilization agent can be, but is not limited to, guanidine, urea, DMSO, SDS, β-mercaptoethanol, or n-propanol. In some embodiments, the solubilization agent is any agent or reagent capable of inducing lysis of a microbial cell (e.g., a bacterial cell) including a lysis buffer, lysozyme, a base such as sodium hydroxide, and others. The concentration of the solubilization agent that is used may be varied, and without wishing to be bound by any particular theory, may affect the purity of the amyloid fibers that are ultimately obtained using the methods described herein. In some embodiments, the solubilization agent is used at a concentration capable of inducing lysis of a bacterial cell. One of ordinary skill may readily ascertain the concentration of the solubilization agent necessary in order to induce lysis of a bacterial cell. For example, when guanidine hydrochloride is the solubilization agent that is used in the methods described herein, the concentration of guanidine hydrochloride may range from 0.1-10 M. In some embodiments, the concentration of guanidine hydrochloride is about 0.1 M, about 0.2 M, about 0.3 M, about 0.4 M, about 0.5 M, about 1 M, about 2 M, about 3 M, about 4.0 M, about 5.0 M, about 6.0 M, about 7.0 M, about 8.0 M, about 9.0 M, about 10.0 M, or more.

In some embodiments, the methods described herein may be performed using vacuum filtration (e.g., using vacuum generated with a pump). In some embodiments, the methods described herein may be performed using gravity filtration. In some embodiments, the methods described herein may be performed using centrifugal filtration. In some embodiments, the methods described herein may be performed using filter plates for small scale purification. The filtration set-ups used in the methods described herein may include vacuum filtration holders, butchner funnels, tabletop filtration systems, and the like.

In some embodiments, the filter is a filter membrane, a mesh, or a porous cloth. In one embodiment, the filter membrane is polycarbonate, nylon, cellulose, polytetrafluoroethylene (Teflon™), polyethersulfone, polyvinylidene fluoride, or polyvinyidene chloride. In one embodiment, the filter membrane is a polycarbonate membrane. In one embodiment, the mesh is a metal mesh, a glass mesh, a ceramic mesh, a plastic mesh, or a polymer mesh.

In some embodiments, the filter membranes used in the presently disclosed methods may be, but are not limited to, polymer membranes made of polycarbonate, nylon, cellulose, Teflon™, polyethersulfone, polyvinylidene fluoride, polyvinyidene chloride, or other materials. In some embodiments, curli fiber aggregates can be filtered on cloths, or any other fabrics with pores of the appropriate size, as described herein. In some embodiments, curli fiber aggregates can be filtered on porous mesh with pores of the appropriate size, as described herein, such as, but not limited to, metal meshes, plastic meshes, glass meshes, ceramic meshes, or polymer meshes.

The filter membranes can have a pores of any shape or geometry. For example, in some embodiments, the pores can be circular. In other embodiments, the pores can be mesh-like. In some embodiments, the filter membranes can have pores of more than one shape or geometry.

The filter membrane may be of any geometric (e.g., circular, octagonal, rectangular, squared) or non-structured shape. The filter membrane may be of any size. For example, larger filters allow for scaling-up of the purification process.

In some embodiments, the surfactant can be an ionic surfactant or a non-ionic surfactant. In some embodiments, the surfactant can be, but is not limited to, SDS, 4-octylphenol polyethoxylate (also known as Triton X-100™), polyethylene glycol sorbitan monolaurate (also known as Tween® 20), polyethylene glycol sorbitan monooleate (also known as Tween® 80). For example, when the surfactant is SDS, a solution comprising 1% (w/v), 2%, 3%, 4%, 5%, 6%, 7%, 8%, 9%, 10% or more may be used. In some embodiments, the surfactant is SDS at a concentration of 5% (w/v).

In some embodiments, the methods further comprising air-drying the biologic hydrogel. In some embodiments, the air-drying is performed at room temperature for at least 2 hours, at least 3 hours, at least 4 hours, at least 5 hours, at least 6 hours, at least 12 hours, at least 24 hours, at least 36 hours, or more. In some embodiments, the methods further comprise lyophilizing the biologic hydrogel.

In some embodiments, the biologic hydrogel may be subjected to solvent exchange. In some embodiments, the solvent exchange is performed using water or a buffered solution (e.g., phosphate buffered solution). In some embodiments, the solvent exchange is performed using a low tension solvent.

In some embodiments, the method further comprises dehydrating the biologic hydrogel. In some embodiments, the method further comprises rehydrating the biologic hydrogel.

In some embodiments, the method further comprises imprinting the surface of the biologic hydrogel with a mold. In some embodiments, the mold is a nano mold. In some embodiments, the mold is a micro mold. In some embodiments, the mold comprises a pattern (e.g., a mesh or a structured surface). In some embodiments, the mold is a naturally occurring material.

In some embodiments, the filter membranes may be, but are not limited to, polymer membranes made of polycarbonate, nylon, cellulose, Teflon, polyethersulfone, polyvinylidene, fluoride, Polyvinyidene chloride, or other materials (e.g., chitin, chitosine, alginate). In some embodiments, the filter membrane can have pores of any size larger than the size of a bacterium and smaller than the size of an aggregate of curli fibers (approximately ~2 to 50 μm).

The methods described herein may be performed at a small scale (i.e., as a batch process) or may be adapted for large scale production of hydrogels.

EXAMPLES

Example 1: Preparation of Curli Nanofiber Hydrogels

Preparation of CsgA fusion protein: Different CsgA fusion proteins were created using techniques known to one of ordinary skill in the art. Generally, CsgA fusion proteins are created by fusing a CsgA protein, peptide or polypeptide that can partially or completely unfold under denaturing conditions (e.g., in the presence of denaturants such as urea or guanidine HCl). The following two CsgA fusion proteins were created: (1) a CsgA-TFF2 fusion protein; and (2) a CsgA-MAM fusion protein. One of ordinary skill in the art would know that the CsgA fusion proteins can be in either the C-terminal and N-terminal orientation. Further, a flexible linker (e.g., a glycine-serine linker (GSGGSGGSGGSG)x) (SEQ ID NO: 20) may be added to the N-terminus or the C-terminus of CsgA to create the fusion proteins.

Figure 3:
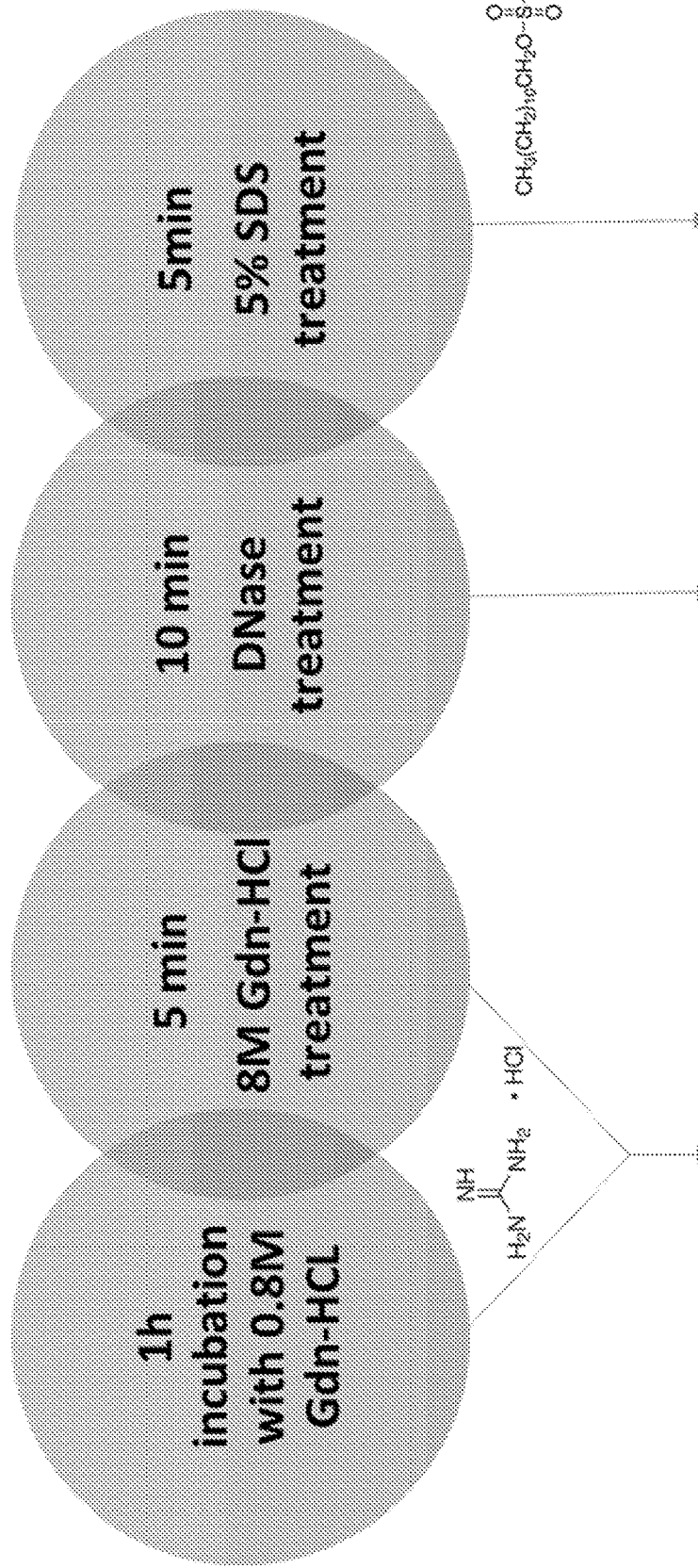
FIG. 3 depicts a scheme for the formation of curli nanofiber hydrogels.
Figure 4:
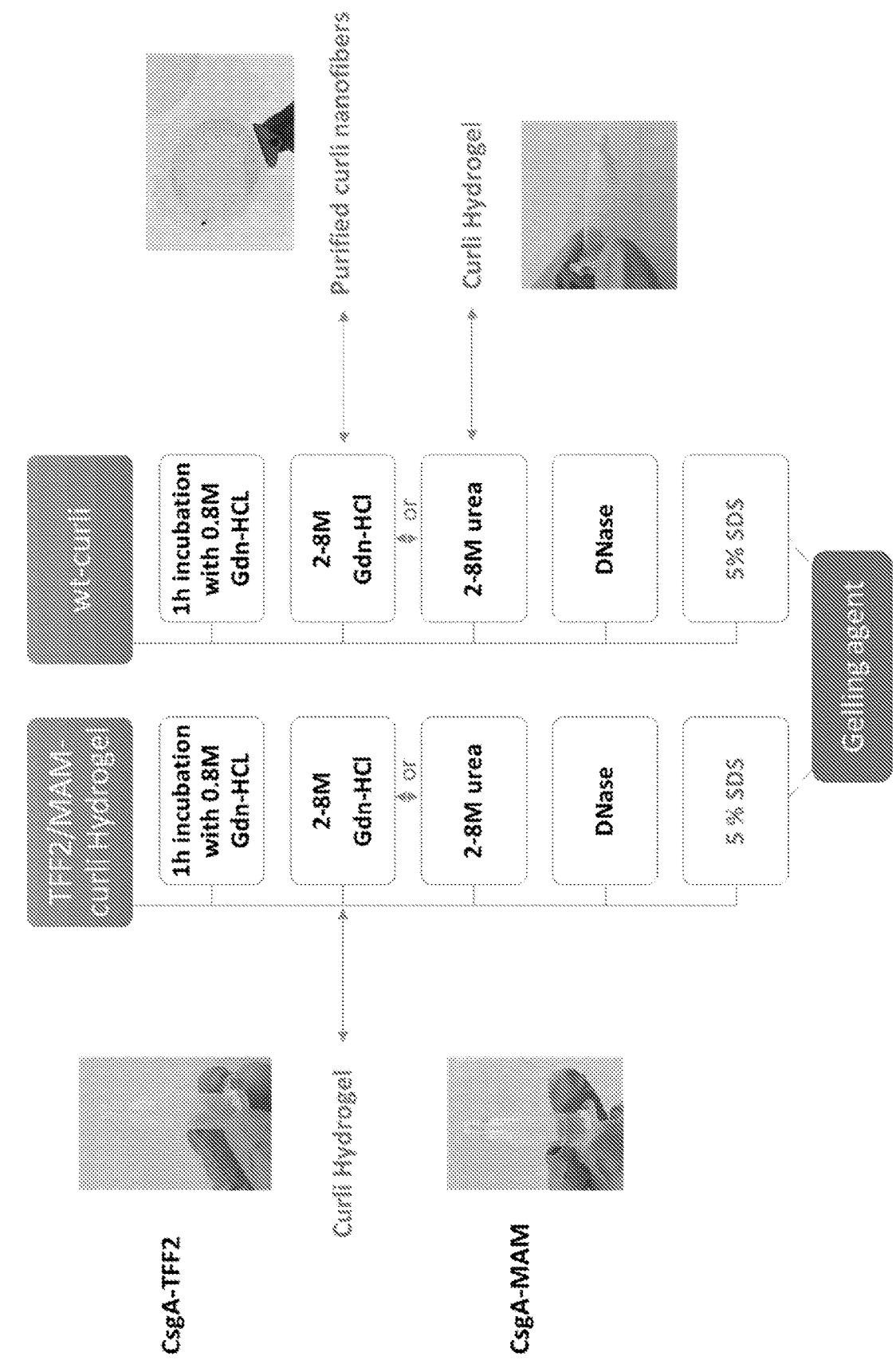
FIG. 4 compares schemes for the formation of (i) TFF2/MAM-based curli nanofiber hydrogels and (ii) wild-type-based curli nanofiber hydrogels.
Figure 5:
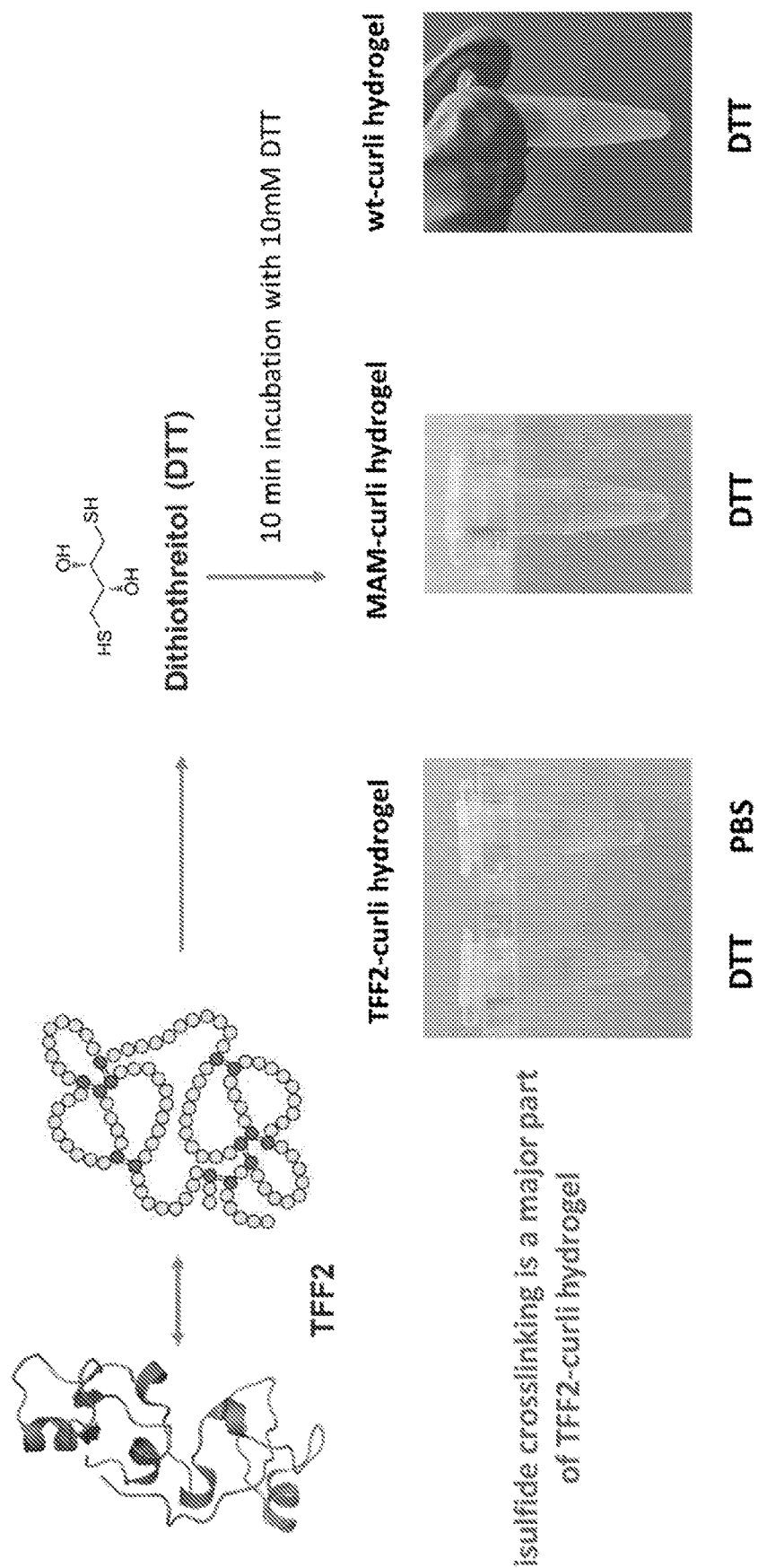
FIG. 5 shows the importance of disulfide crosslinking to the formation of TFF2-based curli nanofiber hydrogels.
Figure 9A:
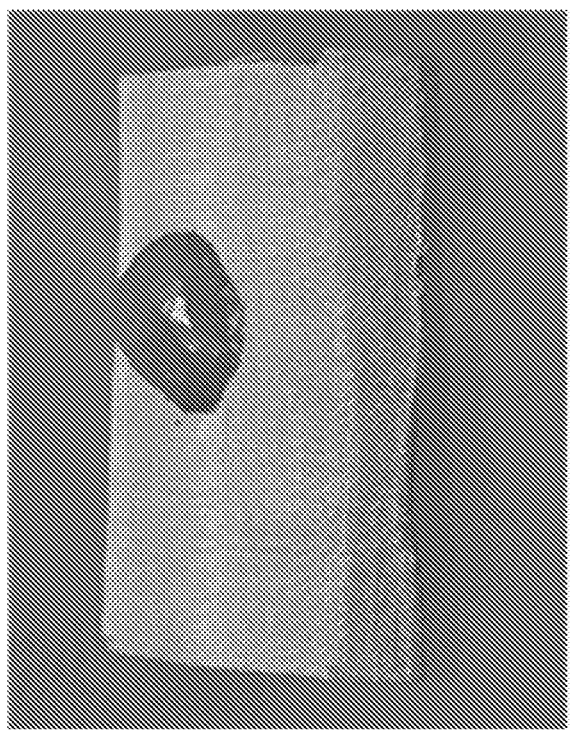
FIG. 9A is a photograph of a CsgA-TTF2-based biologic hydrogel transferred onto a fine metal mesh. The hydrogel was dried on the fine metal mesh substrate and removed from the substrate after drying.
Figure 9C:
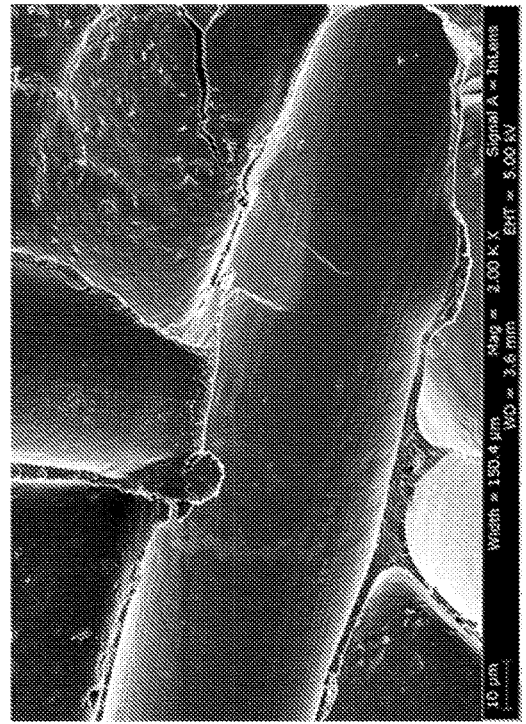
FIGS. 9B, 9C, 9D, and 9E depict the morphology of the CsgA-TTF2-based curli nanofiber film sample as observed by SEM. After removal, the film is imprinted with the pattern of the substrate.
Figure 9E:
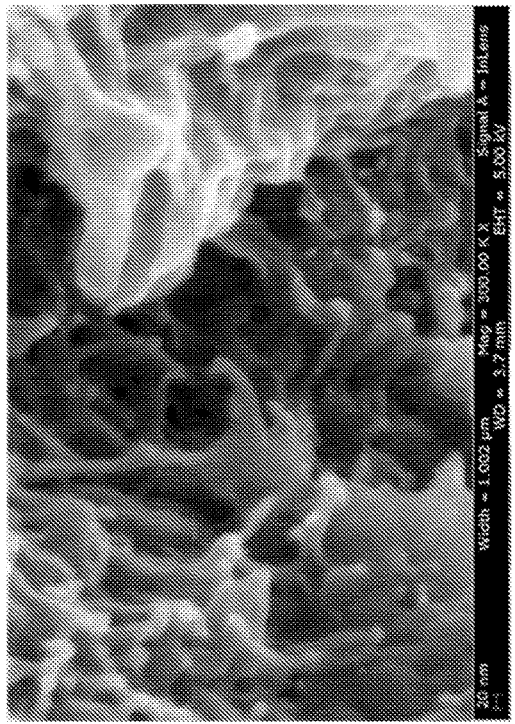
Figure 9B:
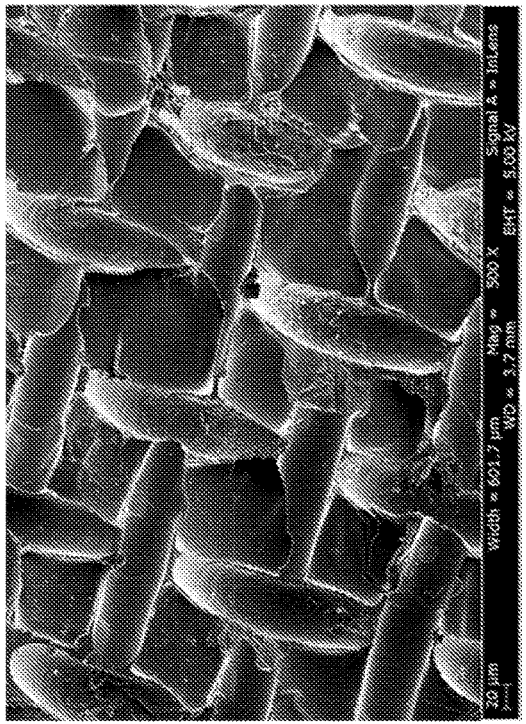
Figure 9D:
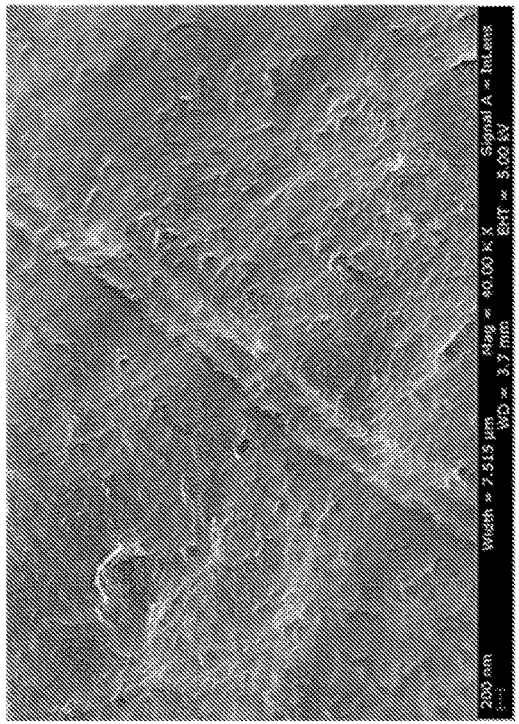
Figure 10A:
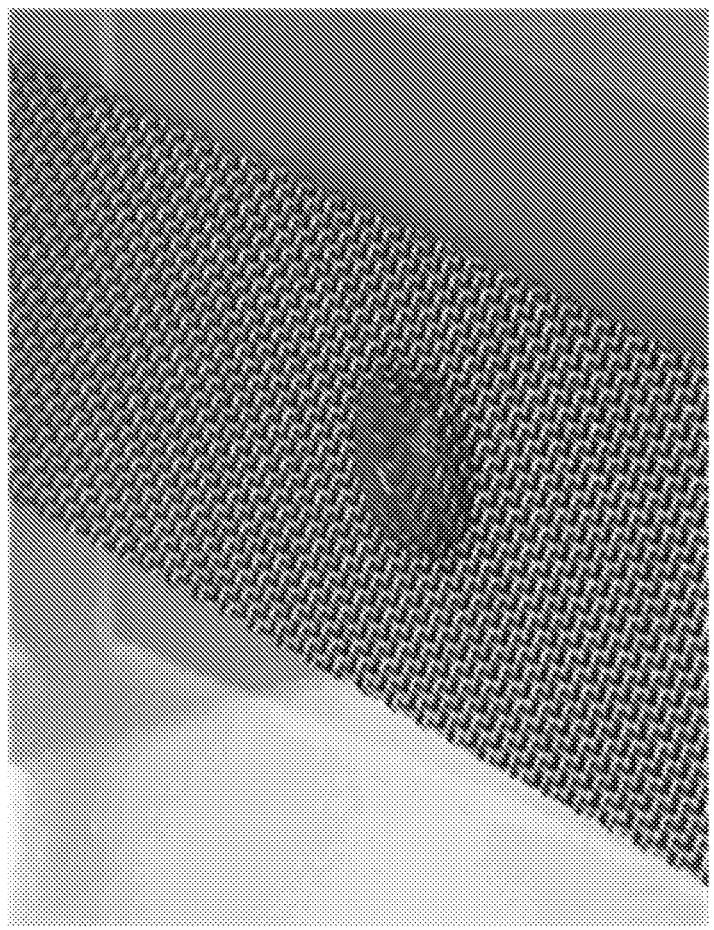
FIG. 10A is a photograph of a CsgA-TTF2-based biologic hydrogel transferred onto a metal mesh substrate. The hydrogel was dried on the metal mesh substrate and removed from the substrate after drying.
Figure 10C:
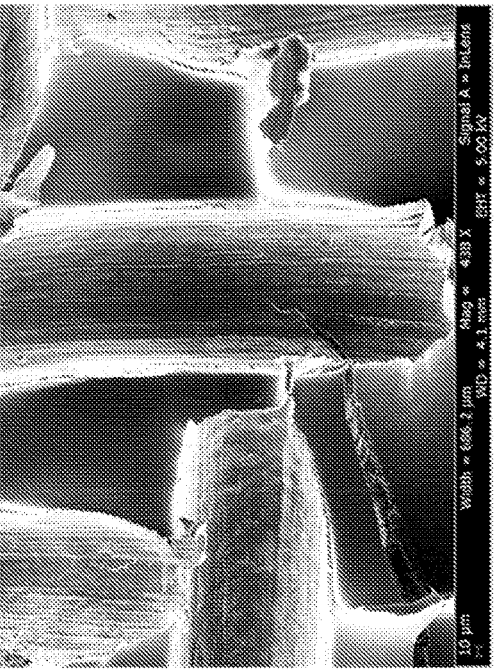
FIGS. 10B, 10C, 10D, and 10E depict the morphology of the CsgA-TTF2-based curli nanofiber film sample as observed by SEM.
Figure 10E:
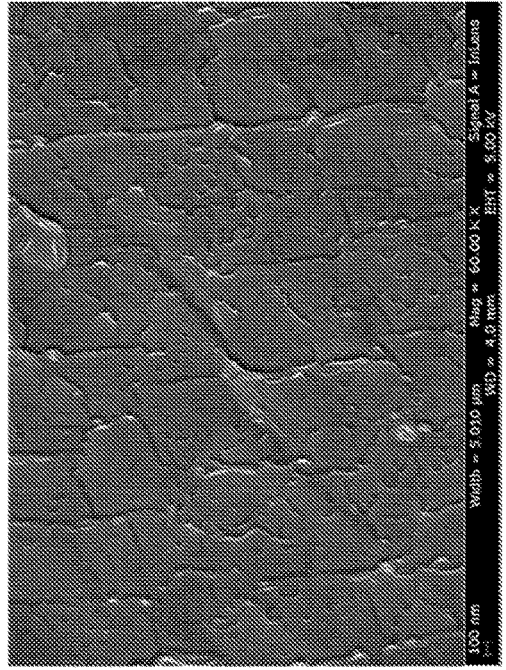
Figure 10B:
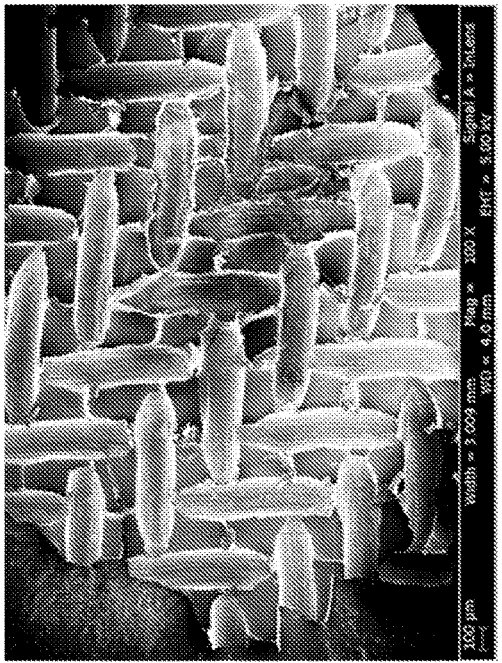
Figure 10D:
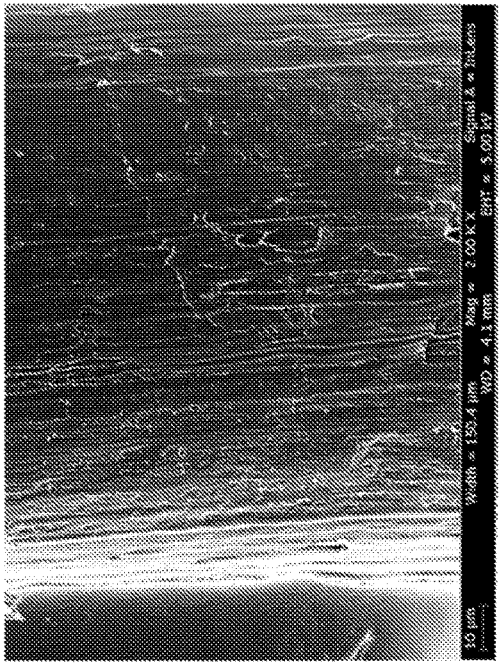
Figure 11B:
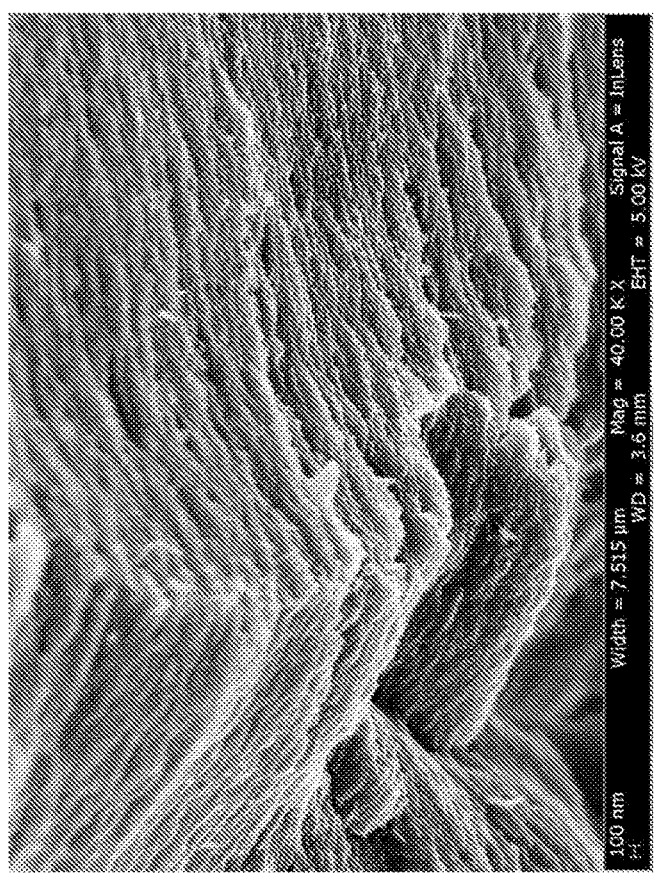
FIGS. 11A and 11B show SEM images of a collapsed curli nanofiber matrix.
Figure 11A:
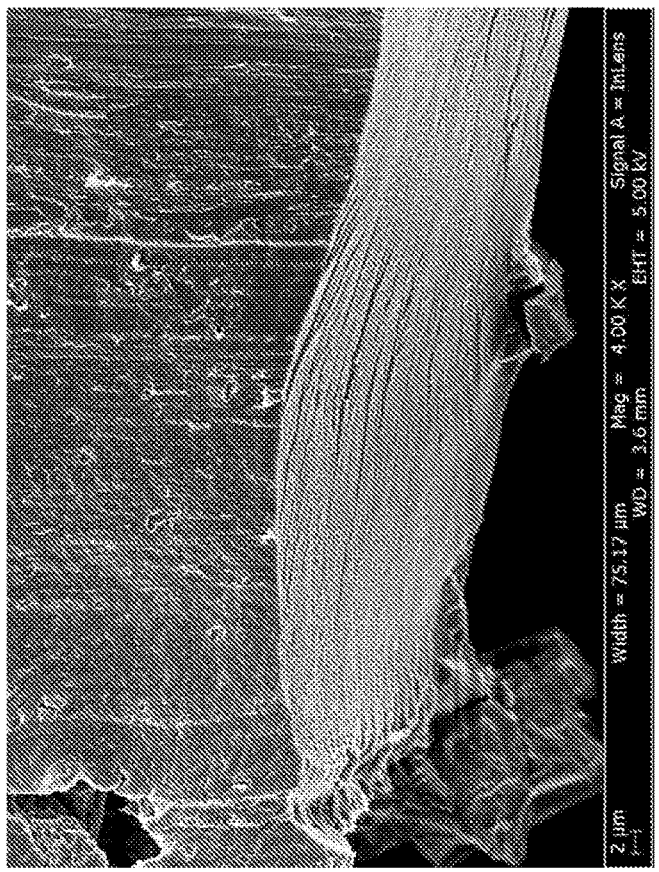
Figure 12C:
FIGS. 12A, 12B, 12C and 12D show a CsgA-TTF2-based curli nanofiber film imprinted on a nylon filter as observed by SEM.
Figure 12D:
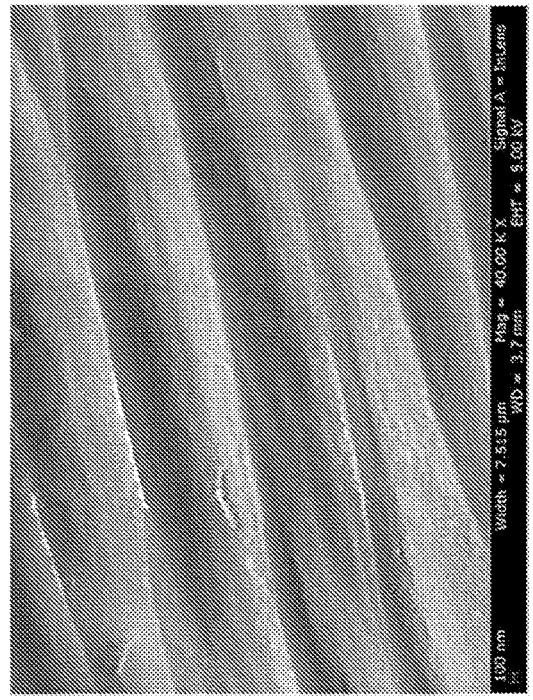
Figure 12A:
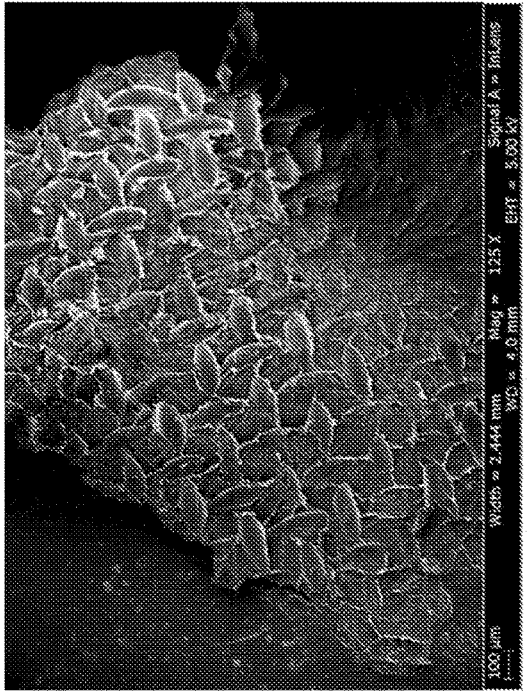
Figure 12B:
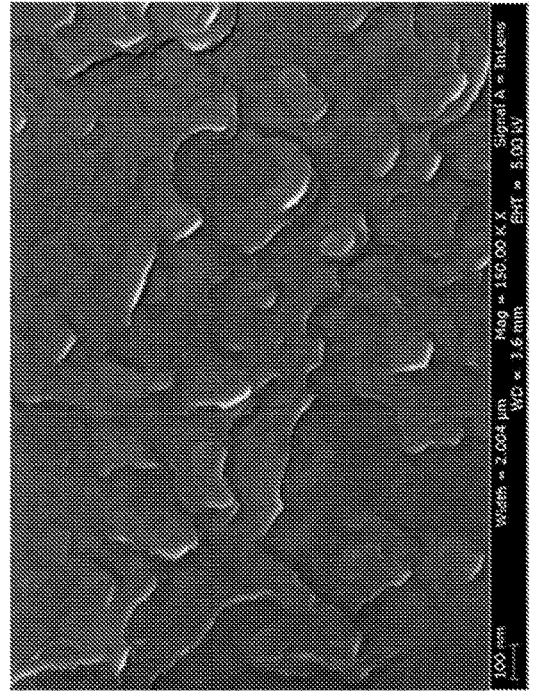
Figure 13B:
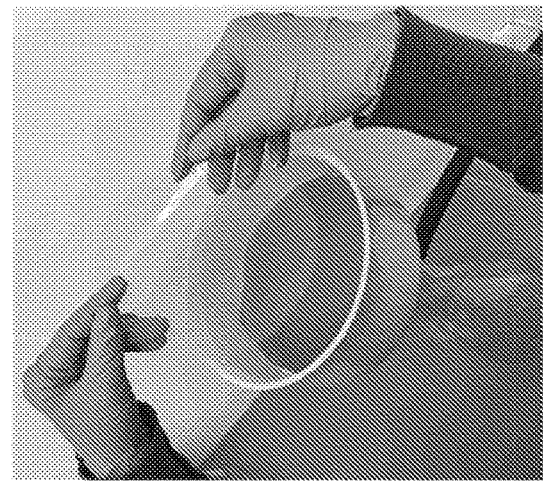
FIGS. 13A, 13B, and 13C depict photographs of a large scale production of engineered curli nanofiber-based materials.
Figure 13A:
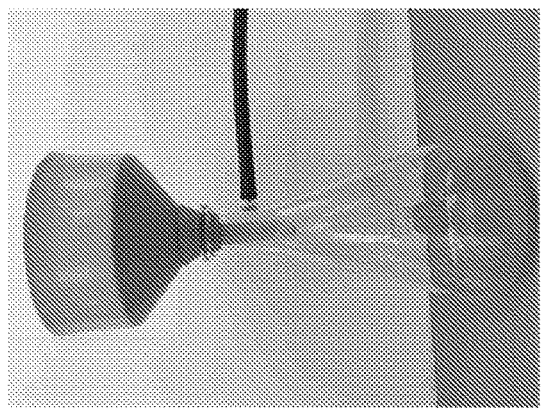
Figure 13C:
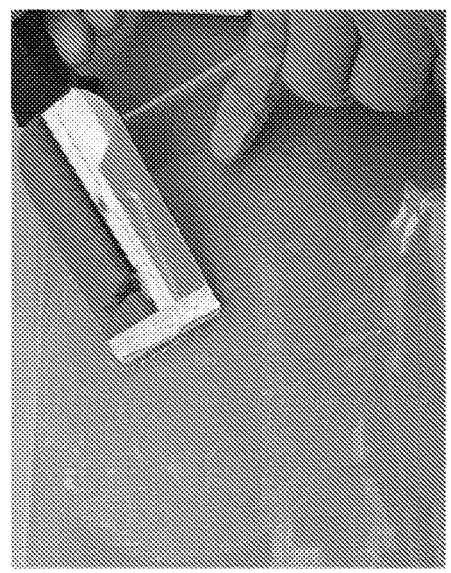
Figure 14:
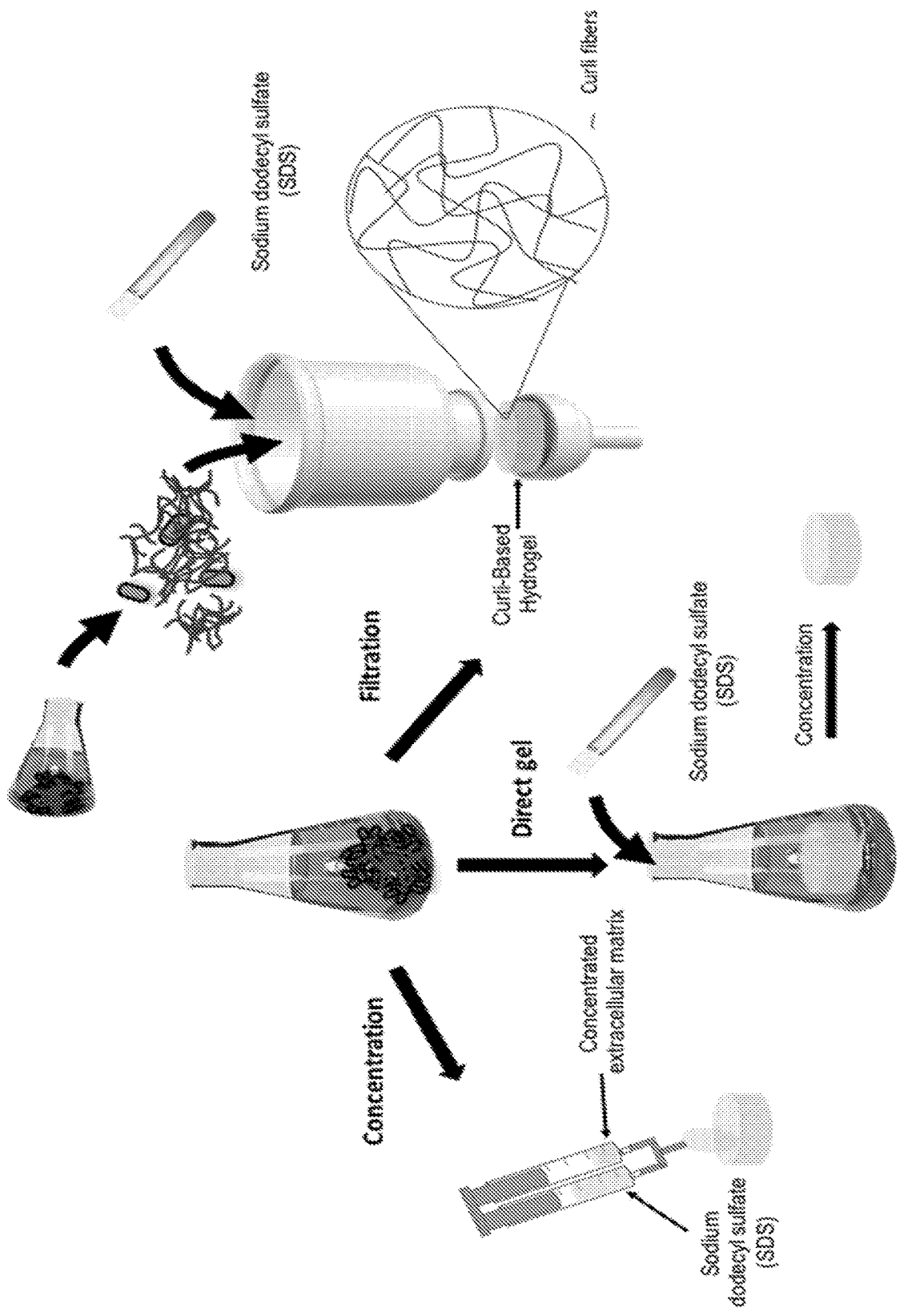
FIG. 14 depicts an exemplary schema for producing a biologic hydrogel directly from a bacterial culture.

Preparation of a hydrogel: FIG. 3 and FIG. 4 depict schemes for the formation of curli nanofiber hydrogels. Generally, the curli nanofibers comprising the CsgA fusion proteins are incubated with 0.8M guanidine HCl for 1 hour, and are subsequently incubated with 8M guanidine HCl for 5 minutes to lyse cells and to partially (or completely) denature the curli nanofibers. The reaction is subsequently incubated with DNase (and/or RNase) for 10 minutes to digest nucleic acids that binding to the curli nanofibers. The reaction is then incubated with 5% SDS for 5 minutes. An SDS incubation step was selected as the last step in the purification process because it allows for the delamination of the curli nanofiber films from the filter membranes. The resulting curli nanofiber hydrogels are removed from the filter membrane.

To demonstrate the presence of the curli nanofibers, the hydrogels can be stained with Congo Red stain or Thioflavin T.

Electron microscopy: Scanning electron microscopy was used to visualize the curli hydrogels directly on filter membranes (FIG. 7A).

Example 2: Preparation of Curli Nanofiber Aerogels

Preparation of aerogel: The aerogels are prepared in the same way as provided in Example 1 (Preparation of Curli Nanofiber Hydrogels), with the exception that the resulting hydrogel is lyophilized using a critical point dryer, lyophilizer, to slow the evaporation after solvent exchange, in a low surface tension solvent. However, one of ordinary skill in the art would understand that any other method for preparing an aerogel can be used, such that the method preserves the structure and porosity of hydrogel.

To demonstrate the presence of the curli nanofibers, the aerogels can be stained with Congo Red stain or Thioflavin T.

Example 3: Preparation of Curli Nanofiber Films

Preparation of films: The films are prepared in the same way as provided in Example 1 (Preparation of Curli Nanofiber Hydrogels), with the exception that the resulting hydrogel is simply air-dried at any temperature, or dried under vacuum at room temperature. The hydrogels can also be dried by changing humidity or by changing gases (or reactive gases). Drying of the hydrogels can be performed on a flat surface or a mesh pattern, mold, or other material substrate (e.g., including, but not limited to mesh, polymer mesh, or any flexible material) that allow the removal of the film to create a free-standing film.

To demonstrate the presence of the curli nanofibers, the films can be stained with Congo Red stain or Thioflavin T.

Example 4: Imprinting of Micro and Nano Features on Films

The curli nanofiber films prepared in Example 3 can be used to imprint micro and nano features on the films using, e.g., microfluidic molds and channels. FIGS. 9, 10, and 12 provide examples of imprinted curli nanofiber films.

Example 5: Genetically Engineered Bacterial Derived Amyloid-Based Hydrogel, Aerogel and Free-Standing Film 1. Description of existed Amyloidogenic Hydrogel, Aerogel and films
   Compositions of amylogenic hydrogels: systetic amyloidogenic peptides, expressed and purifies amylogenic peptides from bacteria Mechanism of creation of amyloid based hydrogels
2. Engineering curli based hydrogel
   a. C-terminal CsgA: any protein and large domain, peptide that can partially unfold or complitly under denaturation condition including TFFS and any disulfide containing peptides and proteins,
   b. N-terminal CsgA: any functional tag, peptide and protein.
   c. Any amyloidogenic peptide or protein that can be secreted any bacteria
3. Lyophilizing to make aerogels (maintain porous structure and function) using critical point dryer, lyophilizer, slowing evaporation after solvent exchange in low surface tension solvent or any other method which can preserve structure and porosity of hydrogel
4. Making film by drying curli based hydrogel in air under any temp, vacuum in RT and higher by changing huminity or by changing gases or reactive gases. Drying on flat surface or any mesh pattern, mold material including mesh, polimer mesh, flexible material that allow to remove film to create free standing film, or any not flexible material that can be used as substrate
5. Imprinting micro and nano futures on film including microfluidic molds and channel, any kind of texture and molecular imprinting
6. Making amyloid based composite materials including
   a. any polimers including, hydrophobic, hydrophilic, charge and uncharged, conductive, biodegradable, fibrilar (cellulose, chitin, chitosine, alginate)
   b. any nanomaterials, nanoparticules, graphines, quanto dots, carbon nano tubes, metalloorganic frameworks
   c. any biological material, protein, viruses, any microorganism, biopolymers, DNA
   d. any small molecules organic and non organic, therapeutics, dyes and pestidies, ions,
7. Applications of Amyloidogenic Hydrogel, Aerogel and Free-standing film:
   Therapeutics and wound healing and tissue engineering, implantation to tissue to replace natural mucosa and delivery of drugs
   Catalysis, contamination, water purification, sensing, conductive, electro chemically active, fluorescent, photoactive
   Absorbing agent (any contaminants, solvent, gases filtration, lightweight structural material)
   Microfluidic device, portable sensing, functional paper Example 6: Methods of Making a Biologic Hydrogel Biologic hydrogel based on a microbial culture were prepared using three different methods, depicted in FIG. 1: (a) filtration; (b) direct in the flask (c) concentration of the culture.

A. Preparation of Biologic Hydrogels Comprising Live Bacterial Cells by Filtration A biologic hydrogel comprising live bacterial cells was prepared by concentrating a culture of engineered bacterial cells expressing curli fibers comprising one of the fusion proteins CsgA-TFF1, CsgA-TFF2, CsgA-TFF3, or CsgA-MAM with a 47 mm polycarbonate filter membranes with 10 μm pores (EMD Millipore) using vacuum filtration. The concentrated fibers membranes were rinsed 3 times on the filter membrane with 25 ml of sterile deionized water. Next, the filtered fibers were incubated with 5 ml of 5% (w/v) sodium dodecyl sulfate (SDS) in water for 5 min, followed by vacuum filtration of the liquid and 3 rinses with 25 mL of deionized water. Hydrogels formed on the filter membrane were collected by gently scraping with a spatula, and the hydrogels were stored wet at 4° C. or lyophilized for further studies.

B. Preparation of Bacteria-Free Biologic Hydro Gels

A culture of engineered bacterial cells expressing curli fibers comprising one of the fusion proteins CsgA-TFF1, CsgA-TFF2, CsgA-TFF3, or CsgA-MAM was incubated with guanidinium chloride (GdmCl) (to a final concentration 0.8M) at 4° C. After 1 hour incubation, the culture was transferred onto a 47 mm polycarbonate filter membranes with 10 μm pores, via vacuum filtration. To remove live bacteria, the filter membrane was incubated with 5 mL of 8 M GdmCl for 5 min, followed by vacuum filtration of the liquid, and 3 rinses with 25 mL of sterile deionized water. Next, the curli-TFF fibers were treated with 5 mL of an aqueous solution (2 μM $MgCl_2$) of nuclease (Benzonase, Sigma-Aldrich, 1.5 U/ml) for 10 min to remove DNA/RNA bound to curli fibers. Finally, the semi-purified bacteria-free fibers were incubated with 5 ml of 5% (m/v) SDS in water for 5 min followed by vacuum filtration of the liquid and 3 rinses with 25 mL of DI water. The bacteria-free hydrogel was collected from the filter membranes and stored wet at 4° C. or lyophilized for the further studies.

The protocol described above was also performed using several variations in either the concentration of surfactant, the surfactant used, the amount of time that three microbial culture was exposed to the surfactant, the concentration of and type of denaturing agent, and treatment with or without DNAse to assess the effect of each treatment variation on the the weight and water content of the formed biologic hydrogel. The results of these experiments are described at FIGS. 15A-15D and Table 4 (below).

TABLE 4

Effect of Variations in Protocol Used to Generate Biologic Hydrogel on the Weight and Water Content of Formed Bacteria-Free Biologic Hydrogels

| Treatment | Treatment Group | Reagent | Gel Weight (mg) | Dry Mass (mg) | Water % |
|---|---|---|---|---|---|
| Ionic Surfactant | 1 | no SDS 5 min | N/A | N/A | N/A |
| | 2 | 5% SDS 1 min | 97.8 | 2.6 | 97.3 |
| | 3 | 5% SDS 5 min | 69.9 | 4.2 | 94.0 |
| | 4 | 5% SDS 15 min | 129.8 | 3.1 | 97.6 |
| | 5 | 5% SDS 1 hr | 117.2 | 5.5 | 95.3 |
| | 6 | 0.1% SDS 5 min | 9.0 | 0.7 | 92.5 |
| | 7 | 1% SDS 5 min | 96.1 | 2 | 97.9 |
| | 8 | 10% SDS 5 min | 89.0 | 2.7 | 97.0 |
| | 9 | sarcosyl | 77.7 | 2.1 | 97.3 |
| Non-ionic Surfactant | 10 | Triton X-100 | N/A | N/A | N/A |
| | 11 | Tween-20 | N/A | N/A | N/A |
| Denaturing Agents | 12 | 0M/0M GdmCl | 56.3 | 1.9 | 96.4 |
| | 13 | 0M/8M GdmCl | 139 | 3.9 | 97.2 |

TABLE 4-continued

Effect of Variations in Protocol Used to Generate Biologic Hydrogel on the Weight and Water Content of Formed Bacteria-Free Biologic Hydrogels

| Treatment | Treatment Group | Reagent | Gel Weight (mg) | Dry Mass (mg) | Water % |
|---|---|---|---|---|---|
| | 14 | 0.8M/0M GdmCl | 142.0 | 4.7 | 96.7 |
| | 15 | 0.8M/2M GdmCl | 138.2 | 8.8 | 93.6 |
| | 16 | 0.8M/4M GdmCl | 69.7 | 4.9 | 92.8 |
| | 17 | 0.8M/8M GdmCl | 69.9 | 4.2 | 94.0 |
| | 18 | 0.8M/8M urea | 113 | 6.8 | 93.9 |
| Non-denaturing Agent | 19 | 0.5%/5% DMSO | 108.1 | 6.2 | 94.2 |
| | 20 | 0.5%/5% SDS | 26.9 | 0.9 | 96.6 |
| DNA removal | 21 | No DNase | 114.9 | 3.2 | 97.2 |
| | 22 | DNAse | 69.9 | 4.2 | 94.0 |

C. Preparation of Biologic Hydrogels Direct-in-Flask

A culture of engineered bacterial cells expressing curli fibers comprising one of the fusion proteins CsgA-TFF1, CsgA-TFF2, CsgA-TFF3, or CsgA-MAM was incubated with the surfactant sodium dodecyl sulfate (SDS) at a final concentration 5% (m/v). After 30 min of incubation at room temperature, hydrogel was formed in the flask. To concentrate the hydrogel, all flask content was subjected to vacuum filtration to remove remaining medium.

D. Preparation of Biologic Hydrogels Using Pelleted Bacterial Cells

To make hydrogel in semi-instant method, the culture of engineered bacterial cells expressing curli fibers comprising one of the fusion proteins CsgA-TFF1, CsgA-TFF2, CsgA-TFF3, or CsgA-MAM was concentrated by centrifugation. The pellet was transferred to one of barrel of a dual barrel syringe. In the second barrel of the syringe, 10-20% of sodium dodecyl sulfate (SDS) was added. Upon being contacted with the SDS solution, the pellet hydrogel was formed.

Example 7: Rheological Studies of Biologic Hydrogels

To determine the rheological properties of biologic hydrogels comprising curli fiber comprising CsgA fusion proteins, rheology measurements to determine the storage moduli and loss moduli of biologic hydrogels were performed. Small strain amplitude oscillatory rheology measurements were performed on a TA Instruments AR-G2 rheometer with plate-plate geometry. 8 mm plates were used for strain sweeps and frequency sweeps with a gap width of 500 um and moisture trap. Strain sweep measurements were carried out from a strain amplitude of 0.1% to 25% at 25.0° C. (+/−0.1° C.) and a frequency of 1.000 Hz to determine small deformation linearity. Frequency sweeps were then performed from 0.1 Hz to 100 Hz at 25.0° C. with a controlled strain amplitude of 1.0%, which was within the linear response range for all samples.

To determine the effect of the presence of bacterial cells on biologic hydrogels on the storage moduli and loss moduli of the hydrogels, biologic hydrogels were prepared from a microbial culture, and the biologic hydrogels were prepared as described in Example 6, with and without guanidine hydrochloride treatment, which kills bacterial cells. The storage modulus (G') and loss modulus (G") for both of the hydrogels is shown in FIG. 18A.

To determine the effect of disulfide bonding of the curli fibers on the rheological properties of biologic hydrogels, hydrogels prepared using cultures of either bacterial cells that produced curli fiber comprising a CsgA fusion protein comprising CsgA fused to TTF2 (non-mutant), or bacterial cells that produced curli fiber comprising a CsgA fusion protein comprising CsgA fused to TTF2 ("CTFF2"), wherein all cysteines of the fusion protein had been mutated to alanine residues ("CTFF2NS"), were tested. The storage modulus (G') and loss modulus (G") for both of the hydrogels is shown in FIG. 18B.

To determine the effect of treatment with DNAse on the rheological properties of biological hydrogels, hydrogels prepared using cultures of bacterial cells that produced curli fibers comprising either CsgA-TFF1 ("CTFF1"), CsgA-TFF2 ("CTFF2"), or CsgA-TFF3 ("CTFF3") that were treated with DNAse, or not treated with DNAse, were tested. The storage modulus (G') and loss modulus (G") for each of the hydrogels prepared without DNAse treatment is shown in FIG. 18C. The storage modulus (G') and loss modulus (G") for each of the hydrogels prepared without DNAse treatment is shown in FIG. 18D.

Example 8: Measurement of the Adhesion Strength of a Mucoadhesive Biologic Hydrogel To test the adhesion strength of a biologic hydrogel comprising curli fibers comprising CsgA-TFF2 (also referred to as "cTFF2 gel") to the gut mucosa, freshly made the live hydrogel was placed on the mucosal or the serosal site of a fresh goat colon. The goat colon was cut open longitudinally along the main axis. The sliced colon samples were fixed on standard SEM pin stub mount (012.7 mm×8 mm pin height, Electron Microscopy Sciences) using instant glue (Loctite 495, Henkel). The 50 µl of the CTFF2 gel was applied onto the tissue sample and cover with the second layer of tissue fixed to SEM pin stub to form layered tissue-hydrogel-tissue sandwiches (see image at FIG. 20A). Water was used in lieu of hydrogel as control. These layered tissue-hydrogel-tissue sandwiches were kept at room temperature during 30 minutes to achieve integration of hydrogel with the gut mucosa. Finally, SEM pin stubs with hydrogel and tissue samples were loaded on the bottom stage of the mechanical tester (ADMET) and pulled off with a constant strain of 8 mm/min. The applied force was monitored and the maximum force before full detachment of the patch was measured as the adhesion force. All of the experiments were performed in triplicate. The adhesion strength of the CTFF2 gel, as compared to the water control, to either the mucosal or the serosal site the goat colon tissue is shown at FIG. 20B. The biologic hydrogel is able to adhere to mucosal epithelium surface of the goat colon. The shear-thinning behavior of the hydrogel for deliver of the hydrogel directly to the gut by injection or by spraying by an endoscopic device.

Example 9: Oral Administration of Labeled Hydrogel and Whole Gastrointestinal Tract Ex Vivo Optical Imaging To determine whether a biologic hydrogel comprising curli fibers comprising either CsgA-TFF1 "cTFF1"), CsgA-TFF2 ("cTFF2"), or Csga-TFF3 ("cTFF3") could be delivered in vivo and exhibit mucoadhesive properties, the following experiments were performed in mice. Before the administration of labeled hydrogel, mice were fed with a non-fluorescent food (alfalfa-free) for at least 5 days to minimize background autofluorescence. Mice were administered Cy7-labeled cTFF1, cTFF2, or cTFF3 biologic hydrogels (150 µL) by oral gavage to C57BL/6 mice. At t=0, 3, 6, 24 and 48 hours after gavaging, a mouse from each group was euthanized to harvest the whole GI tract for ex vivo imaging. The whole GI tract was placed on the lid of 150×25 mm polystyrene tissue culture plate (Falcon™). An IVIS Lumina II instrument (PerkinElmer®) equipped with 10 narrow-band excitation filters (30 nm bandwidth) and 4 broadband emission filters (60- and 75-nm bandwidth) was used for the ex vivo optical imaging. At each time point, the whole GI tracts were imaged with using excitation filter at 710 nm, and 675 nm for background subtraction, and emission filter at 810-875 nm, with field of view (FOV)=D (12.5 cm), fstop=2 and medium binning Imaging analysis was performed using Living Image software version 4.3.1/4.4. These in vivo studies demonstrated that the biologic hydrogels could be successfully delivered to the gut of mice and exhibited mucoadhesive properties. As shown in FIG. 21A, the hydrogels were detected in the gut up to 48 hours after administration.

Example 10: Generation of Curli-Based Thin Films and 3D Structures

Free Standing curli-based films have been developed using biologic hydrogels described above. The methods described herein provide an easy, fast and economic methods of production of customizable thin curli based films and 3D-structures. The biologic hydrogels described herein may be used for the production of scalable materials that can be utilized to create 2D thin films with the specific functions. In addition, by using 3D molds, biologic hydrogel can be produced having three-dimensional shapes that can be used as a building blocks to create larger 3D structures.

FIG. 23 depicts a scheme for fabrication thin films and 3D structures from the biologic hydrogels described herein. First, a culture of bacterial cells expressing curli fibers is filtered onto a membrane or concentrated by centrifugation (or other concentration means such as centrifugation). The culture can be combined with a surfactant to speed up gelation, or be left in a concentrated state to produce a hydrogel. After the hydrogel is formed, the culture can be applied as a coating onto a variety of substrates (e.g., plastic pellicle, foil, metal meshes, polymer meshes, etc.) and left to air-dry at room temperature. During drying, curli fibers collapse onto each other and form a multilayer structure. Drying conditions can be modified to speed up (by applying heat or drying under vacuum) or slow down (increasing the humidity, decreasing temperature, exchanging water for a high boiling point solvent) the drying.

Partially-dried thin films can be captured, and they typically exhibit high flexibility and stretchability. The partially-dried state can be maintained over time by placing the gel in a highly humid environment, or by subjecting the hydrogel to solvent exchange using a high boiling point solvent (such as glycerol, chlorobenzene, or dimethylformamide).

If the thin film is left to dry completely, it forms a dried conformal coating onto the substrate. Using a flexible substrate allows for an easy delamination of the film to produce a free-standing thin film. Curli fibers can also be integrated within a porous substrate (within a porous metal mesh for instance) and could give additional functionalities to porous materials. Alternatively, if the substrate is not flat or if the gel is dried onto a complex 3D mold, a dried 3D coating can be obtained. After removal of the 3D mold, a 3D shape made entirely of curli fibers can be obtained.

The morphology and physical properties of thin films can be modulated by fabrication method that have been applied to make the curli hydrogel. Bacteria-free hydrogel made by treatment of bacterial cultures with guanidine hydrochloride and SDS allow for the formation of thin films with tightly collapsed curli layers. However, cross section of the film made from live hydrogel (SDS treatment only) shows a bacteria still present between collapsed curli layers as shown in FIG. 24.

The methods used to fabricate the biologic hydrogel may influence the ability to rehydrate a dried thin film. As shown on FIG. 25, thin film produced from live hydrogels (i.e., hydrogels comprising live bacterial cells) return to their hydrated state after rehydration with water. This behavior allows for the generation of thin films that can be recycled back into hydrogel state which can further be used to cast a thin film, for example, in a different mold. Furthermore, thin films made using biologic hydrogel fabricated using pretreatment with 0.8 M guanidine hydrochloride for 1 hour followed by treatment with guanidine hydrocholoride and SDS for 5 minutes, do not rehydrate. However, hydrogels made using guanidine hydrochloride pretreatment result in thin films that can only be partially hydrated to create thin, transparent flexible thin films.

In addition to modulating the physical and morphological properties of thin films by changing composition of hydrogel, a direct method for manipulating the physical properties of the thin films by imprinting them using specific patterns on the surface of film was developed. As shown on FIGS. 26A-26C, thin films were generated by drying the biologic hydrogel using thick and fine metal meshes and nylon membranes as templates. Using this simple method, high resolution micro and nanometer scale patterns can be imprinted onto the films. This technique allows for the generation of thin films having modulated surface properties.

As a proof of concept, properties of the thin film, such as hydrophobicity and hydrophilicity were modulated. Using a Taro leaf as a template, thin films were generated by drying hydrogels directly on the surface of the leaf as shown in FIGS. 27A-27D. Thin films formed using a Taro leaf as template exhibited a more hydrophobic surface than thin films formed using a flat plastic surface as template (FIG. 28). Imprinting could also be used to modify other surface properties of curli thin films, such as binding affinities (molecular imprinting), optical properties (light scattering, transparency) and roughness.

The thin films comprising a curli fiber described herein may also be used as building blocks to fabricate or assemble a three dimensional (3D) structure. As a proof of concept, two assemblies using thin films were prepared as shown in FIGS. 32A-32D (a perpendicular assembly), and 33A-33D (a parallel assembly). First, a drop of water was added to a first dried thin film (i.e., a portion of the thin film rehydrated). A second thin film was attached to the hydrated portion of the first film. The hydrated portion of the thin films served as the attachment point and adhesive for the two thin films. After drying, the first and second thin films were attached together to form a three dimensional structure. The films can be assembled in different arrangements, e.g., flat junction, perpendicular junction, etc., to create larger 3D structures.

The invention claimed is:

1. A biologic hydrogel comprising a curli fiber and a surfactant, wherein the hydrogel comprises at least 3% (w/w) curli fiber, wherein the curli fiber comprises a wild-type CsgA or an engineered CsgA fusion protein, and wherein the engineered CsgA fusion protein comprises a CsgA polypeptide fused to an activity polypeptide.

2. The biologic hydrogel of claim 1, wherein the activity polypeptide is a mucoadhesive polypeptide, a porin, a ribosomal protein or a plastocyanin.

3. The biologic hydrogel of claim 2, wherein the mucoadhesive polypeptide is selected from the group consisting of: trefoil factor 1 (TFF1), trefoil factor 2 (TFF2), trefoil factor 3 (TFF3), and a microbial anti-inflammatory molecule (MAM) domain.

4. The biologic hydrogel of claim 1, wherein CsgA fusion protein comprises a linker polypeptide linker sequence adjoining the CsgA polypeptide and the activity polypeptide.

5. The biologic hydrogel of claim 1, wherein the engineered CsgA fusion protein further comprises a polypeptide tag selected from the group consisting of a poly-histidine tag, a myc tag, a FLAG tag, a hemagglutinin (HA) tag, and a V5 tag.

6. The biologic hydrogel of claim 1, comprising a cell, wherein the cell is a bacterial cell, a mammalian cell, a protozoan, or a fungus.

7. The biologic hydrogel of claim 6,
wherein the cell is a bacterial cell, and wherein the bacterial cell comprises a heterologous nucleic acid, which comprises a heterologous gene encoding the engineered CsgA fusion, or
wherein the bacterial cell comprises a heterologous nucleic acid, which comprises a heterologous gene encoding a polypeptide selected from the group consisting of an extracellular matrix component, a therapeutic polypeptide, a mucoadhesive polypeptide, a cytokine, an enzyme, an antibody, or an antibody mimetic sequence.

8. The biologic hydrogel of claim 1, wherein the hydrogel comprises a nucleic acid, an extracellular matrix component, a polysaccharide, a metabolite, a metal ion, a nanoparticle, a polypeptide, cellulose, a vitamin, a nutraceutical, or a detectable compound.

9. The biologic hydrogel of claim 1, wherein the biologic hydrogel is suitable for use in an application selected from the group consisting of: biocatalysis, chemical production, filtration, isolation of molecules from an aqueous solution, water filtration, bioremediation, nanoparticle synthesis, nanowire synthesis, display of optically active materials, surface coating, structural reinforcement of an object, and delivery of a therapeutic agent, or wherein the biologic hydrogel is suitable for use as a therapeutic biomaterial, a biological scaffold, a delivery system for therapeutic agents, a biosensor, a biocatalyst, a coating, and an electronically conductive material.

10. A particle comprising the biologic hydrogel of claim 1.

11. A pharmaceutical composition comprising the biologic hydrogel of claim 1, and a pharmaceutically-acceptable excipient.

12. The biologic hydrogel of claim 1, wherein the hydrogel comprises at least 5% (w/w) curli fiber.

13. The biologic hydrogel of claim 12, wherein the hydrogel comprises at least 10% (w/w) curli fiber.

* * * * *